(12) United States Patent
Anderson et al.

(10) Patent No.: US 10,647,750 B2
(45) Date of Patent: May 12, 2020

(54) CATIONIC NEUROTOXINS

(71) Applicant: IPSEN BIOINNOVATION LIMITED, Abingdon, Oxfordshire (GB)

(72) Inventors: Dina Brady Anderson, Abingdon (GB); Gavin Stephen Hackett, Abingdon (GB); Sai Man Liu, Abingdon (GB)

(73) Assignee: IPSEN BIOINNOVATION LIMITED, Abingdon (GB)

( * ) Notice: Subject to any disclaimer, the term of this patent is extended or adjusted under 35 U.S.C. 154(b) by 155 days.

(21) Appl. No.: 15/540,637

(22) PCT Filed: Jan. 9, 2015

(86) PCT No.: PCT/GB2015/050043
§ 371 (c)(1),
(2) Date: Jun. 29, 2017

(87) PCT Pub. No.: WO2016/110662
PCT Pub. Date: Jul. 14, 2016

(65) Prior Publication Data
US 2018/0141982 A1 May 24, 2018

(51) Int. Cl.
| | | |
|---|---|---|
| C07K 14/33 | (2006.01) | |
| A61K 8/64 | (2006.01) | |
| A61Q 19/08 | (2006.01) | |
| A61K 8/99 | (2017.01) | |
| A61P 17/00 | (2006.01) | |
| A61P 25/08 | (2006.01) | |
| A61P 25/16 | (2006.01) | |
| A61P 25/06 | (2006.01) | |
| A61K 38/48 | (2006.01) | |
| A61K 38/00 | (2006.01) | |

(52) U.S. Cl.
CPC ............... *C07K 14/33* (2013.01); *A61K 8/64* (2013.01); *A61K 8/99* (2013.01); *A61K 38/4893* (2013.01); *A61P 17/00* (2018.01); *A61P 25/06* (2018.01); *A61P 25/08* (2018.01); *A61P 25/16* (2018.01); *A61Q 19/08* (2013.01); *C12Y 304/24069* (2013.01); *A61K 38/00* (2013.01)

(58) Field of Classification Search
None
See application file for complete search history.

(56) References Cited

FOREIGN PATENT DOCUMENTS

WO WO-2013068476 A1 * 5/2013 ......... C07K 14/4746

* cited by examiner

*Primary Examiner* — Brian Gangle
(74) *Attorney, Agent, or Firm* — Gene J. Yao; Barnes & Thornburg LLP

(57) ABSTRACT

Engineered clostridial toxins comprising an amino acid modification that increases the isoelectric point of the engineered clostridial toxin to a value that is at least 0.2 pI units higher than the isoelectric point of an otherwise identical clostridial toxin lacking the modification, wherein the modification is not located in the clostridial toxin binding domain ($H_C$ domain).

Figure 1A:
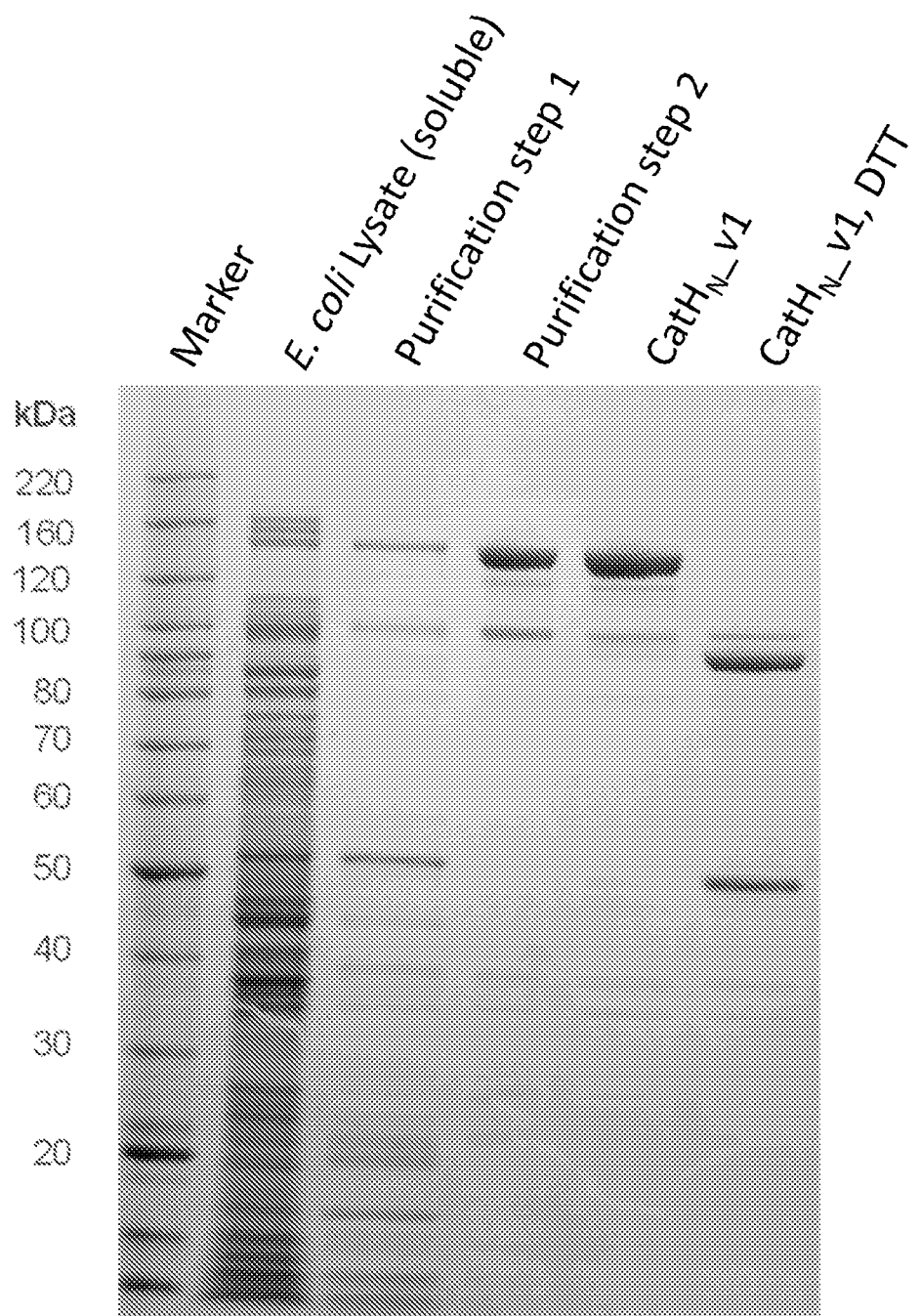

18 Claims, 12 Drawing Sheets
Specification includes a Sequence Listing.

Figure 2.

|  | pEC$_{50}$ |
|---|---|
| BoNT/A | 12.26 ± 0.13 |
| CatH$_{N}$_v1 | 12.00 ± 0.09 |

Figure 4.

% SNAP-25 cleavage vs log [BoNT] M

|  | pEC$_{50}$ |
|---|---|
| CatH$_N$_v2 | 12.94 ± 0.16 |

Figure 5.

|  | $t_{50}$ (mean ± sem, min) |
|---|---|
| BoNT/A | 40 ± 1 |
| CatH$_N$_v2 | 42 ± 1 |

Figure 6.

|  | pEC$_{50}$ |
|---|---|
| BoNT/A | 11.94 ± 0.06 |
| CatH$_{N\_}$v3 | 9.84 ± 0.04 |

Figure 7.

| | $t_{50}$ (mean ± sem, min) |
|---|---|
| BoNT/A | 40 ± 1 |
| CatH$_N$_v3 | 127 ± 1 |

Figure 8.

| Lane | Construct | Calculated pI | Observed pI |
|------|-----------|---------------|-------------|
| 1 | BoNT/A | 6.4 | 7.4 |
| 2 | CatH$_{N\_}$v1 | 7.4 | 7.8 |
| 3 | CatH$_{N\_}$v2 | 7.3 | 7.8-8.0 |
| 4 | CatH$_{N\_}$v3 | 7.1 | 7.8-8.0 |

Figure 10.

|  | Reference | CatLC |
|---|---|---|
| pEC50 | 10.6 | 10.6 |

SEQUENCE LISTING

```
<160> NUMBER OF SEQ ID NOS: 37

<210> SEQ ID NO 1
<211> LENGTH: 1296
<212> TYPE: PRT
<213> ORGANISM: Artificial sequence
<220> FEATURE:
<223> OTHER INFORMATION: Engineered BoNT/A

<400> SEQUENCE: 1

Met Pro Phe Val Asn Lys Gln Phe Asn Tyr Lys Asp Pro Val Asn Gly
1               5                   10                  15

Val Asp Ile Ala Tyr Ile Lys Ile Pro Asn Ala Gly Gln Met Gln Pro
            20                  25                  30

Val Lys Ala Phe Lys Ile His Asn Lys Ile Trp Val Ile Pro Glu Arg
        35                  40                  45

Asp Thr Phe Thr Asn Pro Glu Glu Gly Asp Leu Asn Pro Pro Pro Glu
    50                  55                  60

Ala Lys Gln Val Pro Val Ser Tyr Tyr Asp Ser Thr Tyr Leu Ser Thr
65                  70                  75                  80

Asp Asn Glu Lys Asp Asn Tyr Leu Lys Gly Val Thr Lys Leu Phe Glu
                85                  90                  95

Arg Ile Tyr Ser Thr Asp Leu Gly Arg Met Leu Leu Thr Ser Ile Val
            100                 105                 110

Arg Gly Ile Pro Phe Trp Gly Gly Ser Thr Ile Asp Thr Glu Leu Lys
        115                 120                 125

Val Ile Asp Thr Asn Cys Ile Asn Val Ile Gln Pro Asp Gly Ser Tyr
    130                 135                 140

Arg Ser Glu Glu Leu Asn Leu Val Ile Ile Gly Pro Ser Ala Asp Ile
145                 150                 155                 160

Ile Gln Phe Glu Cys Lys Ser Phe Gly His Glu Val Leu Asn Leu Thr
                165                 170                 175

Arg Asn Gly Tyr Gly Ser Thr Gln Tyr Ile Arg Phe Ser Pro Asp Phe
            180                 185                 190

Thr Phe Gly Phe Glu Glu Ser Leu Glu Val Asp Thr Asn Pro Leu Leu
        195                 200                 205

Gly Ala Gly Lys Phe Ala Thr Asp Pro Ala Val Thr Leu Ala His Glu
    210                 215                 220

Leu Ile His Ala Gly His Arg Leu Tyr Gly Ile Ala Ile Asn Pro Asn
225                 230                 235                 240

Arg Val Phe Lys Val Asn Thr Asn Ala Tyr Tyr Glu Met Ser Gly Leu
```

```
                    245                 250                 255
Glu Val Ser Phe Glu Glu Leu Arg Thr Phe Gly Gly His Asp Ala Lys
                260                 265                 270
Phe Ile Asp Ser Leu Gln Glu Asn Glu Phe Arg Leu Tyr Tyr Tyr Asn
                275                 280                 285
Lys Phe Lys Asp Ile Ala Ser Thr Leu Asn Lys Ala Lys Ser Ile Val
            290                 295                 300
Gly Thr Thr Ala Ser Leu Gln Tyr Met Lys Asn Val Phe Lys Glu Lys
305                 310                 315                 320
Tyr Leu Leu Ser Glu Asp Thr Ser Gly Lys Phe Ser Val Asp Lys Leu
                325                 330                 335
Lys Phe Asp Lys Leu Tyr Lys Met Leu Thr Glu Ile Tyr Thr Glu Asp
                340                 345                 350
Asn Phe Val Lys Phe Phe Lys Val Leu Asn Arg Lys Thr Tyr Leu Asn
                355                 360                 365
Phe Asp Lys Ala Val Phe Lys Ile Asn Ile Val Pro Lys Val Asn Tyr
            370                 375                 380
Thr Ile Tyr Asp Gly Phe Asn Leu Arg Asn Thr Asn Leu Ala Ala Asn
385                 390                 395                 400
Phe Asn Gly Gln Asn Thr Glu Ile Asn Asn Met Asn Phe Thr Lys Leu
                405                 410                 415
Lys Asn Phe Thr Gly Leu Phe Glu Phe Tyr Lys Leu Leu Cys Val Arg
                420                 425                 430
Gly Ile Ile Thr Ser Lys Thr Lys Ser Leu Asp Lys Gly Tyr Asn Lys
            435                 440                 445
Ala Leu Asn Asp Leu Cys Ile Lys Val Asn Asn Trp Asp Leu Phe Phe
            450                 455                 460
Ser Pro Ser Glu Asp Asn Phe Thr Asn Asp Leu Asn Lys Gly Glu Glu
465                 470                 475                 480
Ile Thr Ser Asp Thr Asn Ile Glu Ala Ala Glu Glu Asn Ile Ser Leu
                485                 490                 495
Asp Leu Ile Gln Gln Tyr Tyr Leu Thr Phe Asn Phe Asp Asn Glu Pro
            500                 505                 510
Glu Asn Ile Ser Ile Glu Asn Leu Ser Ser Asp Ile Ile Gly Gln Leu
            515                 520                 525
Glu Leu Met Pro Asn Ile Glu Arg Phe Pro Asn Gly Lys Lys Tyr Glu
            530                 535                 540
Leu Asp Lys Tyr Thr Met Phe His Tyr Leu Arg Ala Gln Glu Phe Glu
545                 550                 555                 560
His Gly Lys Arg Arg Ile Ala Leu Thr Asn Ser Val Asn Glu Ala Leu
                565                 570                 575
Leu Asn Pro Ser Arg Val Tyr Thr Phe Ser Ser Asp Tyr Val Lys
                580                 585                 590
Lys Val Asn Lys Ala Thr Glu Ala Ala Met Phe Leu Gly Trp Val Glu
                595                 600                 605
Gln Leu Val Tyr Asp Phe Thr Asp Glu Thr Ser Glu Val Ser Thr Thr
            610                 615                 620
Asp Lys Ile Ala Asp Ile Thr Ile Ile Pro Tyr Ile Gly Pro Ala
625                 630                 635                 640
Leu Asn Ile Gly Asn Met Arg Tyr Lys Arg Arg Phe Val Gly Ala Leu
                645                 650                 655
Ile Phe Ser Gly Ala Val Ile Leu Leu Glu Phe Ile Pro Glu Ile Ala
                660                 665                 670
```

-continued

```
Ile Pro Val Leu Gly Thr Phe Ala Leu Val Ser Tyr Ile Ala Asn Lys
        675                 680                 685

Val Leu Thr Val Gln Thr Ile Asp Asn Ala Leu Ser Lys Arg Asn Glu
        690                 695                 700

Lys Trp Asp Glu Val Tyr Lys Tyr Ile Val Thr Asn Trp Leu Ala Lys
705                 710                 715                 720

Val Asn Thr Gln Ile Asp Leu Ile Arg Lys Lys Met Lys Glu Ala Leu
                725                 730                 735

Glu Asn Gln Ala Glu Ala Thr Lys Ala Ile Ile Asn Tyr Gln Tyr Asn
                740                 745                 750

Gln Tyr Thr Glu Glu Lys Asn Asn Ile Asn Phe Asn Ile Asp Asp
                755                 760                 765

Leu Ser Ser Lys Leu Asn Glu Ser Ile Asn Lys Ala Met Ile Asn Ile
        770                 775                 780

Asn Lys Phe Leu Asn Gln Cys Ser Val Ser Tyr Leu Met Asn Ser Met
785                 790                 795                 800

Ile Pro Tyr Gly Val Lys Arg Leu Glu Asp Phe Asp Ala Ser Leu Lys
                805                 810                 815

Asp Ala Leu Leu Lys Tyr Ile Tyr Asp Asn Arg Gly Thr Leu Ile Gly
                820                 825                 830

Gln Val Asp Arg Leu Lys Asp Lys Val Asn Asn Thr Leu Ser Arg Asp
                835                 840                 845

Arg Pro Phe Gln Leu Ser Lys Tyr Val Asp Asn Gln Arg Leu Leu Ser
        850                 855                 860

Thr Phe Thr Glu Tyr Ile Lys Asn Ile Ile Asn Thr Ser Ile Leu Asn
865                 870                 875                 880

Leu Arg Tyr Glu Ser Asn His Leu Ile Asp Leu Ser Arg Tyr Ala Ser
                885                 890                 895

Lys Ile Asn Ile Gly Ser Lys Val Asn Phe Asp Pro Ile Asp Lys Asn
                900                 905                 910

Gln Ile Gln Leu Phe Asn Leu Glu Ser Ser Lys Ile Glu Val Ile Leu
        915                 920                 925

Lys Asn Ala Ile Val Tyr Asn Ser Met Tyr Glu Asn Phe Ser Thr Ser
        930                 935                 940

Phe Trp Ile Arg Ile Pro Lys Tyr Phe Asn Ser Ile Ser Leu Asn Asn
945                 950                 955                 960

Glu Tyr Thr Ile Ile Asn Cys Met Glu Asn Asn Ser Gly Trp Lys Val
                965                 970                 975

Ser Leu Asn Tyr Gly Glu Ile Ile Trp Thr Leu Gln Asp Thr Gln Glu
                980                 985                 990

Ile Lys Gln Arg Val Val Phe Lys Tyr Ser Gln Met Ile Asn Ile Ser
        995                 1000                1005

Asp Tyr Ile Asn Arg Trp Ile Phe Val Thr Ile Thr Asn Asn Arg
        1010                1015                1020

Leu Asn Asn Ser Lys Ile Tyr Ile Asn Gly Arg Leu Ile Asp Gln
        1025                1030                1035

Lys Pro Ile Ser Asn Leu Gly Asn Ile His Ala Ser Asn Asn Ile
        1040                1045                1050

Met Phe Lys Leu Asp Gly Cys Arg Asp Thr His Arg Tyr Ile Trp
        1055                1060                1065

Ile Lys Tyr Phe Asn Leu Phe Asp Lys Glu Leu Asn Glu Lys Glu
        1070                1075                1080
```

| Ile | Lys | Asp | Leu | Tyr | Asp | Asn | Gln | Ser | Asn | Ser | Gly | Ile | Leu | Lys |
|     |     |     |     |     |     |     |     |     |     |     |     |     |     |     |
| 1085 |     |     |     |     | 1090 |     |     |     |     | 1095 |     |     |     |     |

| Asp | Phe | Trp | Gly | Asp | Tyr | Leu | Gln | Tyr | Asp | Lys | Pro | Tyr | Tyr | Met |
| 1100 |     |     |     |     | 1105 |     |     |     |     | 1110 |     |     |     |     |

| Leu | Asn | Leu | Tyr | Asp | Pro | Asn | Lys | Tyr | Val | Asp | Val | Asn | Asn | Val |
| 1115 |     |     |     |     | 1120 |     |     |     |     | 1125 |     |     |     |     |

| Gly | Ile | Arg | Gly | Tyr | Met | Tyr | Leu | Lys | Gly | Pro | Arg | Gly | Ser | Val |
| 1130 |     |     |     |     | 1135 |     |     |     |     | 1140 |     |     |     |     |

| Met | Thr | Thr | Asn | Ile | Tyr | Leu | Asn | Ser | Ser | Leu | Tyr | Arg | Gly | Thr |
| 1145 |     |     |     |     | 1150 |     |     |     |     | 1155 |     |     |     |     |

| Lys | Phe | Ile | Ile | Lys | Tyr | Ala | Ser | Gly | Asn | Lys | Asp | Asn | Ile |     |
| 1160 |     |     |     |     | 1165 |     |     |     |     | 1170 |     |     |     |     |

| Val | Arg | Asn | Asn | Asp | Arg | Val | Tyr | Ile | Asn | Val | Val | Lys | Asn |     |
| 1175 |     |     |     |     | 1180 |     |     |     |     | 1185 |     |     |     |     |

| Lys | Glu | Tyr | Arg | Leu | Ala | Thr | Asn | Ala | Ser | Gln | Ala | Gly | Val | Glu |
| 1190 |     |     |     |     | 1195 |     |     |     |     | 1200 |     |     |     |     |

| Lys | Ile | Leu | Ser | Ala | Leu | Glu | Ile | Pro | Asp | Val | Gly | Asn | Leu | Ser |
| 1205 |     |     |     |     | 1210 |     |     |     |     | 1215 |     |     |     |     |

| Gln | Val | Val | Val | Met | Lys | Ser | Lys | Asn | Asp | Gln | Gly | Ile | Thr | Asn |
| 1220 |     |     |     |     | 1225 |     |     |     |     | 1230 |     |     |     |     |

| Lys | Cys | Lys | Met | Asn | Leu | Gln | Asp | Asn | Asn | Gly | Asn | Asp | Ile | Gly |
| 1235 |     |     |     |     | 1240 |     |     |     |     | 1245 |     |     |     |     |

| Phe | Ile | Gly | Phe | His | Gln | Phe | Asn | Asn | Ile | Ala | Lys | Leu | Val | Ala |
| 1250 |     |     |     |     | 1255 |     |     |     |     | 1260 |     |     |     |     |

| Ser | Asn | Trp | Tyr | Asn | Arg | Gln | Ile | Glu | Arg | Ser | Ser | Arg | Thr | Leu |
| 1265 |     |     |     |     | 1270 |     |     |     |     | 1275 |     |     |     |     |

| Gly | Cys | Ser | Trp | Glu | Phe | Ile | Pro | Val | Asp | Asp | Gly | Trp | Gly | Glu |
| 1280 |     |     |     |     | 1285 |     |     |     |     | 1290 |     |     |     |     |

| Arg | Pro | Leu |
| 1295 |     |     |

```
<210> SEQ ID NO 2
<211> LENGTH: 3888
<212> TYPE: DNA
<213> ORGANISM: Artificial sequence
<220> FEATURE:
<223> OTHER INFORMATION: Engineered BoNT/A

<400> SEQUENCE: 2
atgccattcg tcaacaagca attcaactac aaagacccag tcaacggcgt cgacatcgca      60
tacatcaaga ttccgaacgc cggtcaaatg cagccggtta aggcttttaa gatccacaac     120
aagatttggg ttatcccgga gcgtgacacc ttcacgaacc cggaagaagg cgatctgaac     180
ccgccaccgg aagcgaagca agtccctgtc agctactacg attcgacgta cctgagcacg     240
gataacgaaa agataactac cctgaaaggt gtgaccaagc tgttcgaacg tatctacagc     300
acggatctgg tcgcatgct gctgactagc attgttcgcg gtatcccgtt ctggggtggt     360
agcacgattg acaccgaact gaaggttatc gacactaact gcattaacgt tattcaaccg     420
gatggtagct atcgtagcga agagctgaat ctggtcatca ttggcccgag cgcagacatt     480
atccaattcg agtgcaagag ctttggtcac gaggttctga atctgacccg caatggctat     540
ggtagcaccc agtacattcg tttttcgccg gattttacct tcggctttga agagagcctg     600
gaggttgata ccaatccgtt gctgggtgcg ggcaaattcg ctaccgatcc ggctgtcacg     660
ctggcccatg aactgatcca cgcaggccac cgcctgtacg gcattgccat caacccaaac     720
```

| | |
|---|---|
| cgtgtgttca aggttaatac gaatgcatac tacgagatga gcggcctgga agtcagcttc | 780 |
| gaagaactgc gcaccttcgg tggccatgac gctaaattca ttgacagctt gcaagagaat | 840 |
| gagttccgtc tgtactacta taacaaattc aaagacattg caagcacgtt gaacaaggcc | 900 |
| aaaagcatcg ttggtactac cgcgtcgttg cagtatatga agaatgtgtt taaagagaag | 960 |
| tacctgctgt ccgaggatac ctccggcaag tttagcgttg ataagctgaa gtttgacaaa | 1020 |
| ctgtacaaga tgctgaccga gatttacacc gaggacaact ttgtgaaatt cttcaaagtg | 1080 |
| ttgaatcgta aaacctatct gaattttgac aaagcggttt tcaagattaa catcgtgccg | 1140 |
| aaggtgaact acaccatcta tgacggtttt aacctgcgta acaccaacct ggcggcgaac | 1200 |
| tttaacggtc agaatacgga aatcaacaac atgaatttca cgaagttgaa gaacttcacg | 1260 |
| ggtctgttcg agttctataa gctgctgtgc gtgcgcggta tcatcaccag caaaaccaaa | 1320 |
| agcctggaca aaggctacaa caaggcgctg aatgacctgt gcattaaggt aaacaattgg | 1380 |
| gatctgttct tttcgccatc cgaagataat tttaccaacg acctgaacaa gggtgaagaa | 1440 |
| atcaccagcg atacgaatat tgaagcagcg gaagagaata tcagcctgga tctgatccag | 1500 |
| cagtactatc tgacctttaa cttcgacaat gaaccggaga acattagcat gagaatctg | 1560 |
| agcagcgaca ttatcggtca gctggaactg atgccgaata tcgaacgttt cccgaacggc | 1620 |
| aaaaagtacg agctggacaa gtacactatg ttccattacc tgcgtgcaca ggagtttgaa | 1680 |
| cacggtaaac gtcgtatcgc gctgaccaac agcgttaacg aggccctgct gaacccgagc | 1740 |
| cgtgtctata ccttcttcag cagcgactat gttaagaaag tgaacaaagc cactgaggcc | 1800 |
| gcgatgttcc tgggctgggt ggaacagctg gtatatgact tcacggacga gacgagcgaa | 1860 |
| gtgagcacta ccgacaaaat tgctgatatt accatcatta tcccgtatat tggtccggca | 1920 |
| ctgaacattg caacatgcg ttacaaacgt cgttttgtgg gtgccctgat cttctccggt | 1980 |
| gccgtgattc tgctggagtt cattccggag attgcgatcc cggtgttggg taccttcgcg | 2040 |
| ctggtgtcct acatcgcgaa taaggttctg acggttcaga ccatcgataa cgcgctgtcg | 2100 |
| aaacgtaatg aaaaatggga cgaggtttac aaatacattg ttacgaattg gctggcgaaa | 2160 |
| gtcaataccc agatcgacct gatccgtaag aaaatgaaag aggcgctgga gaatcaggcg | 2220 |
| gaggccacca agcaattat caactaccaa tacaaccagt acacggaaga agagaagaat | 2280 |
| aacattaact tcaatatcga tgatttgagc agcaagctga atgaatctat caacaaagcg | 2340 |
| atgatcaata tcaacaagtt tttgaatcag tgtagcgttt cgtacctgat gaatagcatg | 2400 |
| attccgtatg gcgtcaaacg tctggaggac ttcgacgcca gcctgaaaga tgcgttgctg | 2460 |
| aaatacattt acgacaatcg tggtacgctg attggccaag ttgaccgctt gaaagacaaa | 2520 |
| gttaacaata ccctgagccg tgaccgtcca tttcaactga gcaagtatgt tgataatcaa | 2580 |
| cgtctgttga gcactttcac cgagtatatc aaaaacatca tcaatactag cattctgaac | 2640 |
| ctgcgttacg agagcaatca tctgattgat ctgagccgtt atgcaagcaa gatcaacatc | 2700 |
| ggtagcaagg tcaattttga cccgatcgat aagaaccaga tccagctgtt taatctggaa | 2760 |
| tcgagcaaaa ttgaggttat cctgaaaaac gccattgtct acaactccat gtacgagaat | 2820 |
| ttctccacca gcttctggat tcgcatcccg aaatacttca acagcattag cctgaacaac | 2880 |
| gagtatacta tcatcaactg tatggagaac aacagcggtt ggaaggtgtc tctgaactat | 2940 |
| ggtgagatca tttggacctt gcaggacacc aagagatca agcagcgcgt cgtgttcaag | 3000 |
| tactctcaaa tgatcaacat ttccgattac attaatcgtt ggatcttcgt gaccattacg | 3060 |
| aataaccgtc tgaataacag caagatttac atcaatggtc gcttgatcga tcagaaaccg | 3120 |

```
attagcaacc tgggtaatat ccacgcaagc aacaacatta tgttcaaatt ggacggttgc    3180
cgcgataccc atcgttatat ctggatcaag tatttcaacc tgtttgataa agaactgaat    3240
gagaaggaga tcaaagattt gtatgacaac caatctaaca gcggcatttt gaaggacttc    3300
tggggcgatt atctgcaata cgataagccg tactatatgc tgaacctgta tgatccgaac    3360
aaatatgtgg atgtcaataa tgtgggtatt cgtggttaca tgtatttgaa gggtccgcgt    3420
ggcagcgtta tgacgaccaa catttacctg aactctagcc tgtaccgtgg tacgaaattc    3480
atcattaaga aatatgccag cggcaacaaa gataacattg tgcgtaataa cgatcgtgtc    3540
tacatcaacg tggtcgtgaa gaataaagag taccgtctgg cgaccaacgc ttcgcaggcg    3600
ggtgttgaga aaattctgag cgcgttggag atccctgatg tcggtaatct gagccaagtc    3660
gtggttatga agagcaagaa cgaccagggt atcactaaca agtgcaagat gaacctgcaa    3720
gacaacaatg gtaacgacat cggctttatt ggtttccacc agttcaacaa tattgctaaa    3780
ctggtagcga gcaattggta caatcgtcag attgagcgca gcagccgtac tttgggctgt    3840
agctgggagt ttatcccggt cgatgatggt tggggcgaac gtccgctg               3888
```

<210> SEQ ID NO 3
<211> LENGTH: 1296
<212> TYPE: PRT
<213> ORGANISM: Artificial sequence
<220> FEATURE:
<223> OTHER INFORMATION: Engineered BoNT/A

<400> SEQUENCE: 3

```
Met Pro Phe Val Asn Lys Gln Phe Asn Tyr Lys Asp Pro Val Asn Gly
1               5                   10                  15

Val Asp Ile Ala Tyr Ile Lys Ile Pro Asn Ala Gly Gln Met Gln Pro
            20                  25                  30

Val Lys Ala Phe Lys Ile His Asn Lys Ile Trp Val Ile Pro Glu Arg
        35                  40                  45

Asp Thr Phe Thr Asn Pro Glu Glu Gly Asp Leu Asn Pro Pro Pro Glu
    50                  55                  60

Ala Lys Gln Val Pro Val Ser Tyr Tyr Asp Ser Thr Tyr Leu Ser Thr
65                  70                  75                  80

Asp Asn Glu Lys Asp Asn Tyr Leu Lys Gly Val Thr Lys Leu Phe Glu
                85                  90                  95

Arg Ile Tyr Ser Thr Asp Leu Gly Arg Met Leu Leu Thr Ser Ile Val
            100                 105                 110

Arg Gly Ile Pro Phe Trp Gly Gly Ser Thr Ile Asp Thr Glu Leu Lys
        115                 120                 125

Val Ile Asp Thr Asn Cys Ile Asn Val Ile Gln Pro Asp Gly Ser Tyr
    130                 135                 140

Arg Ser Glu Glu Leu Asn Leu Val Ile Gly Pro Ser Ala Asp Ile
145                 150                 155                 160

Ile Gln Phe Glu Cys Lys Ser Phe Gly His Glu Val Leu Asn Leu Thr
                165                 170                 175

Arg Asn Gly Tyr Gly Ser Thr Gln Tyr Ile Arg Phe Ser Pro Asp Phe
            180                 185                 190

Thr Phe Gly Phe Glu Glu Ser Leu Glu Val Asp Thr Asn Pro Leu Leu
        195                 200                 205

Gly Ala Gly Lys Phe Ala Thr Asp Pro Ala Val Thr Leu Ala His Glu
    210                 215                 220
```

-continued

```
Leu Ile His Ala Gly His Arg Leu Tyr Gly Ile Ala Ile Asn Pro Asn
225                 230                 235                 240

Arg Val Phe Lys Val Asn Thr Asn Ala Tyr Tyr Glu Met Ser Gly Leu
            245                 250                 255

Glu Val Ser Phe Glu Glu Leu Arg Thr Phe Gly Gly His Asp Ala Lys
        260                 265                 270

Phe Ile Asp Ser Leu Gln Glu Asn Glu Phe Arg Leu Tyr Tyr Tyr Asn
    275                 280                 285

Lys Phe Lys Asp Ile Ala Ser Thr Leu Asn Lys Ala Lys Ser Ile Val
290                 295                 300

Gly Thr Thr Ala Ser Leu Gln Tyr Met Lys Asn Val Phe Lys Glu Lys
305                 310                 315                 320

Tyr Leu Leu Ser Glu Asp Thr Ser Gly Lys Phe Ser Val Asp Lys Leu
            325                 330                 335

Lys Phe Asp Lys Leu Tyr Lys Met Leu Thr Glu Ile Tyr Thr Glu Asp
        340                 345                 350

Asn Phe Val Lys Phe Phe Lys Val Leu Asn Arg Lys Thr Tyr Leu Asn
    355                 360                 365

Phe Asp Lys Ala Val Phe Lys Ile Asn Ile Val Pro Lys Val Asn Tyr
370                 375                 380

Thr Ile Tyr Asp Gly Phe Asn Leu Arg Asn Thr Asn Leu Ala Ala Asn
385                 390                 395                 400

Phe Asn Gly Gln Asn Thr Glu Ile Asn Asn Met Asn Phe Thr Lys Leu
            405                 410                 415

Lys Asn Phe Thr Gly Leu Phe Glu Phe Tyr Lys Leu Leu Cys Val Arg
        420                 425                 430

Gly Ile Ile Thr Ser Lys Thr Lys Ser Leu Asp Lys Gly Tyr Asn Lys
    435                 440                 445

Ala Leu Asn Asp Leu Cys Ile Lys Val Asn Asn Trp Asp Leu Phe Phe
450                 455                 460

Ser Pro Ser Glu Asp Asn Phe Thr Asn Asp Leu Lys Lys Gly Glu Glu
465                 470                 475                 480

Ile Thr Ser Asp Thr Asn Ile Glu Ala Ala Glu Glu Asn Ile Ser Leu
            485                 490                 495

Asp Leu Ile Gln Gln Tyr Tyr Leu Thr Phe Asn Phe Asp Asn Glu Pro
        500                 505                 510

Glu Asn Ile Ser Ile Glu Asn Leu Ser Ser Asp Ile Ile Gly Gln Leu
    515                 520                 525

Glu Leu Met Pro Asn Ile Glu Arg Phe Pro Asn Gly Lys Lys Tyr Glu
530                 535                 540

Leu Asp Lys Tyr Thr Met Phe His Tyr Leu Arg Ala Gln Glu Phe Glu
545                 550                 555                 560

His Gly Lys Ser Arg Ile Ala Leu Thr Asn Ser Val Asn Glu Ala Leu
            565                 570                 575

Leu Asn Pro Ser Arg Val Tyr Thr Phe Phe Ser Ser Asp Tyr Val Lys
        580                 585                 590

Lys Val Asn Lys Ala Thr Lys Ala Ala Met Phe Leu Gly Trp Val Glu
    595                 600                 605

Gln Leu Val Tyr Asp Phe Thr Asp Glu Thr Ser Glu Val Ser Thr Thr
610                 615                 620

Asp Lys Ile Ala Asp Ile Thr Ile Ile Pro Tyr Ile Gly Pro Ala
625                 630                 635                 640

Leu Asn Ile Gly Asn Met Leu Tyr Lys Asp Asp Phe Val Gly Ala Leu
```

```
                    645                 650                 655
Ile Phe Ser Gly Ala Val Ile Leu Leu Glu Phe Ile Pro Glu Ile Ala
                660                 665                 670

Ile Pro Val Leu Gly Thr Phe Ala Leu Val Ser Tyr Ile Ala Lys Lys
                675                 680                 685

Val Leu Thr Val Gln Thr Ile Asp Asn Ala Leu Ser Lys Arg Asn Glu
                690                 695                 700

Lys Trp Asp Glu Val Tyr Lys Tyr Ile Val Thr Asn Trp Leu Ala Lys
705                 710                 715                 720

Val Asn Thr Gln Ile Asp Leu Ile Arg Lys Lys Met Lys Glu Ala Leu
                725                 730                 735

Glu Asn Gln Ala Glu Ala Thr Lys Ala Ile Ile Asn Tyr Gln Tyr Asn
                740                 745                 750

Gln Tyr Thr Glu Glu Glu Lys Asn Lys Ile Lys Phe Asn Ile Asp Asp
                755                 760                 765

Leu Ser Ser Lys Leu Asn Glu Ser Ile Asn Lys Ala Met Ile Asn Ile
                770                 775                 780

Asn Lys Phe Leu Asn Gln Cys Ser Val Ser Tyr Leu Met Asn Ser Met
785                 790                 795                 800

Ile Pro Tyr Gly Val Lys Arg Leu Glu Asp Phe Asp Ala Ser Leu Lys
                805                 810                 815

Asp Ala Leu Leu Lys Tyr Ile Tyr Asp Asn Arg Gly Thr Leu Lys Gly
                820                 825                 830

Gln Val Asp Arg Leu Lys Asp Lys Val Asn Asn Thr Leu Ser Thr Asp
                835                 840                 845

Ile Pro Phe Gln Leu Ser Lys Tyr Val Asp Asn Gln Arg Leu Leu Ser
850                 855                 860

Thr Phe Thr Glu Tyr Ile Lys Asn Ile Ile Asn Thr Ser Ile Leu Asn
865                 870                 875                 880

Leu Arg Tyr Glu Ser Asn His Leu Ile Asp Leu Ser Arg Tyr Ala Ser
                885                 890                 895

Lys Ile Asn Ile Gly Ser Lys Val Asn Phe Asp Pro Ile Asp Lys Asn
                900                 905                 910

Gln Ile Gln Leu Phe Asn Leu Glu Ser Ser Lys Ile Glu Val Ile Leu
                915                 920                 925

Lys Asn Ala Ile Val Tyr Asn Ser Met Tyr Glu Asn Phe Ser Thr Ser
930                 935                 940

Phe Trp Ile Arg Ile Pro Lys Tyr Phe Asn Ser Ile Ser Leu Asn Asn
945                 950                 955                 960

Glu Tyr Thr Ile Ile Asn Cys Met Glu Asn Asn Ser Gly Trp Lys Val
                965                 970                 975

Ser Leu Asn Tyr Gly Glu Ile Ile Trp Thr Leu Gln Asp Thr Gln Glu
                980                 985                 990

Ile Lys Gln Arg Val Val Phe Lys Tyr Ser Gln Met Ile Asn Ile Ser
                995                 1000                1005

Asp Tyr Ile Asn Arg Trp Ile Phe Val Thr Ile Thr Asn Asn Arg
                1010                1015                1020

Leu Asn Asn Ser Lys Ile Tyr Ile Asn Gly Arg Leu Ile Asp Gln
                1025                1030                1035

Lys Pro Ile Ser Asn Leu Gly Asn Ile His Ala Ser Asn Asn Ile
                1040                1045                1050

Met Phe Lys Leu Asp Gly Cys Arg Asp Thr His Arg Tyr Ile Trp
                1055                1060                1065
```

Ile Lys Tyr Phe Asn Leu Phe Asp Lys Glu Leu Asn Glu Lys Glu
    1070              1075                1080

Ile Lys Asp Leu Tyr Asp Asn Gln Ser Asn Ser Gly Ile Leu Lys
    1085              1090                1095

Asp Phe Trp Gly Asp Tyr Leu Gln Tyr Asp Lys Pro Tyr Tyr Met
    1100              1105                1110

Leu Asn Leu Tyr Asp Pro Asn Lys Tyr Val Asp Val Asn Asn Val
    1115              1120                1125

Gly Ile Arg Gly Tyr Met Tyr Leu Lys Gly Pro Arg Gly Ser Val
    1130              1135                1140

Met Thr Thr Asn Ile Tyr Leu Asn Ser Ser Leu Tyr Arg Gly Thr
    1145              1150                1155

Lys Phe Ile Ile Lys Lys Tyr Ala Ser Gly Asn Lys Asp Asn Ile
    1160              1165                1170

Val Arg Asn Asn Asp Arg Val Tyr Ile Asn Val Val Val Lys Asn
    1175              1180                1185

Lys Glu Tyr Arg Leu Ala Thr Asn Ala Ser Gln Ala Gly Val Glu
    1190              1195                1200

Lys Ile Leu Ser Ala Leu Glu Ile Pro Asp Val Gly Asn Leu Ser
    1205              1210                1215

Gln Val Val Val Met Lys Ser Lys Asn Asp Gln Gly Ile Thr Asn
    1220              1225                1230

Lys Cys Lys Met Asn Leu Gln Asp Asn Asn Gly Asn Asp Ile Gly
    1235              1240                1245

Phe Ile Gly Phe His Gln Phe Asn Asn Ile Ala Lys Leu Val Ala
    1250              1255                1260

Ser Asn Trp Tyr Asn Arg Gln Ile Glu Arg Ser Ser Arg Thr Leu
    1265              1270                1275

Gly Cys Ser Trp Glu Phe Ile Pro Val Asp Asp Gly Trp Gly Glu
    1280              1285                1290

Arg Pro Leu
    1295

<210> SEQ ID NO 4
<211> LENGTH: 3888
<212> TYPE: DNA
<213> ORGANISM: Artificial sequence
<220> FEATURE:
<223> OTHER INFORMATION: Engineered BoNT/A

<400> SEQUENCE: 4
atgccattcg tcaacaagca attcaactac aaagacccag tcaacggcgt cgacatcgca    60
tacatcaaga ttccgaacgc cggtcaaatg cagccggtta aggcttttaa gatccacaac   120
aagatttggg ttatcccgga gcgtgacacc ttcacgaacc cggaagaagg cgatctgaac   180
ccgccaccgg aagcgaagca agtccctgtc agctactacg attcgacgta cctgagcacg   240
gataacgaaa agataacta cctgaaaggt gtgaccaagc tgttcgaacg tatctacagc   300
acggatctgg tcgcatgct gctgactagc attgttcgcg gtatcccgtt ctggggtggt   360
agcacgattg acaccgaact gaaggttatc gacactaact gcattaacgt tattcaaccg   420
gatggtagct atcgtagcga agagctgaat ctggtcatca ttggcccgag cgcagacatt   480
atccaattcg agtgcaagag ctttggtcac gaggttctga atctgacccg caatggctat   540
ggtagcaccc agtacattcg ttttttcgcc gatttacct tcggctttga agagagcctg   600

```
gaggttgata ccaatccgtt gctgggtgcg gcaaattcg ctaccgatcc ggctgtcacg      660
ctggcccatg aactgatcca cgcaggccac cgcctgtacg gcattgccat caacccaaac    720
cgtgtgttca aggttaatac gaatgcatac tacgagatga gcggcctgga agtcagcttc    780
gaagaactgc gcaccttcgg tggccatgac gctaaattca ttgacagctt gcaagagaat    840
gagttccgtc tgtactacta aacaaattc aaagacattg caagcacgtt gaacaaggcc     900
aaaagcatcg ttggtactac cgcgtcgttg cagtatatga agaatgtgtt taaagagaag    960
tacctgctgt ccgaggatac ctccggcaag tttagcgttg ataagctgaa gtttgacaaa    1020
ctgtacaaga tgctgaccga gatttacacc gaggacaact ttgtgaaatt cttcaaagtg    1080
ttgaatcgta aaacctatct gaattttgac aaagcggttt tcaagattaa catcgtgccg    1140
aaggtgaact acaccatcta tgacggtttt aacctgcgta acaccaacct ggcggcgaac    1200
tttaacggtc agaatacgga aatcaacaac atgaatttca cgaagttgaa gaacttcacg    1260
ggtctgttcg agttctataa gctgctgtgc gtgcgcggta tcatcaccag caaaaccaaa    1320
agcctggaca aaggctacaa caaggcgctg aatgacctgt gcattaaggt aaacaattgg    1380
gatctgttct tttcgccatc cgaagataat tttaccaacg acctgaagaa gggtgaagaa    1440
atcaccagcg atacgaatat tgaagcagcg gaagagaata tcagcctgga tctgatccag    1500
cagtactatc tgacctttaa cttcgacaat gaaccggaga acattagcat tgagaatctg    1560
agcagcgaca ttatcggtca gctggaactg atgccgaata tcgaacgttt cccgaacggc    1620
aaaaagtacg agctggacaa gtacactatg ttccattacc tgcgtgcaca ggagttttgaa   1680
cacggtaaaa gccgtatcgc gctgaccaac agcgttaacg aggccctgct gaacccgagc    1740
cgtgtctata ccttcttcag cagcgactat gttaagaaag tgaacaaagc cactaaggcc    1800
gcgatgttcc tgggctgggt ggaacagctg gtatatgact tcacgacga gacgagcgaa    1860
gtgagcacta ccgacaaaat tgctgatatt accatcatta tcccgtatat tggtccggca    1920
ctgaacattg caacatgct gtacaaagac gattttgtgg gtgccctgat cttctccggt      1980
gccgtgattc tgctggagtt cattccggag attgcgatcc cggtgttggg taccttcgcg    2040
ctggtgtcct acatcgcgaa gaaggttctg acggttcaga ccatcgataa cgcgctgtcg    2100
aaacgtaatg aaaaatggga cgaggtttac aaatacattg ttacgaattg gctggcgaaa    2160
gtcaataccc agatcgacct gatccgtaag aaaatgaaag aggcgctgga gaatcaggcg    2220
gaggccacca agcaattat caactaccaa tacaaccagt acacggaaga agagaagaat      2280
aagattaagt tcaatatcga tgatttgagc agcaagctga atgaatctat caacaaagcg    2340
atgatcaata tcaacaagtt tttgaatcag tgtagcgttt cgtacctgat gaatagcatg    2400
attccgtatg gcgtcaaacg tctggaggac ttcgacgcca gcctgaaaga tgcgttgctg    2460
aaatacattt acgacaatcg tggtacgctg aagggccaag ttgaccgctt gaaagacaaa    2520
gttaacaata ccctgagcac cgacatccca tttcaactga gcaagtatgt tgataatcaa    2580
cgtctgttga gcactttcac cgagtatatc aaaaacatca tcaatactag cattctgaac    2640
ctgcgttacg agagcaatca tctgattgat ctgagccgtt atgcaagcaa gatcaacatc    2700
ggtagcaagg tcaattttga cccgatcgat aagaaccaga tccagctgtt taatctggaa    2760
tcgagcaaaa ttgaggttat cctgaaaaac gccattgtct acaactccat gtacgagaat    2820
ttctccacca gcttctggat tcgcatcccg aaatacttca acagcattag cctgaacaac    2880
gagtatacta tcatcaactg tatggagaac aacagcggtt ggaaggtgtc tctgaactat    2940
ggtgagatca tttggaccct tgcaggacacc caagagatca agcagcgcgt cgtgttcaag    3000
```

```
tactctcaaa tgatcaacat ttccgattac attaatcgtt ggatcttcgt gaccattacg    3060
aataaccgtc tgaataacag caagatttac atcaatggtc gcttgatcga tcagaaaccg    3120
attagcaacc tgggtaatat ccacgcaagc aacaacatta tgttcaaatt ggacggttgc    3180
cgcgataccc atcgttatat ctggatcaag tatttcaacc tgtttgataa agaactgaat    3240
gagaaggaga tcaaagattt gtatgacaac caatctaaca gcggcatttt gaaggacttc    3300
tggggcgatt atctgcaata cgataagccg tactatatgc tgaacctgta tgatccgaac    3360
aaatatgtgg atgtcaataa tgtgggtatt cgtggttaca tgtatttgaa gggtccgcgt    3420
ggcagcgtta tgacgaccaa catttacctg aactctagcc tgtaccgtgg tacgaaattc    3480
atcattaaga aatatgccag cggcaacaaa gataacattg tgcgtaataa cgatcgtgtc    3540
tacatcaacg tggtcgtgaa gaataaagag taccgtctgg cgaccaacgc ttcgcaggcg    3600
ggtgttgaga aaattctgag cgcgttggag atccctgatg tcggtaatct gagccaagtc    3660
gtggttatga gagcaagaa cgaccagggt atcactaaca agtgcaagat gaacctgcaa    3720
gacaacaatg gtaacgacat cggctttatt ggtttccacc agttcaacaa tattgctaaa    3780
ctggtagcga gcaattggta caatcgtcag attgagcgca gcagccgtac tttgggctgt    3840
agctgggagt ttatcccggt cgatgatggt tggggcgaac gtccgctg                 3888
```

<210> SEQ ID NO 5
<211> LENGTH: 1296
<212> TYPE: PRT
<213> ORGANISM: Artificial sequence
<220> FEATURE:
<223> OTHER INFORMATION: Engineered BoNT/A

<400> SEQUENCE: 5

```
Met Pro Phe Val Asn Lys Gln Phe Asn Tyr Lys Asp Pro Val Asn Gly
1               5                   10                  15

Val Asp Ile Ala Tyr Ile Lys Ile Pro Asn Ala Gly Gln Met Gln Pro
            20                  25                  30

Val Lys Ala Phe Lys Ile His Asn Lys Ile Trp Val Ile Pro Glu Arg
        35                  40                  45

Asp Thr Phe Thr Asn Pro Glu Glu Gly Asp Leu Asn Pro Pro Pro Glu
    50                  55                  60

Ala Lys Gln Val Pro Val Ser Tyr Tyr Asp Ser Thr Tyr Leu Ser Thr
65                  70                  75                  80

Asp Asn Glu Lys Asp Asn Tyr Leu Lys Gly Val Thr Lys Leu Phe Glu
                85                  90                  95

Arg Ile Tyr Ser Thr Asp Leu Gly Arg Met Leu Leu Thr Ser Ile Val
            100                 105                 110

Arg Gly Ile Pro Phe Trp Gly Gly Ser Thr Ile Asp Thr Glu Leu Lys
        115                 120                 125

Val Ile Asp Thr Asn Cys Ile Asn Val Ile Gln Pro Asp Gly Ser Tyr
    130                 135                 140

Arg Ser Glu Glu Leu Asn Leu Val Ile Gly Pro Ser Ala Asp Ile
145                 150                 155                 160

Ile Gln Phe Glu Cys Lys Ser Phe Gly His Glu Val Leu Asn Leu Thr
                165                 170                 175

Arg Asn Gly Tyr Gly Ser Thr Gln Tyr Ile Arg Phe Ser Pro Asp Phe
            180                 185                 190

Thr Phe Gly Phe Glu Glu Ser Leu Glu Val Asp Thr Asn Pro Leu Leu
        195                 200                 205
```

Gly Ala Gly Lys Phe Ala Thr Asp Pro Ala Val Thr Leu Ala His Glu
    210                 215                 220

Leu Ile His Ala Gly His Arg Leu Tyr Gly Ile Ala Ile Asn Pro Asn
225                 230                 235                 240

Arg Val Phe Lys Val Asn Thr Asn Ala Tyr Tyr Glu Met Ser Gly Leu
                245                 250                 255

Glu Val Ser Phe Glu Glu Leu Arg Thr Phe Gly Gly His Asp Ala Lys
            260                 265                 270

Phe Ile Asp Ser Leu Gln Glu Asn Glu Phe Arg Leu Tyr Tyr Tyr Asn
        275                 280                 285

Lys Phe Lys Asp Ile Ala Ser Thr Leu Asn Lys Ala Lys Ser Ile Val
290                 295                 300

Gly Thr Thr Ala Ser Leu Gln Tyr Met Lys Asn Val Phe Lys Glu Lys
305                 310                 315                 320

Tyr Leu Leu Ser Glu Asp Thr Ser Gly Lys Phe Ser Val Asp Lys Leu
                325                 330                 335

Lys Phe Asp Lys Leu Tyr Lys Met Leu Thr Glu Ile Tyr Thr Glu Asp
            340                 345                 350

Asn Phe Val Lys Phe Phe Lys Val Leu Asn Arg Lys Thr Tyr Leu Asn
        355                 360                 365

Phe Asp Lys Ala Val Phe Lys Ile Asn Ile Val Pro Lys Val Asn Tyr
370                 375                 380

Thr Ile Tyr Asp Gly Phe Asn Leu Arg Asn Thr Asn Leu Ala Ala Asn
385                 390                 395                 400

Phe Asn Gly Gln Asn Thr Glu Ile Asn Asn Met Asn Phe Thr Lys Leu
                405                 410                 415

Lys Asn Phe Thr Gly Leu Phe Glu Phe Tyr Lys Leu Leu Cys Val Arg
            420                 425                 430

Gly Ile Ile Thr Ser Lys Thr Lys Ser Leu Asp Lys Gly Tyr Asn Lys
        435                 440                 445

Ala Leu Asn Asp Leu Cys Ile Lys Val Asn Asn Trp Asp Leu Phe Phe
450                 455                 460

Ser Pro Ser Glu Asp Asn Phe Thr Asn Asp Leu Asn Lys Gly Glu Glu
465                 470                 475                 480

Ile Thr Ser Asp Thr Asn Ile Glu Ala Ala Glu Glu Asn Ile Ser Leu
                485                 490                 495

Asp Leu Ile Gln Gln Tyr Tyr Leu Thr Phe Asn Phe Asp Asn Glu Pro
            500                 505                 510

Glu Asn Ile Ser Ile Glu Asn Leu Ser Ser Asp Ile Ile Gly Gln Leu
        515                 520                 525

Glu Leu Met Pro Asn Ile Glu Arg Phe Pro Asn Gly Lys Lys Tyr Glu
530                 535                 540

Leu Asp Lys Tyr Thr Met Phe His Tyr Leu Arg Ala Gln Glu Phe Glu
545                 550                 555                 560

His Gly Lys Ser Arg Ile Ala Leu Thr Asn Ser Val Asn Glu Ala Leu
                565                 570                 575

Leu Lys Pro Ser Arg Val Tyr Thr Phe Phe Ser Ser Asp Tyr Val Lys
            580                 585                 590

Lys Val Asn Lys Ala Thr Glu Ala Ala Met Phe Leu Gly Trp Val Glu
        595                 600                 605

Gln Leu Val Tyr Asp Phe Thr Asp Glu Thr Ser Glu Val Ser Thr Thr
610                 615                 620

```
-continued

Asp Lys Ile Ala Asp Ile Thr Ile Ile Ile Pro Tyr Ile Gly Pro Ala
625                 630                 635                 640

Leu Asn Ile Gly Asn Met Leu Tyr Lys Asp Asp Phe Val Gly Ala Leu
            645                 650                 655

Ile Phe Ser Gly Ala Val Ile Leu Leu Glu Phe Ile Pro Glu Ile Ala
            660                 665                 670

Ile Pro Lys Leu Gly Thr Phe Ala Leu Val Ser Tyr Lys Ala Asn Lys
        675                 680                 685

Val Leu Thr Val Gln Thr Ile Asp Asn Ala Leu Ser Lys Arg Asn Glu
    690                 695                 700

Lys Trp Asp Glu Val Tyr Lys Tyr Ile Val Thr Asn Trp Leu Ala Lys
705                 710                 715                 720

Val Asn Thr Gln Ile Asp Leu Ile Arg Lys Lys Met Lys Glu Ala Leu
            725                 730                 735

Glu Asn Gln Ala Glu Ala Thr Lys Ala Ile Ile Asn Tyr Gln Tyr Asn
            740                 745                 750

Gln Tyr Lys Glu Lys Glu Lys Asn Asn Ile Asn Phe Asn Ile Asp Asp
        755                 760                 765

Leu Ser Ser Lys Leu Asn Glu Ser Ile Asn Lys Ala Met Ile Asn Ile
    770                 775                 780

Asn Lys Phe Leu Asn Gln Cys Ser Val Ser Tyr Leu Met Asn Ser Met
785                 790                 795                 800

Ile Pro Tyr Gly Val Lys Arg Leu Glu Asp Phe Asp Ala Ser Leu Lys
            805                 810                 815

Asp Ala Leu Leu Lys Tyr Ile Tyr Asp Asn Arg Gly Thr Leu Ile Gly
            820                 825                 830

Gln Val Asp Arg Leu Lys Asp Lys Val Asn Asn Thr Leu Ser Thr Asp
        835                 840                 845

Ile Pro Phe Gln Leu Ser Lys Tyr Val Asp Asn Gln Arg Leu Leu Ser
    850                 855                 860

Thr Phe Thr Glu Tyr Ile Lys Asn Ile Ile Asn Thr Ser Ile Leu Asn
865                 870                 875                 880

Leu Arg Tyr Glu Ser Asn His Leu Ile Asp Leu Ser Arg Tyr Ala Ser
            885                 890                 895

Lys Ile Asn Ile Gly Ser Lys Val Asn Phe Asp Pro Ile Asp Lys Asn
            900                 905                 910

Gln Ile Gln Leu Phe Asn Leu Glu Ser Ser Lys Ile Glu Val Ile Leu
        915                 920                 925

Lys Asn Ala Ile Val Tyr Asn Ser Met Tyr Glu Asn Phe Ser Thr Ser
    930                 935                 940

Phe Trp Ile Arg Ile Pro Lys Tyr Phe Asn Ser Ile Ser Leu Asn Asn
945                 950                 955                 960

Glu Tyr Thr Ile Ile Asn Cys Met Glu Asn Asn Ser Gly Trp Lys Val
            965                 970                 975

Ser Leu Asn Tyr Gly Glu Ile Ile Trp Thr Leu Gln Asp Thr Gln Glu
            980                 985                 990

Ile Lys Gln Arg Val Val Phe Lys Tyr Ser Gln Met Ile Asn Ile Ser
        995                 1000                1005

Asp Tyr Ile Asn Arg Trp Ile Phe Val Thr Ile Thr Asn Asn Arg
        1010                1015                1020

Leu Asn Asn Ser Lys Ile Tyr Ile Asn Gly Arg Leu Ile Asp Gln
        1025                1030                1035

Lys Pro Ile Ser Asn Leu Gly Asn Ile His Ala Ser Asn Asn Ile
```

```
            1040                1045                1050
Met Phe Lys Leu Asp Gly Cys Arg Asp Thr His Arg Tyr Ile Trp
        1055                1060                1065

Ile Lys Tyr Phe Asn Leu Phe Asp Lys Glu Leu Asn Glu Lys Glu
        1070                1075                1080

Ile Lys Asp Leu Tyr Asp Asn Gln Ser Asn Ser Gly Ile Leu Lys
        1085                1090                1095

Asp Phe Trp Gly Asp Tyr Leu Gln Tyr Asp Lys Pro Tyr Tyr Met
        1100                1105                1110

Leu Asn Leu Tyr Asp Pro Asn Lys Tyr Val Asp Val Asn Asn Val
        1115                1120                1125

Gly Ile Arg Gly Tyr Met Tyr Leu Lys Gly Pro Arg Gly Ser Val
        1130                1135                1140

Met Thr Thr Asn Ile Tyr Leu Asn Ser Ser Leu Tyr Arg Gly Thr
        1145                1150                1155

Lys Phe Ile Ile Lys Lys Tyr Ala Ser Gly Asn Lys Asp Asn Ile
        1160                1165                1170

Val Arg Asn Asn Asp Arg Val Tyr Ile Asn Val Val Val Lys Asn
        1175                1180                1185

Lys Glu Tyr Arg Leu Ala Thr Asn Ala Ser Gln Ala Gly Val Glu
        1190                1195                1200

Lys Ile Leu Ser Ala Leu Glu Ile Pro Asp Val Gly Asn Leu Ser
        1205                1210                1215

Gln Val Val Val Met Lys Ser Lys Asn Asp Gln Gly Ile Thr Asn
        1220                1225                1230

Lys Cys Lys Met Asn Leu Gln Asp Asn Asn Gly Asn Asp Ile Gly
        1235                1240                1245

Phe Ile Gly Phe His Gln Phe Asn Asn Ile Ala Lys Leu Val Ala
        1250                1255                1260

Ser Asn Trp Tyr Asn Arg Gln Ile Glu Arg Ser Ser Arg Thr Leu
        1265                1270                1275

Gly Cys Ser Trp Glu Phe Ile Pro Val Asp Asp Gly Trp Gly Glu
        1280                1285                1290

Arg Pro Leu
        1295

<210> SEQ ID NO 6
<211> LENGTH: 3888
<212> TYPE: DNA
<213> ORGANISM: Artificial sequence
<220> FEATURE:
<223> OTHER INFORMATION: Engineered BoNT/A

<400> SEQUENCE: 6
atgccattcg tcaacaagca attcaactac aaagacccag tcaacggcgt cgacatcgca      60
tacatcaaga ttccgaacgc cggtcaaatg cagccggtta aggcttttaa gatccacaac     120
aagatttggg ttatcccgga gcgtgacacc ttcacgaacc cggaagaagg cgatctgaac     180
ccgccaccgg aagcgaagca agtccctgtc agctactacg attcgacgta cctgagcacg     240
gataacgaaa aagataacta cctgaaaggt gtgaccaagc tgttcgaacg tatctacagc     300
acggatctgg gtcgcatgct gctgactagc attgttcgcg gtatcccgtt ctggggtggt     360
agcacgattg acaccgaact gaaggttatc gacactaact gcattaacgt tattcaaccg     420
gatggtagct atcgtagcga agagctgaat ctggtcatca ttggcccgag cgcagacatt     480
```

```
atccaattcg agtgcaagag ctttggtcac gaggttctga atctgacccg caatggctat    540
ggtagcaccc agtacattcg ttttcgccg gatttacct tcggctttga agagagcctg     600
gaggttgata ccaatccgtt gctgggtgcg ggcaaattcg ctaccgatcc ggctgtcacg    660
ctggcccatg aactgatcca cgcaggccac cgcctgtacg gcattgccat caacccaaac    720
cgtgtgttca aggttaatac gaatgcatac tacgagatga gcggcctgga agtcagcttc    780
gaagaactgc gcaccttcgg tggccatgac gctaaattca ttgacagctt gcaagagaat    840
gagttccgtc tgtactacta aacaaattc aaagacattg caagcacgtt gaacaaggcc     900
aaaagcatcg ttggtactac cgcgtcgttg cagtatatga agaatgtgtt taaagagaag    960
tacctgctgt ccgaggatac ctccggcaag tttagcgttg ataagctgaa gtttgacaaa    1020
ctgtacaaga tgctgaccga gatttacacc gaggacaact tgtgaaatt cttcaaagtg     1080 ttgaatcgta aacctatct gaattttgac aaagcggttt tcaagattaa catcgtgccg     1140
aaggtgaact acaccatcta tgacggtttt aacctgcgta acaccaacct ggcggcgaac    1200
tttaacggtc agaatacgga aatcaacaac atgaatttca cgaagttgaa gaacttcacg    1260
ggtctgttcg agttctataa gctgctgtgc gtgcgcggta tcatcaccag caaaaccaaa    1320
agcctggaca aaggctacaa caaggcgctg aatgacctgt gcattaaggt aaacaattgg    1380
gatctgttct tttcgccatc cgaagataat tttaccaacg acctgaacaa gggtgaagaa    1440
atcaccagcg atacgaatat tgaagcagcg gaagagaata tcagcctgga tctgatccag    1500
cagtactatc tgacctttaa cttcgacaat gaaccggaga acattagcat tgagaatctg    1560
agcagcgaca ttatcggtca gctggaactg atgccgaata tcgaacgttt cccgaacggc    1620
aaaaagtacg agctggacaa gtacactatg ttccattacc tgcgtgcaca ggagtttgaa    1680
cacggtaaaa gccgtatcgc gctgaccaac agcgttaacg aggccctgct gaaaccgagc    1740
cgtgtctata ccttcttcag cagcgactat gttaagaaag tgaacaaagc cactgaggcc    1800
gcgatgttcc tgggctgggt ggaacagctg gtatatgact tcacggacga gacgagcgaa    1860
gtgagcacta ccgacaaaat tgctgatatt accatcatta tcccgtatat tggtccggca    1920
ctgaacattg gcaacatgct gtacaaagac gattttgtgg gtgccctgat cttctccggt    1980
gccgtgattc tgctggagtt cattccggag attgcgatcc gaagttggg taccttcgcg     2040 ctggtgtcct acaaggcgaa taaggttctg acggttcaga ccatcgataa cgcgctgtcg    2100
aaacgtaatg aaaaatggga cgaggtttac aaatacattg ttacgaattg gctggcgaaa    2160 gtcaatacc agatcgacct gatccgtaag aaaatgaaag aggcgctgga gaatcaggcg     2220
gaggccacca agcaattat caactaccaa tacaaccagt acaaggaaaa agagaagaat     2280
aacattaact tcaatatcga tgatttgagc agcaagctga atgaatctat caacaaagcg    2340
atgatcaata tcaacaagtt tttgaatcag tgtagcgttt cgtacctgat gaatagcatg    2400
attccgtatg gcgtcaaacg tctggaggac ttcgacgcca gcctgaaaga tgcgttgctg    2460
aaatacattt acgacaatcg tggtacgctg attggccaag ttgaccgctt gaaagacaaa    2520
gttaacaata ccctgagcac cgacatccca tttcaactga gcaagtatgt tgataatcaa    2580
cgtctgttga gcactttcac cgagtatatc aaaaacatca tcaatactag cattctgaac    2640
ctgcgttacg agagcaatca tctgattgat ctgagccgtt atgcaagcaa gatcaacatc    2700
ggtagcaagg tcaattttga cccgatcgat aagaaccaga tccagctgtt taatctggaa    2760
tcgagcaaaa ttgaggttat cctgaaaaac gccattgtct acaactccat gtacgagaat    2820
ttctccacca gcttctggat tcgcatcccg aaatacttca acagcattag cctgaacaac    2880
```

```
gagtatacta tcatcaactg tatggagaac aacagcggtt ggaaggtgtc tctgaactat    2940
ggtgagatca tttggacctt gcaggacacc caagagatca agcagcgcgt cgtgttcaag    3000
tactctcaaa tgatcaacat ttccgattac attaatcgtt ggatcttcgt gaccattacg    3060
aataaccgtc tgaataacag caagatttac atcaatggtc gcttgatcga tcagaaaccg    3120
attagcaacc tgggtaatat ccacgcaagc aacaacatta tgttcaaatt ggacggttgc    3180
cgcgataccc atcgttatat ctggatcaag tatttcaacc tgtttgataa agaactgaat    3240
gagaaggaga tcaaagattt gtatgacaac caatctaaca gcggcatttt gaaggacttc    3300
tggggcgatt atctgcaata cgataagccg tactatatgc tgaacctgta tgatccgaac    3360
aaatatgtgg atgtcaataa tgtgggtatt cgtggttaca tgtatttgaa gggtccgcgt    3420
ggcagcgtta tgacgaccaa catttacctg aactctagcc tgtaccgtgg tacgaaattc    3480
atcattaaga atatgccag cggcaacaaa gataacattg tgcgtaataa cgatcgtgtc    3540
tacatcaacg tggtcgtgaa gaataaagag taccgtctgg cgaccaacgc ttcgcaggcg    3600
ggtgttgaga aaattctgag cgcgttggag atccctgatg tcggtaatct gagccaagtc    3660
gtggttatga agagcaagaa cgaccagggt atcactaaca agtgcaagat gaacctgcaa    3720
gacaacaatg gtaacgacat cggctttatt ggtttccacc agttcaacaa tattgctaaa    3780
ctggtagcga gcaattggta caatcgtcag attgagcgca gcagccgtac tttgggctgt    3840
agctgggagt ttatcccggt cgatgatggt tggggcgaac gtccgctg               3888
```

<210> SEQ ID NO 7
<211> LENGTH: 820
<212> TYPE: PRT
<213> ORGANISM: Artificial sequence
<220> FEATURE:
<223> OTHER INFORMATION: Engineered BoNT/E light chain

<400> SEQUENCE: 7

```
Met Lys Ile Glu Glu Gly Lys Leu Val Ile Trp Ile Asn Gly Asp Lys
1               5                   10                  15

Gly Tyr Asn Gly Leu Ala Glu Val Gly Lys Lys Phe Glu Lys Asp Thr
            20                  25                  30

Gly Ile Lys Val Thr Val Glu His Pro Asp Lys Leu Glu Glu Lys Phe
        35                  40                  45

Pro Gln Val Ala Ala Thr Gly Asp Gly Pro Asp Ile Ile Phe Trp Ala
    50                  55                  60

His Asp Arg Phe Gly Gly Tyr Ala Gln Ser Gly Leu Leu Ala Glu Ile
65                  70                  75                  80

Thr Pro Asp Lys Ala Phe Gln Asp Lys Leu Tyr Pro Phe Thr Trp Asp
                85                  90                  95

Ala Val Arg Tyr Asn Gly Lys Leu Ile Ala Tyr Pro Ile Ala Val Glu
            100                 105                 110

Ala Leu Ser Leu Ile Tyr Asn Lys Asp Leu Leu Pro Asn Pro Pro Lys
        115                 120                 125

Thr Trp Glu Glu Ile Pro Ala Leu Asp Lys Glu Leu Lys Ala Lys Gly
    130                 135                 140

Lys Ser Ala Leu Met Phe Asn Leu Gln Glu Pro Tyr Phe Thr Trp Pro
145                 150                 155                 160

Leu Ile Ala Ala Asp Gly Gly Tyr Ala Phe Lys Tyr Glu Asn Gly Lys
                165                 170                 175

Tyr Asp Ile Lys Asp Val Gly Val Asp Asn Ala Gly Ala Lys Ala Gly
```

```
                    180                 185                 190
Leu Thr Phe Leu Val Asp Leu Ile Lys Asn Lys His Met Asn Ala Asp
            195                 200                 205
Thr Asp Tyr Ser Ile Ala Glu Ala Ala Phe Asn Lys Gly Glu Thr Ala
            210                 215                 220
Met Thr Ile Asn Gly Pro Trp Ala Trp Ser Asn Ile Asp Thr Ser Lys
225                 230                 235                 240
Val Asn Tyr Gly Val Thr Val Leu Pro Thr Phe Lys Gly Gln Pro Ser
                245                 250                 255
Lys Pro Phe Val Gly Val Leu Ser Ala Gly Ile Asn Ala Ala Ser Pro
                260                 265                 270
Asn Lys Glu Leu Ala Lys Glu Phe Leu Glu Asn Tyr Leu Leu Thr Asp
            275                 280                 285
Glu Gly Leu Glu Ala Val Asn Lys Asp Lys Pro Leu Gly Ala Val Ala
            290                 295                 300
Leu Lys Ser Tyr Glu Glu Leu Ala Lys Asp Pro Arg Ile Ala Ala
305                 310                 315                 320
Thr Met Glu Asn Ala Gln Lys Gly Glu Ile Met Pro Asn Ile Pro Gln
                325                 330                 335
Met Ser Ala Phe Trp Tyr Ala Val Arg Thr Ala Val Ile Asn Ala Ala
                340                 345                 350
Ser Gly Arg Gln Thr Val Asp Glu Ala Leu Lys Asp Ala Gln Thr Asn
            355                 360                 365
Ser Ser Ser Asn Asn Asn Asn Asn Asn Asn Asn Asn Leu Gly Ile
            370                 375                 380
Glu Gly Arg Ile Ser Glu Phe Gly Ser Met Pro Lys Ile Asn Ser Phe
385                 390                 395                 400
Asn Tyr Asn Asp Pro Val Asn Asp Arg Thr Ile Leu Tyr Ile Lys Pro
                405                 410                 415
Gly Gly Cys Gln Glu Phe Tyr Lys Ser Phe Asn Ile Met Lys Asn Ile
                420                 425                 430
Trp Ile Ile Pro Glu Arg Asn Val Ile Gly Thr Thr Pro Gln Asp Phe
            435                 440                 445
His Pro Pro Thr Ser Leu Lys Asn Gly Asp Ser Ser Tyr Tyr Asp Pro
            450                 455                 460
Asn Tyr Leu Gln Ser Asp Glu Glu Lys Asp Arg Phe Leu Lys Ile Val
465                 470                 475                 480
Thr Lys Ile Phe Asn Arg Ile Asn Asn Asn Leu Ser Gly Gly Ile Leu
                485                 490                 495
Leu Glu Glu Leu Ser Lys Ala Asn Pro Tyr Leu Gly Asn Asp Asn Thr
            500                 505                 510
Pro Asp Asn Lys Phe His Ile Gly Asp Ala Ser Ala Val Glu Ile Lys
            515                 520                 525
Phe Ser Lys Gly Ser Gln His Ile Leu Leu Pro Asn Val Ile Ile Met
            530                 535                 540
Gly Ala Glu Pro Asp Leu Phe Glu Thr Asn Ser Ser Asn Ile Ser Leu
545                 550                 555                 560
Arg Asn Asn Tyr Met Pro Ser Asn His Gly Phe Gly Ser Ile Ala Ile
                565                 570                 575
Val Thr Phe Ser Pro Glu Tyr Ser Phe Arg Phe Asn Asp Asn Ser Ile
                580                 585                 590
Asn Glu Phe Ile Gln Asp Pro Ala Leu Thr Leu Met His Glu Leu Ile
            595                 600                 605
```

```
His Ser Leu His Gly Leu Tyr Gly Ala Lys Gly Ile Thr Thr Thr Cys
    610                 615                 620
Ile Ile Thr Gln Gln Lys Asn Pro Leu Ile Thr Asn Arg Lys Gly Ile
625                 630                 635                 640
Asn Ile Glu Glu Phe Leu Thr Phe Gly Gly Asn Asp Leu Asn Ile Ile
                645                 650                 655
Thr Val Ala Gln Tyr Asn Asp Ile Tyr Thr Asn Leu Leu Asn Asp Tyr
            660                 665                 670
Arg Lys Ile Ala Ser Lys Leu Ser Lys Val Gln Val Ser Asn Pro Gln
        675                 680                 685
Leu Asn Pro Tyr Lys Asp Ile Phe Gln Glu Lys Tyr Gly Leu Asp Lys
    690                 695                 700
Asp Ala Ser Gly Ile Tyr Ser Val Asn Ile Asn Lys Phe Asp Asp Ile
705                 710                 715                 720
Leu Lys Lys Leu Tyr Ser Phe Thr Glu Phe Asp Leu Ala Thr Lys Phe
                725                 730                 735
Gln Val Lys Cys Arg Glu Thr Tyr Ile Gly Gln Tyr Lys Tyr Phe Lys
            740                 745                 750
Leu Ser Asn Leu Leu Asn Asp Ser Ile Tyr Asn Ile Ser Glu Gly Tyr
        755                 760                 765
Asn Ile Asn Asn Leu Lys Val Asn Phe Arg Gly Gln Asn Ala Asn Leu
    770                 775                 780
Asn Pro Arg Ile Ile Lys Pro Ile Thr Gly Arg Gly Leu Val Lys Lys
785                 790                 795                 800
Ile Ile Arg Phe Ala Val Asp Lys Leu Ala Ala Ala Leu Glu His His
                805                 810                 815
His His His His
            820

<210> SEQ ID NO 8
<211> LENGTH: 2460
<212> TYPE: DNA
<213> ORGANISM: Artificial sequence
<220> FEATURE:
<223> OTHER INFORMATION: Engineered BoNT/E light chain

<400> SEQUENCE: 8
atgaaaatcg aagaaggtaa actggtaatc tggattaacg gcgataaagg ctataacggt      60
ctcgctgaag tcggtaagaa attcgagaaa gataccggaa ttaaagtcac cgttgagcat     120
ccggataaac tggaagagaa attcccacag gttgcggcaa ctggcgatgg ccctgacatt     180
atcttctggg cacacgaccg ctttggtggc tacgctcaat ctggcctgtt ggctgaaatc     240
accccggaca aagcgttcca ggacaagctg tatccgttta cctgggatgc cgtacgttac     300
aacggcaagc tgattgctta cccgatcgct gttgaagcgt tatcgctgat ttataacaaa     360
gatctgctgc cgaacccgcc aaaaacctgg gaagagatcc cggcgctgga taaagaactg     420
aaagcgaaag gtaagagcgc gctgatgttc aacctgcaag aaccgtactt cacctggccg     480
ctgattgctg ctgacggggg ttatgcgttc aagtatgaaa acggcaagta cgacattaaa     540
gacgtgggcg tggataacgc tggcgcgaaa gcgggtctga ccttcctggt tgacctgatt     600
aaaaacaaac acatgaatgc agacaccgat tactccatcg cagaagctgc ctttaataaa     660
ggcgaaacag cgatgaccat caacggcccg tgggcatggt ccaacatcga caccagcaaa     720
gtgaattatg gtgtaacggt actgccgacc ttcaagggtc aaccatccaa accgttcgtt     780
```

```
ggcgtgctga gcgcaggtat taacgccgcc agtccgaaca agagctggc aaaagagttc    840 ctcgaaaact atctgctgac tgatgaaggt ctggaagcgg ttaataaaga caaaccgctg    900
ggtgccgtag cgctgaagtc ttacgaggaa gagttggcga agatccacg tattgccgcc    960 actatggaaa acgcccagaa aggtgaaatc atgccgaaca tcccgcagat gtccgctttc   1020
tggtatgccg tgcgtactgc ggtgatcaac gccgccagcg tcgtcagac tgtcgatgaa   1080 gccctgaaag acgcgcagac taattcgagc tcgaacaaca caacaataa caataacaac   1140 aacctcggga tcgagggaag gatttcagaa ttcggatcca tgccaaaaat caacagcttt   1200
aattacaatg accctgtaaa cgatcgtacc atcctataca taaagccggg tgggtgtcaa   1260
gagttctaca aatctttcaa tattatgaag aatatatgga ttatacctga gcgtaacgtt   1320
attggtacga caccgcaaga ttttcatcca cctacttcgt tgaagaacgg tgactcttcc   1380 tattcgacc ccaattatct ccagtcggat gaagagaagg acagattcct taaaatagta   1440
accaaaatct ttaacaggat taataacaat ctatccggag gtattttgct tgaagagctt   1500
agtaaagcta atccttacct aggtaacgat aatacaccag acaacaagtt tcatataggc   1560
gatgcatccg ccgtggaaat caaatttagc aagggatcac agcatattct cttgcccaac   1620
gttattataa tggggcgga accagattta tttgaaacaa attcgagtaa tattagcctg   1680
agaaataact atatgccgtc aaaccatggg ttcggtagca tagcgatcgt tacttttct   1740 cccgaataca gttttcgctt caatgataat agtataaatg agtttatcca agaccccgca   1800
ctcacgctta tgcacgaact catacactct ttacacggcc tgtatggcgc taaggggata   1860
accactacgt gtatcattac tcagcaaaag aacccattga taacgaacag gaagggcatt   1920
aacatcgagg aatttcttac atttggaggc aacgatctga acattataac tgtcgcacag   1980
tacaatgaca tctataccaa cttactaaat gattatagaa aaatcgcttc taagttatcc   2040
aaggttcaag tctcaaaccc tcaactgaat ccgtataagg acatattcca agagaaatat   2100
ggattagaca aagacgcgtc aggaatctat tcggtaaaca ttaacaaatt cgacgatatt   2160
ttgaagaaac tttacagctt cacggagttc gacttggcca ccaaattcca ggtcaaatgc   2220
cgagagacat acatcggaca gtataagtat ttcaagctgt cgaatctcct gaatgattcc   2280
atatacaaca ttagtgaggg ttacaatata aataacctaa aggtgaattt ccgaggccaa   2340
aacgccaacc taaatccgcg catcattaaa cccatcacag acggggtt agtgaagaaa   2400 ataatccggt ttgcggtcga caagcttgcg gccgcactcg agcaccacca ccaccaccac   2460
```

<210> SEQ ID NO 9  
<211> LENGTH: 7  
<212> TYPE: PRT  
<213> ORGANISM: Artificial sequence  
<220> FEATURE:  
<223> OTHER INFORMATION: VBCCul2 recognition motif

<400> SEQUENCE: 9

Ala Leu Ala Pro Tyr Ile Pro  
1               5

<210> SEQ ID NO 10  
<211> LENGTH: 12  
<212> TYPE: PRT  
<213> ORGANISM: Artificial sequence  
<220> FEATURE:  
<223> OTHER INFORMATION: MDM2 recognition motif  
<220> FEATURE:  
<221> NAME/KEY: misc_feature  
<222> LOCATION: (1)..(2)

```
<223> OTHER INFORMATION: Xaa can be any naturally occurring amino acid
<220> FEATURE:
<221> NAME/KEY: misc_feature
<222> LOCATION: (4)..(6)
<223> OTHER INFORMATION: Xaa can be any naturally occurring amino acid
<220> FEATURE:
<221> NAME/KEY: misc_feature
<222> LOCATION: (8)..(9)
<223> OTHER INFORMATION: Xaa can be any naturally occurring amino acid
<220> FEATURE:
<221> NAME/KEY: misc_feature
<222> LOCATION: (11)..(12)
<223> OTHER INFORMATION: Xaa can be any naturally occurring amino acid

<400> SEQUENCE: 10

Xaa Xaa Phe Xaa Xaa Xaa Trp Xaa Xaa Leu Xaa Xaa
1               5                   10

<210> SEQ ID NO 11
<211> LENGTH: 9
<212> TYPE: PRT
<213> ORGANISM: Artificial sequence
<220> FEATURE:
<223> OTHER INFORMATION: MNM2 recognition sequence

<400> SEQUENCE: 11

Arg Phe Met Asp Tyr Trp Glu Gly Leu
1               5

<210> SEQ ID NO 12
<211> LENGTH: 9
<212> TYPE: PRT
<213> ORGANISM: Artificial sequence
<220> FEATURE:
<223> OTHER INFORMATION: MNM2 recognition sequence
<220> FEATURE:
<221> NAME/KEY: misc_feature
<222> LOCATION: (2)..(4)
<223> OTHER INFORMATION: Xaa can be any naturally occurring amino acid
<220> FEATURE:
<221> NAME/KEY: misc_feature
<222> LOCATION: (7)..(8)
<223> OTHER INFORMATION: Xaa can be any naturally occurring amino acid

<400> SEQUENCE: 12

Phe Xaa Xaa Xaa Leu Trp Xaa Xaa Leu
1               5

<210> SEQ ID NO 13
<211> LENGTH: 14
<212> TYPE: PRT
<213> ORGANISM: Artificial sequence
<220> FEATURE:
<223> OTHER INFORMATION: Smurf2 recognition sequence

<400> SEQUENCE: 13

Glu Leu Glu Ser Pro Pro Pro Tyr Ser Arg Tyr Pro Met
1               5                   10

<210> SEQ ID NO 14
<211> LENGTH: 7
<212> TYPE: PRT
<213> ORGANISM: Artificial sequence
<220> FEATURE:
<223> OTHER INFORMATION: RN181 recognition sequence

<400> SEQUENCE: 14

Lys Val Gly Phe Phe Lys Arg
1               5
```

```
<210> SEQ ID NO 15
<211> LENGTH: 10
<212> TYPE: PRT
<213> ORGANISM: Artificial sequence
<220> FEATURE:
<223> OTHER INFORMATION: E3alpha recognition sequence

<400> SEQUENCE: 15

Leu Leu Val Arg Gly Arg Thr Leu Val Val
1               5                   10

<210> SEQ ID NO 16
<211> LENGTH: 10
<212> TYPE: PRT
<213> ORGANISM: Artificial sequence
<220> FEATURE:
<223> OTHER INFORMATION: SCF recognition sequence

<400> SEQUENCE: 16

Asp Arg His Asp Ser Gly Leu Asp Ser Met
1               5                   10

<210> SEQ ID NO 17
<211> LENGTH: 7
<212> TYPE: PRT
<213> ORGANISM: Artificial sequence
<220> FEATURE:
<223> OTHER INFORMATION: Siah recognition sequence
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid

<400> SEQUENCE: 17

Pro Xaa Ala Xaa Val Xaa Pro
1               5

<210> SEQ ID NO 18
<211> LENGTH: 7
<212> TYPE: PRT
<213> ORGANISM: Artificial sequence
<220> FEATURE:
<223> OTHER INFORMATION: Itch recognition sequence
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (5)..(6)
<223> OTHER INFORMATION: Xaa can be any naturally occurring amino acid

<400> SEQUENCE: 18

Pro Pro Xaa Tyr Xaa Xaa Met
1               5

<210> SEQ ID NO 19
<211> LENGTH: 4
<212> TYPE: PRT
<213> ORGANISM: Artificial sequence
<220> FEATURE:
<223> OTHER INFORMATION: Nedd4-2 recognition sequence
```

```
<220> FEATURE:
<221> NAME/KEY: misc_feature
<222> LOCATION: (3)..(3)
<223> OTHER INFORMATION: Xaa can be any naturally occurring amino acid

<400> SEQUENCE: 19

Pro Pro Xaa Tyr
1

<210> SEQ ID NO 20
<211> LENGTH: 12
<212> TYPE: PRT
<213> ORGANISM: Artificial sequence
<220> FEATURE:
<223> OTHER INFORMATION: E3 ligase recognition motif

<400> SEQUENCE: 20

Glu Thr Phe Ser Asp Leu Trp Lys Leu Leu Pro Glu
1               5                   10

<210> SEQ ID NO 21
<211> LENGTH: 12
<212> TYPE: PRT
<213> ORGANISM: Artificial sequence
<220> FEATURE:
<223> OTHER INFORMATION: E3 ligase recognition motif

<400> SEQUENCE: 21

Thr Ser Phe Ala Glu Tyr Trp Asn Leu Leu Ser Pro
1               5                   10

<210> SEQ ID NO 22
<211> LENGTH: 12
<212> TYPE: PRT
<213> ORGANISM: Artificial sequence
<220> FEATURE:
<223> OTHER INFORMATION: E3 ligase recognition motif

<400> SEQUENCE: 22

Leu Thr Phe Glu His Tyr Trp Ala Gln Leu Thr Ser
1               5                   10

<210> SEQ ID NO 23
<211> LENGTH: 12
<212> TYPE: PRT
<213> ORGANISM: Artificial sequence
<220> FEATURE:
<223> OTHER INFORMATION: E3 ligase recognition motif

<400> SEQUENCE: 23

Leu Thr Phe Glu His Trp Trp Ala Gln Leu Thr Ser
1               5                   10

<210> SEQ ID NO 24
<211> LENGTH: 12
<212> TYPE: PRT
<213> ORGANISM: Artificial sequence
<220> FEATURE:
<223> OTHER INFORMATION: E3 ligase recognition motif

<400> SEQUENCE: 24

Leu Thr Phe Glu His Ser Trp Ala Gln Leu Thr Ser
1               5                   10

<210> SEQ ID NO 25
<211> LENGTH: 12
<212> TYPE: PRT
```

```
<213> ORGANISM: Artificial sequence
<220> FEATURE:
<223> OTHER INFORMATION: E3 ligase recognition motif

<400> SEQUENCE: 25

Glu Thr Phe Glu His Asn Trp Ala Gln Leu Thr Ser
1               5                   10

<210> SEQ ID NO 26
<211> LENGTH: 12
<212> TYPE: PRT
<213> ORGANISM: Artificial sequence
<220> FEATURE:
<223> OTHER INFORMATION: E3 ligase recognition motif

<400> SEQUENCE: 26

Leu Thr Phe Glu His Asn Trp Ala Gln Leu Thr Ser
1               5                   10

<210> SEQ ID NO 27
<211> LENGTH: 12
<212> TYPE: PRT
<213> ORGANISM: Artificial sequence
<220> FEATURE:
<223> OTHER INFORMATION: E3 ligase recognition motif

<400> SEQUENCE: 27

Leu Thr Phe Glu His Trp Trp Ala Ser Leu Thr Ser
1               5                   10

<210> SEQ ID NO 28
<211> LENGTH: 12
<212> TYPE: PRT
<213> ORGANISM: Artificial sequence
<220> FEATURE:
<223> OTHER INFORMATION: E3 ligase recognition motif

<400> SEQUENCE: 28

Leu Thr Phe Glu His Trp Trp Ser Ser Leu Thr Ser
1               5                   10

<210> SEQ ID NO 29
<211> LENGTH: 12
<212> TYPE: PRT
<213> ORGANISM: Artificial sequence
<220> FEATURE:
<223> OTHER INFORMATION: E3 ligase recognition motif

<400> SEQUENCE: 29

Leu Thr Phe Thr His Trp Trp Ala Gln Leu Thr Ser
1               5                   10

<210> SEQ ID NO 30
<211> LENGTH: 12
<212> TYPE: PRT
<213> ORGANISM: Artificial sequence
<220> FEATURE:
<223> OTHER INFORMATION: E3 ligase recognition motif

<400> SEQUENCE: 30

Glu Thr Phe Glu His Trp Trp Ala Gln Leu Thr Ser
1               5                   10

<210> SEQ ID NO 31
<211> LENGTH: 12
<212> TYPE: PRT
<213> ORGANISM: Artificial sequence
```

```
<220> FEATURE:
<223> OTHER INFORMATION: E3 ligase recognition motif

<400> SEQUENCE: 31

Leu Thr Phe Glu His Trp Trp Ser Gln Leu Thr Ser
1               5                   10

<210> SEQ ID NO 32
<211> LENGTH: 12
<212> TYPE: PRT
<213> ORGANISM: Artificial sequence
<220> FEATURE:
<223> OTHER INFORMATION: E3 ligase recognition motif

<400> SEQUENCE: 32

Leu Thr Phe Glu His Trp Trp Ala Gln Leu Leu Ser
1               5                   10

<210> SEQ ID NO 33
<211> LENGTH: 12
<212> TYPE: PRT
<213> ORGANISM: Artificial sequence
<220> FEATURE:
<223> OTHER INFORMATION: E3 ligase recognition motif

<400> SEQUENCE: 33

Glu Thr Phe Glu His Trp Trp Ser Gln Leu Leu Ser
1               5                   10

<210> SEQ ID NO 34
<211> LENGTH: 9
<212> TYPE: PRT
<213> ORGANISM: Artificial sequence
<220> FEATURE:
<223> OTHER INFORMATION: E3 ligase recognition motif

<400> SEQUENCE: 34

Arg Phe Met Asp Tyr Trp Glu Gly Leu
1               5

<210> SEQ ID NO 35
<211> LENGTH: 12
<212> TYPE: PRT
<213> ORGANISM: Artificial sequence
<220> FEATURE:
<223> OTHER INFORMATION: E3 ligase recognition motif

<400> SEQUENCE: 35

Met Pro Arg Phe Met Asp Tyr Trp Glu Gly Leu Asn
1               5                   10

<210> SEQ ID NO 36
<211> LENGTH: 15
<212> TYPE: PRT
<213> ORGANISM: Artificial sequence
<220> FEATURE:
<223> OTHER INFORMATION: E3 ligase recognition motif

<400> SEQUENCE: 36

Ser Gln Glu Thr Phe Ser Asp Leu Trp Lys Leu Leu Pro Glu Asn
1               5                   10                  15

<210> SEQ ID NO 37
<211> LENGTH: 12
<212> TYPE: PRT
<213> ORGANISM: Artificial sequence
<220> FEATURE:
```

```
<223> OTHER INFORMATION: E3 ligase recognition motif

<400> SEQUENCE: 37

Leu Thr Phe Glu His Asn Trp Ala Gln Leu Glu Asn
1               5                   10
```

CATIONIC NEUROTOXINS

This application is the U.S. National Phase of International Patent Application No. PCT/GB2015/050043, filed Jan. 9, 2015, the contents of which are hereby incorporated by reference in their entirety.

The present invention relates to engineered clostridial toxins comprising at least one amino acid modification, and the use of such engineered clostridial toxins in medicine and therapy.

Bacteria in the genus *Clostridia* produce highly potent and specific protein toxins, which can poison neurons and other cells to which they are delivered. Examples of such clostridial toxins include the neurotoxins produced by *C. tetani* (TeNT) and by *C. botulinum* (BoNT) serotypes A-G, as well as those produced by *C. baratii* and *C. butyricum*.

Among the clostridial toxins are some of the most potent toxins known. By way of example, botulinum neurotoxins have median lethal dose ($LD_{50}$) values for mice ranging from 0.5 to 5 ng/kg, depending on the serotype. Both tetanus and botulinum toxins act by inhibiting the function of affected neurons, specifically the release of neurotransmitters. While botulinum toxin acts at the neuromuscular junction and inhibits cholinergic transmission in the peripheral nervous system, tetanus toxin acts in the central nervous system.

In nature, clostridial toxins are synthesised as a single-chain polypeptide that is modified post-translationally by a proteolytic cleavage event to form two polypeptide chains joined together by a disulphide bond. Cleavage occurs at a specific cleavage site, often referred to as the activation site, that is located between the cysteine residues that provide the inter-chain disulphide bond. It is this di-chain form that is the active form of the toxin. The two chains are termed the heavy chain (H-chain), which has a molecular mass of approximately 100 kDa, and the light chain (L-chain), which has a molecular mass of approximately 50 kDa. The H-chain comprises an N-terminal translocation component ($H_N$ domain) and a C-terminal targeting component ($H_C$ domain). The cleavage site is located between the L-chain and the translocation domain components. Following binding of the $H_C$ domain to its target neuron and internalisation of the bound toxin into the cell via an endosome, the $H_N$ domain translocates the L-chain across the endosomal membrane and into the cytosol, and the L-chain provides a protease function (also known as a non-cytotoxic protease).

Non-cytotoxic proteases act by proteolytically cleaving intracellular transport proteins known as SNARE proteins (e.g. SNAP-25, VAMP, or Syntaxin)—see Gerald K (2002) "Cell and Molecular Biology" (4th edition) John Wiley & Sons, Inc. The acronym SNARE derives from the term Soluble NSF Attachment Receptor, where NSF means N-ethylmaleimide-Sensitive Factor. SNARE proteins are integral to intracellular vesicle fusion, and thus to secretion of molecules via vesicle transport from a cell. The protease function is a zinc-dependent endopeptidase activity and exhibits a high substrate specificity for SNARE proteins. Accordingly, once delivered to a desired target cell, the non-cytotoxic protease is capable of inhibiting cellular secretion from the target cell. The L-chain proteases of clostridial toxins are non-cytotoxic proteases that cleave SNARE proteins.

In view of the ubiquitous nature of SNARE proteins, clostridial toxins such as botulinum toxin have been successfully employed in a wide range of therapies.

By way of example, we refer to William J. Lipham, Cosmetic and Clinical Applications of Botulinum Toxin (Slack, Inc., 2004), which describes the use of clostridial toxins, such as botulinum neurotoxins (BoNTs), BoNT/A, BoNT/B, BoNT/$C_1$, BoNT/D, BoNT/E, BoNT/F and BoNT/G, and tetanus neurotoxin (TeNT), to inhibit neuronal transmission in a number of therapeutic and cosmetic or aesthetic applications—for example, marketed botulinum toxin products are currently approved as therapeutics for indications including focal spasticity, upper limb spasticity, lower limb spasticity, cervical dystonia, blepharospasm, hemifacial spasm, hyperhidrosis of the axillae, chronic migraine, neurogenic detrusor overactivity, glabellar lines, and severe lateral canthal lines. In addition, clostridial toxin therapies are described for treating neuromuscular disorders (see U.S. Pat. No. 6,872,397); for treating uterine disorders (see US 2004/0175399); for treating ulcers and gastroesophageal reflux disease (see US 2004/0086531); for treating dystonia (see U.S. Pat. No. 6,319,505); for treating eye disorders (see US 2004/0234532); for treating blepharospasm (see US 2004/0151740); for treating strabismus (see US 2004/0126396); for treating pain (see U.S. Pat. Nos. 6,869,610, 6,641,820, 6,464,986, and 6,113,915); for treating fibromyalgia (see U.S. Pat. No. 6,623,742, US 2004/0062776); for treating lower back pain (see US 2004/0037852); for treating muscle injuries (see U.S. Pat. No. 6,423,319); for treating sinus headache (see U.S. Pat. No. 6,838,434); for treating tension headache (see U.S. Pat. No. 6,776,992); for treating headache (see U.S. Pat. No. 6,458,365); for reduction of migraine headache pain (see U.S. Pat. No. 5,714,469); for treating cardiovascular diseases (see U.S. Pat. No. 6,767,544); for treating neurological disorders such as Parkinson's disease (see U.S. Pat. Nos. 6,620,415, 6,306,403); for treating neuropsychiatric disorders (see US 2004/0180061, US 2003/0211121); for treating endocrine disorders (see U.S. Pat. No. 6,827,931); for treating thyroid disorders (see U.S. Pat. No. 6,740,321); for treating cholinergic influenced sweat gland disorders (see U.S. Pat. No. 6,683,049); for treating diabetes (see U.S. Pat. Nos. 6,337,075, 6,416,765); for treating a pancreatic disorder (see U.S. Pat. Nos. 6,261,572, 6,143,306); for treating cancers such as bone tumors (see U.S. Pat. Nos. 6,565,870, 6,368,605, 6,139,845, US 2005/0031648); for treating otic disorders (see U.S. Pat. Nos. 6,358,926, 6,265,379); for treating autonomic disorders such as gastrointestinal muscle disorders and other smooth muscle dysfunction (see U.S. Pat. No. 5,437,291); for treatment of skin lesions associated with cutaneous cell-proliferative disorders (see U.S. Pat. No. 5,670,484); for management of neurogenic inflammatory disorders (see U.S. Pat. No. 6,063,768); for reducing hair loss and stimulating hair growth (see U.S. Pat. No. 6,299,893); for treating downturned mouth (see U.S. Pat. No. 6,358,917); for reducing appetite (see US 2004/40253274); for dental therapies and procedures (see US 2004/0115139); for treating neuromuscular disorders and conditions (see US 2002/0010138); for treating various disorders and conditions and associated pain (see US 2004/0013692); for treating conditions resulting from mucus hypersecretion such as asthma and COPD (see WO 00/10598); and for treating non-neuronal conditions such as inflammation, endocrine conditions, exocrine conditions, immunological conditions, cardiovascular conditions, bone conditions (see WO 01/21213). All of the above publications are hereby incorporated by reference in their entirety.

The use of non-cytotoxic proteases such as clostridial toxins (e.g. BoNTs and TeNT) in therapeutic and cosmetic treatments of humans and other mammals is anticipated to expand to an ever-widening range of diseases and ailments that can benefit from the properties of these toxins.

To avoid systemic neurological effects, many clostridial toxin therapies utilise direct administration of the clostridial toxin therapeutic to a given target site (such as a target tissue). A problem when administering clostridial toxin-based therapeutics in this fashion is the spread of toxin away from the administration site and into surrounding tissue or systemic circulation. The diffusion of toxin away from the target tissue is believed to be responsible for undesirable side effects that in extreme cases may be life threatening. This can be a particular concern when using clostridial toxin therapeutics (such as BoNT therapeutics) at high doses, concentrations and injection volumes. Adverse effects associated with this problem that have been reported for commercial BoNT/A therapeutics include asthenia, generalised muscle weakness, diplopia, ptosis, dysphagia, dysphonia, dysarthria, urinary incontinence, and breathing difficulties. Swallowing and breathing difficulties can be life threatening and there have been reported deaths related to the spread of toxin effects.

There is therefore a need in the art for clostridial toxins which have properties of increased tissue retention at the site of administration, and which accordingly exhibit a reduction in diffusion away from the administration site, as compared to known clostridial toxins.

The present invention solves the above problem by providing engineered clostridial toxins, as specified in the claims.

In one aspect, the invention provides an engineered clostridial toxin comprising at least one (for example, at least one, two or three) amino acid modification, wherein said at least one amino acid modification increases the isoelectric point (pI) of the engineered clostridial toxin to a value that is at least 0.2 (for example, at least 0.2, 0.3, 0.4, 0.5, 0.6, 0.7, 0.8, 0.9 or 1) pI units higher than the pI of an otherwise identical clostridial toxin lacking said at least one amino acid modification, and wherein said at least one amino acid modification is not located in the clostridial toxin binding domain ($H_C$ domain).

In one embodiment, "not located in the clostridial toxin binding domain ($H_C$) domain" means that said at least one amino acid modification is located in the clostridial toxin $H_N$ domain or in the clostridial toxin light chain.

In one embodiment, the invention provides an engineered clostridial toxin comprising at least one (for example, at least one, two or three) amino acid modification, wherein said at least one amino acid modification increases the isoelectric point (pI) of the engineered clostridial toxin to a value that is at least 0.2 (for example, at least 0.2, 0.3, 0.4, 0.5, 0.6, 0.7, 0.8, 0.9 or 1) pI units higher than the pI of an otherwise identical clostridial toxin lacking said at least one amino acid modification, and wherein said at least one amino acid modification is located in the clostridial toxin translocation domain ($H_N$ domain).

In another embodiment, the invention provides an engineered clostridial toxin comprising at least one (for example, at least one, two or three) amino acid modification, wherein said at least one amino acid modification increases the isoelectric point (pI) of the engineered clostridial toxin to a value that is at least 0.2 (for example, at least 0.2, 0.3, 0.4, 0.5, 0.6, 0.7, 0.8, 0.9 or 1) pI units higher than the pI of an otherwise identical clostridial toxin lacking said at least one amino acid modification, and wherein said at least one amino acid modification is located in the clostridial toxin light chain.

In one embodiment, wherein said at least one amino acid modification is located in the clostridial toxin light chain, said at least one amino acid modification does not introduce into the clostridial toxin light chain an E3 ligase recognition motif. Thus, in one embodiment, the light chain of an engineered clostridial toxin of the invention does not comprise an E3 ligase recognition motif.

As used above, the term "E3 ligase recognition motif" refers to a modification of the light chain that results in accelerated degradation of the neurotoxin polypeptide by endogenous proteasome degradation pathways present in a subject to which the neurotoxin has been applied. An "E3 ligase recognition" motif is a structural motif that allows recognition of the motif and binding to the motif by an E3 ligase (also known as an E3 ubiquitin ligase; thus, an "E3 ligase recognition motif" may also be referred to as an "E3 ubiquitin ligase recognition motif"). E3 ligase recognition motifs will be familiar to a person skilled in the art.

Examples of E3 ligase recognition motifs include the following sequences (wherein "X" may represent any of the naturally occurring amino acids):

| E3 ubiquitin ligase | Recognition motif (consensus) |
|---|---|
| VBCCul2 | ALAPYIP (SEQ ID NO: 9) |
| MDM2 | XXFXXWXXLXX (SEQ ID NO: 10) |
| MNM2 | RFMDYWEGL (SEQ ID NO: 11) |
|  | FXXXLWXXL (SEQ ID NO: 12) |
| Smurf2 | ELESPPPPYSRYPM (SEQ ID NO: 13) |
| RN181 | KVGFFKR (SEQ ID NO: 14) |
| E3alpha | LLVRGRTLVV (SEQ ID NO: 15) |
| SCF | DRHDSGLDSM (SEQ ID NO: 16) |
| Siah | PXAXVXP (SEQ ID NO: 17) |
| Itch | PPXYXXM (SEQ ID NO: 18) |
| Nedd4-2 | PPXY (SEQ ID NO: 19) |

Further examples of E3 ligase recognition motifs include: ETFSDLWKLLPE (SEQ ID NO:20), TSFAEYWNLLSP (SEQ ID NO: 21), LTFEHYWAQLTS (SEQ ID NO: 22), LTFEHWWAQLTS (SEQ ID NO: 23), LTFEHSWAQLTS (SEQ ID NO: 24), ETFEHNWAQLTS (SEQ ID NO: 25), LTFEHNWAQLTS (SEQ ID NO: 26), LTFEHWWASLTS (SEQ ID NO: 27), LTFEHWWSSLTS (SEQ ID NO: 28), LTFTHWWAQLTS (SEQ ID NO: 29), ETFEHWWAQLTS (SEQ ID NO: 30), LTFEHWWSQLTS (SEQ ID NO: 31), LTFEHWWAQLLS (SEQ ID NO: 32), ETFEHWWSQLLS (SEQ ID NO: 33), RFMDYWEGL (SEQ ID NO: 34), MPRFMDYWEGLN (SEQ ID NO: 35), SQETFSDL-WKLLPEN (SEQ ID NO: 36), and LTFEHNWAQLEN (SEQ ID NO: 37).

In one embodiment, wherein said at least one amino acid modification is located in the clostridial toxin light chain, said at least one amino acid modification does not introduce into the clostridial toxin light chain an MDM2 E3 ligase recognition motif. Thus, in one embodiment, the light chain of an engineered clostridial toxin of the invention does not comprise an MDM2 E3 ligase recognition motif.

In one embodiment, wherein said at least one amino acid modification is located in the clostridial toxin light chain, the engineered clostridial toxin does not comprise an amino acid modification at an N-terminal proline.

In one embodiment, wherein the engineered clostridial toxin is a BoNT/E, and wherein said at least one amino acid modification is located in the clostridial toxin light chain, said engineered BoNT/E does not comprise a substitution with lysine at any one of the following amino acid positions: Q53, N72, N378, N379, R394, T400.

In one embodiment, wherein the engineered clostridial toxin is a BoNT/E, and wherein said at least one amino acid modification is located in the clostridial toxin light chain, said engineered BoNT/E does not comprise a substitution with lysine at any one of the following amino acid positions: Q53, N72, N378, N379, T400.

In one embodiment, wherein the engineered clostridial toxin is a BoNT/E, and wherein said at least one amino acid modification is located in the clostridial toxin light chain, said engineered BoNT/E does not comprise a substitution with lysine at any three of the following amino acid positions: Q53, N72, N378, N379, R394, T400.

In one embodiment, wherein the engineered clostridial toxin is a BoNT/E, and wherein said at least one amino acid modification is located in the clostridial toxin light chain, said engineered BoNT/E does not comprise a substitution with lysine at any three of the following amino acid positions: Q53, N72, N378, N379, T400.

In one embodiment, optionally wherein the at least one amino acid modification is located in the clostridial toxin light chain, the engineered clostridial toxin is not a BoNT/E.

The engineered clostridial toxins of the invention do not comprise any amino acid modifications located in the clostridial toxin $H_C$ domain. Thus, in an engineered clostridial toxin of the invention, said at least one amino acid modification is not located in the clostridial toxin $H_C$ domain.

In one embodiment, wherein said at least one amino acid modification is located in the clostridial toxin light chain, said at least one amino acid modification does not comprise the substitution of an amino acid residue with a lysine residue.

In one embodiment, wherein the engineered clostridial toxin is an engineered clostridial toxin as described above, said at least one amino acid modification comprises substitution of an acidic amino acid residue or an uncharged amino acid residue with a lysine or arginine residue.

In one embodiment, wherein the engineered clostridial toxin is an engineered clostridial toxin as described above, said at least one amino acid modification comprises substitution of an acidic amino acid residue or an uncharged amino acid residue with an arginine residue.

In one embodiment, wherein the engineered clostridial toxin is an engineered clostridial toxin as described above, said at least one amino acid modification increases the pI of the engineered clostridial toxin to a value that is at least 0.4 pI units higher than the pI of an otherwise identical clostridial toxin lacking said at least one amino acid modification. In one embodiment, said at least one amino acid modification increases the pI of the engineered clostridial toxin to a value that is at least 0.5 pI units higher than the pI of an otherwise identical clostridial toxin lacking said at least one amino acid modification. In one embodiment, said at least one amino acid modification increases the pI of the engineered clostridial toxin to a value that is at least 0.6 pI units higher than the pI of an otherwise identical clostridial toxin lacking said at least one amino acid modification. In one embodiment, said at least one amino acid modification increases the pI of the engineered clostridial toxin to a value that is at least 0.8 pI units higher than the pI of an otherwise identical clostridial toxin lacking said at least one amino acid modification. In one embodiment, said at least one amino acid modification increases the pI of the engineered clostridial toxin to a value that is at least 1 pI unit higher than the pI of an otherwise identical clostridial toxin lacking said at least one amino acid modification.

In certain embodiments, the engineered clostridial toxin comprises at least 2, 3, 4, 5, 10, 15, 20, 25, 30, 35, 40, 45, 50, 55, 60, 65, 70, 75, 80, 85 or 90 amino acid modifications.

In certain embodiments, said at least one amino acid modification increases the pI of the engineered clostridial toxin to a value that is at least 2, 3, 4 or 5 pI units higher than the pI of an otherwise identical clostridial toxin lacking said at least one amino acid modification.

In certain embodiments, the engineered clostridial toxin comprises at least 3 amino acid modifications, and said at least 3 amino acid modifications increase the pI of the engineered clostridial toxin to a value that is at least 0.2 pI units higher than the pI of an otherwise identical clostridial toxin lacking said at least 3 amino acid modifications.

In certain embodiments, the engineered clostridial toxin comprises at least 5 amino acid modifications, and said at least 5 amino acid modifications increase the pI of the engineered clostridial toxin to a value that is at least 0.5 pI units higher than the pI of an otherwise identical clostridial toxin lacking said at least 5 amino acid modifications.

The present inventors have found that by increasing the pI of a clostridial toxin, for example, by at least 0.2 pI units, or 0.5 pI units, or one pI unit (through the introduction into the clostridial toxin protein of at least one amino acid modification), the resultant engineered clostridial toxin advantageously demonstrates properties of increased tissue retention and reduced diffusion away from sites of administration, while retaining abilities of target cell binding, translocation, and cleavage of target SNARE protein(s). Thus, the spread of clostridial toxin from the site of administration is significantly reduced, as compared to an otherwise identical clostridial toxin lacking said at least one amino acid modification.

The engineered clostridial toxins of the invention are suitable for use in any of the therapies described above, and advantageously may demonstrate a reduction in, or absence of, side effects compared to the use of known clostridial toxin therapeutics.

The increased tissue retention properties of the engineered clostridial toxins of the invention also provide increased potency and/or duration of action, and can allow for reduced dosages to be used compared to known clostridial toxin therapeutics (or increased dosages without any additional adverse effects), thus providing further advantages.

Thus, in one embodiment, an engineered clostridial toxin of the invention has increased potency, increased tissue retention, and/or increased duration of action, as compared to the corresponding unmodified clostridial toxin.

As discussed below in more detail, the increase in pI provided by the at least one amino acid modification means that an engineered clostridial toxin of the invention has, at a given pH, a net charge that is more positive than the net charge on an otherwise identical clostridial toxin lacking said at least one amino acid modification. Without wishing to be bound by any one theory, the present inventors believe that this increased positive charge allows the engineered clostridial toxins of the present invention to display longer tissue retention times at the site of administration due to favourable electrostatic interactions between the engineered clostridial toxin and anionic extracellular components (such as cell membranes and heparin sulphate proteoglycans) at the site of administration. These improved electrostatic interactions serve to reduce the diffusion of the engineered clostridial toxin away from the site of administration, thus improving tissue retention.

By way of example, the improved tissue retention properties of an engineered clostridial toxin of the invention may allow for (i) higher doses into individual muscles, such as the sternocleidomastoid, without spreading into nearby muscles in the neck to cause difficult swallowing, and (ii) higher total doses (to all muscles) in a single treatment, without spreading into the circulation and causing systemic effects such as difficult breathing. Advantages to patients may include more effective treatment of large muscles such as the sternocleidomastoid muscle, increased opportunity to inject several different muscles during each treatment, and possible longer duration of effective treatment (longer before re-treatment is necessary) because of higher dosing.

In one embodiment, an engineered clostridial toxin of the invention has, in use, a positive net charge (for example, when the engineered clostridial toxin, in use, is located at a desired administration site in a tissue).

The isoelectric point (pI) is a specific property of a given protein. As is well known in the art, proteins are made from a specific sequence of amino acids (also referred to when in a protein as amino acid residues). Each amino acid of the standard set of twenty has a different side chain (or R group), meaning that each amino acid residue in a protein displays different chemical properties such as charge and hydrophobicity. These properties may be influenced by the surrounding chemical environment, such as the temperature and pH. The overall chemical characteristics of a protein will depend on the sum of these various factors.

Certain amino acid residues (detailed below) possess ionisable side chains that may display an electric charge depending on the surrounding pH. Whether such a side chain is charged or not at a given pH depends on the pKa of the relevant ionisable moiety, wherein pKa is the negative logarithm of the acid dissociation constant (Ka) for a specified proton from a conjugate base.

For example, acidic residues such as aspartic acid and glutamic acid have side chain carboxylic acid groups with pKa values of approximately 4.1 (precise pKa values may depend on temperature, ionic strength and the microenvironment of the ionisable group). Thus, these side chains exhibit a negative charge at a pH of 7.4 (often referred to as "physiological pH"). At low pH values, these side chains will become protonated and lose their charge.

Conversely, basic residues such as lysine and arginine have nitrogen-containing side chain groups with pKa values of approximately 10-12. These side chains therefore exhibit a positive charge at a pH of 7.4. These side chains will become de-protonated and lose their charge at high pH values.

The overall (net) charge of a protein molecule therefore depends on the number of acidic and basic residues present in the protein (and their degree of surface exposure) and on the surrounding pH. Changing the surrounding pH changes the overall charge on the protein. Accordingly, for every protein there is a given pH at which the number of positive and negative charges is equal and the protein displays no overall net charge. This point is known as the isoelectric point (pI). The isoelectric point is a standard concept in protein biochemistry with which the skilled person would be familiar.

The isoelectric point (pI) is therefore defined as the pH value at which a protein displays a net charge of zero. An increase in pI means that a higher pH value is required for the protein to display a net charge of zero. Thus, an increase in pI represents an increase in the net positive charge of a protein at a given pH.

Conversely, a decrease in pI means that a lower pH value is required for the protein to display a net charge of zero. Thus, a decrease in pI represents a decrease in the net positive charge of a protein at a given pH.

Methods of determining the pI of a protein are known in the art and would be familiar to a skilled person. By way of example, the pI of a protein can be calculated from the average pKa values of each amino acid present in the protein ("calculated pI"). Such calculations can be performed using computer programs known in the art; preferred example computer programs for calculating pI values include Protein Calculator from the Scripps Research Institute and Compute pI/MW Tool from ExPASy. Comparisons of pI values between different molecules should be made using the same calculation technique/program.

Where appropriate, the calculated pI of a protein can be confirmed experimentally using the technique of isoelectric focusing ("observed pI"). This technique uses electrophoresis to separate proteins according to their pI. Isoelectric focusing is typically performed using a gel that has an immobilised pH gradient. When an electric field is applied, the protein migrates through the pH gradient until it reaches the pH at which it has zero net charge, this point being the pI of the protein. Results provided by isoelectric focusing are typically relatively low-resolution in nature, and thus the present inventors believe that results provided by calculated pI (as described above) are more appropriate to use.

Throughout the present specification, "pI" means "calculated pI" unless otherwise stated.

The pI of a protein may be increased or decreased by altering the number of basic and/or acidic groups displayed on its surface. This can be achieved by modifying one or more amino acids of the protein. For example, an increase in pI may be provided by reducing the number of acidic residues, or by increasing the number of basic residues. Such amino acid modifications are discussed in more detail below.

Native (unmodified) clostridial toxins have a pI of approximately 5-6. Thus, at a pH of 7.4, native botulinum toxins possess a negative net charge. By way of example, the pI of BoNT/A is 6.4, and a BoNT/A molecule has a net charge at pH 7.4 of −8. These pI values are calculated as described above.

TABLE 1

| CLOSTRIDIAL TOXIN | pI |
|---|---|
| BoNT/A | 6.4 |
| BoNT/B | 5.3 |
| BoNT/C$_1$ | 5.5 |
| BoNT/D | 5.5 |
| BoNT/E | 6.0 |
| BoNT/F | 5.6 |
| BoNT/G | 5.2 |
| TeNT | 5.8 |

As described above, in one embodiment, an engineered clostridial toxin of the present invention comprises at least one amino acid modification, wherein said at least one amino acid modification increases the isoelectric point (pI) of the engineered clostridial toxin to a value that is at least 0.2 pI units higher than the pI of an otherwise identical clostridial toxin lacking said at least one amino acid modification.

Thus, in the context of the present invention, an increase in pI of 0.2 units in the context of an engineered BoNT/A clostridial toxin would be an increase in pI from 6.4 to 6.6.

As described above, in one embodiment, an engineered clostridial toxin of the present invention comprises at least one amino acid modification, wherein said at least one amino acid modification increases the isoelectric point (pI) of the engineered clostridial toxin to a value that is at least one pI unit higher than the pI of an otherwise identical clostridial toxin lacking said at least one amino acid modification.

Thus, in the context of the present invention, an increase in pI of 1 unit in the context of an engineered BoNT/A clostridial toxin would be an increase in pI from 6.4 to 7.4.

In one embodiment, the engineered clostridial toxin has a pI of at least 5.5.

In one embodiment, the engineered clostridial toxin has a pI of at least 6 (for example, at least 6, at least 7, at least 8, or at least 9).

In one embodiment, the engineered clostridial toxin has a pI of at least 6.5.

In one embodiment, the engineered clostridial toxin has a pI of at least 7.

In one embodiment, the engineered clostridial toxin has a pI of between 6.5 and 9.5 (for example a pI of between 6.5 and 7.5).

As discussed above, the engineered clostridial toxins of the present invention have increased tissue retention properties that also provide increased potency and/or duration of action, and can allow for reduced dosages to be used compared to known clostridial toxin therapeutics (or increased dosages without any additional effects). One way in which these advantageous properties (which represent an increase in the therapeutic index) may be defined is in terms of the Safety Ratio of the engineered clostridial toxin. In this regard, undesired effects of a clostridial toxin (caused by diffusion of the toxin away from the site of administration) can be assessed experimentally by measuring percentage bodyweight loss in a relevant animal model (e.g. a mouse, where loss of bodyweight is detected within seven days of administration). Conversely, desired on-target effects of a clostridial toxin can be assessed experimentally by Digital Abduction Score (DAS) assay, a measurement of muscle paralysis. The DAS assay may be performed by injection of 20 µl of clostridial toxin, formulated in Gelatin Phosphate Buffer, into the mouse gastrocnemius/soleus complex, followed by assessment of Digital Abduction Score using the method of Aoki (Aoki KR, Toxicon 39: 1815-1820; 2001). In the DAS assay, mice are suspended briefly by the tail in order to elicit a characteristic startle response in which the mouse extends its hind limbs and abducts its hind digits. Following clostridial toxin injection, the varying degrees of digit abduction are scored on a five-point scale (0=normal to 4=maximal reduction in digit abduction and leg extension).

The Safety Ratio of a clostridial toxin may then be expressed as the ratio between the amount of toxin required for a 10% drop in a bodyweight (measured at peak effect within the first seven days after dosing in a mouse) and the amount of toxin required for a DAS score of 2. High Safety Ratio scores are therefore desired, and indicate a toxin that is able to effectively paralyse a target muscle with little undesired off-target effects. An engineered toxin of the present invention has a Safety Ratio that is higher than the Safety Ratio of an equivalent unmodified (native) botulinum toxin.

Thus, in one embodiment, an engineered clostridial toxin of the present invention has a Safety Ratio of at least 8 (for example, at least 8, 9, 10, 15, 20, 25, 30, 35, 40, 45 or 50), wherein Safety Ratio is calculated as: dose of toxin required for −10% bodyweight change (pg/mouse) divided by DAS $ED_{50}$ (pg/mouse) [$ED_{50}$=dose required to produce a DAS score of 2].

In one embodiment, an engineered clostridial toxin of the present invention has a Safety Ratio of at least 10. In one embodiment, an engineered clostridial toxin of the present invention has a Safety Ratio of at least 15.

An engineered clostridial toxin of the present invention comprises at least one amino acid modification. Said at least one amino acid modification increases the pI of the clostridial toxin, as discussed above. In the context of the present invention, an amino acid modification is a modification of the amino acid sequence of a clostridial toxin. Such a modification may be effected by replacing one amino acid in the sequence with another (i.e. a substitution), by inserting a new amino acid into the sequence, or by deleting an amino acid of the sequence. Amino acids incorporated into an amino acid sequence in a protein are also referred to as amino acid residues.

The 20 standard amino acids found in proteins are as follows:

TABLE 2

| AMINO ACID | | | SIDE CHAIN |
|---|---|---|---|
| Aspartic acid | Asp | D | Charged (acidic) |
| Glutamic acid | Glu | E | Charged (acidic) |
| Arginine | Arg | R | Charged (basic) |
| Lysine | Lys | K | Charged (basic) |
| Histidine | His | H | Uncharged (polar) |
| Asparagine | Asn | N | Uncharged (polar) |
| Glutamine | Gln | Q | Uncharged (polar) |
| Serine | Ser | S | Uncharged (polar) |
| Threonine | Thr | T | Uncharged (polar) |
| Tyrosine | Tyr | Y | Uncharged (polar) |
| Methionine | Met | M | Uncharged (polar) |
| Tryptophan | Trp | W | Uncharged (polar) |
| Cysteine | Cys | C | Uncharged (polar) |
| Alanine | Ala | A | Uncharged (hydrophobic) |
| Glycine | Gly | G | Uncharged (hydrophobic) |
| Valine | Val | V | Uncharged (hydrophobic) |
| Leucine | Leu | L | Uncharged (hydrophobic) |
| Isoleucine | Ile | I | Uncharged (hydrophobic) |
| Proline | Pro | P | Uncharged (hydrophobic) |
| Phenylalanine | Phe | F | Uncharged (hydrophobic) |

The following amino acids are considered charged amino acids: aspartic acid (negative), glutamic acid (negative), arginine (positive), and lysine (positive).

At a pH of 7.4, the side chains of aspartic acid (pKa 3.1) and glutamic acid (pKa 4.1) have a negative charge, while the side chains of arginine (pKa 12.5) and lysine (pKa 10.8) have a positive charge. Aspartic acid and glutamic acid are referred to as acidic amino acid residues. Arginine and lysine are referred to as basic amino acid residues.

The following amino acids are considered uncharged, polar (meaning they can participate in hydrogen bonding) amino acids: asparagine, glutamine, histidine, serine, threonine, tyrosine, cysteine, methionine, tryptophan.

The following amino acids are considered uncharged, hydrophobic amino acids: alanine, valine, leucine, isoleucine, phenylalanine, proline, and glycine.

An increase in the pI of a clostridial toxin can be effected by introducing into the clostridial toxin one or more amino acid modifications that increases the ratio of positive to negative charges in the clostridial toxin.

In one embodiment, the at least one amino acid modification is selected from: an amino acid substitution, an amino acid insertion, and an amino acid deletion.

In an amino acid substitution, an amino acid residue that forms part of the clostridial toxin amino acid sequence is replaced with a different amino acid residue. The replacement amino acid residue may be one of the 20 standard amino acids, as described above.

Alternatively, the replacement amino acid in an amino acid substitution may be a non-standard amino acid (an amino acid that is not part of the standard set of 20 described above). By way of example, the replacement amino acid may be a basic non-standard amino acid, e.g. L-Ornithine, L-2-amino-3-guanidinopropionic acid, or D-isomers of Lysine, Arginine and Ornithine). Methods for introducing non-standard amino acids into proteins are known in the art, and include recombinant protein synthesis using E. coli auxotrophic expression hosts.

In an amino acid insertion, an additional amino acid residue (one that is not normally present) is incorporated into the clostridial toxin amino acid sequence, thus increasing the total number of amino acid residues in said sequence. In an amino acid deletion, an amino acid residue is removed from the clostridial toxin amino acid sequence, thus reducing the total number of amino acid residues in said sequence.

Methods for modifying proteins by substitution, insertion or deletion of amino acid residues are known in the art. By way of example, amino acid modifications may be introduced by modification of a DNA sequence encoding a clostridial toxin. This can be achieved using standard molecular cloning techniques, for example by site-directed mutagenesis where short strands of DNA (oligonucleotides) coding for the desired amino acid(s) are used to replace the original coding sequence using a polymerase enzyme, or by inserting/deleting parts of the gene with various enzymes (e.g., ligases and restriction endonucleases). Alternatively a modified gene sequence can be chemically synthesised.

In one embodiment, the at least one amino acid modification is selected from: substitution of an acidic amino acid residue with a basic amino acid residue; substitution of an acidic amino acid residue with an uncharged amino acid residue; substitution of an uncharged amino acid residue with a basic amino acid residue; insertion of a basic amino acid residue; and deletion of an acidic amino acid residue.

In a preferred embodiment, the at least one amino acid modification is a substitution, which advantageously maintains the same number of amino acid residues in the clostridial toxin. In one embodiment, the substitution is selected from: substitution of an acidic amino acid residue with a basic amino acid residue, substitution of an acidic amino acid residue with an uncharged amino acid residue, and substitution of an uncharged amino acid residue with a basic amino acid residue. In one embodiment, the basic amino acid residue is a lysine residue or an arginine residue. In one embodiment, the basic amino acid residue is a lysine residue. In one embodiment, the basic amino acid residue is an arginine residue. In one embodiment, wherein the substitution is a substitution of an acidic amino acid residue with an uncharged amino acid residue, the acidic amino acid residue is replaced with its corresponding uncharged amide amino acid residue (i.e. aspartic acid is replaced with asparagine, and glutamic acid is replaced with glutamine).

In another preferred embodiment, the at least one amino acid modification is a substitution of an acidic amino acid residue with a basic amino acid residue, or a substitution of an uncharged amino acid residue with a basic amino acid residue. In one embodiment, the basic amino acid residue is a lysine residue. In one embodiment, the basic amino acid residue is an arginine residue.

An engineered clostridial toxin of the invention may comprise more than one amino acid modification. Thus, in one embodiment, the engineered clostridial toxin (as described above) comprises between 1 and 90 amino acid modifications (for example, between 1 and 80, between 1 and 70, between 1 and 60, between 1 and 50, between 1 and 40, between 1 and 30, between 1 and 20, between 1 and 10, between 3 and 50, between 3 and 40, between 3 and 30, between 4 and 40, between 4 and 30, between 5 and 40, between 5 and 30, or between 10 and 25 amino acid modifications). In one embodiment, the engineered clostridial toxin (as described above) comprises between 1 and 20 amino acid modifications. In one embodiment, the engineered clostridial toxin (as described above) comprises between 1 and 10 amino acid modifications. In one embodiment, the engineered clostridial toxin (as described above) comprises between 2 and 20 amino acid modifications. In one embodiment, the engineered clostridial toxin (as described above) comprises between 2 and 15 amino acid modifications. In one embodiment, the engineered clostridial toxin (as described above) comprises between 2 and 10 amino acid modifications. In one embodiment, the engineered clostridial toxin (as described above) comprises between 3 and 20 amino acid modifications. In one embodiment, the engineered clostridial toxin (as described above) comprises between 3 and 15 amino acid modifications. In one embodiment, the engineered clostridial toxin (as described above) comprises between 3 and 10 amino acid modifications. In one embodiment, the engineered clostridial toxin (as described above) comprises between 4 and 40 amino acid modifications. In one embodiment, the engineered clostridial toxin comprises at least 2, at least 3, at least 4, at least 5, at least 6, at least 7, at least 8, at least 9, or at least 10 amino acid modifications. In one embodiment, the engineered clostridial toxin comprises at least 3 amino acid modifications (for example, at least 3 amino acid substitutions). In one embodiment, the engineered clostridial toxin comprises at least 4 amino acid modifications (for example, at least 4 amino acid substitutions). Each of said amino acid modifications is an amino acid modification as described above. Thus, each of said amino acid modifications contributes to the increase in pI of the engineered clostridial toxin (as compared to the pI of an otherwise identical clostridial toxin lacking said amino acid modifications).

Any clostridial toxin amino acid (i.e. amino acid residue) that is not located in the clostridial toxin binding domain ($H_C$ domain) can be modified as described above, as long as the outcome of said modification is an increase in the clostridial toxin pI (as described above). However, the present inventors have identified subsets of clostridial toxin amino acids that are particularly suitable targets for modification.

Preferred target amino acids may possess certain qualities. By way of example, a preferred target amino acid may be: (i) a surface exposed amino acid; (ii) located outside of a clostridial toxin protein secondary structure; (iii) located in a clostridial toxin protein region that is non-essential for protein function; (iv) an amino acid whose identity is not conserved between clostridial toxin types, subtypes, or serotypes; (iv) an amino acid whose modification does not create a predicted ubiquitination site; or (v) any combination of the foregoing.

As described above, the engineered clostridial toxins of the invention feature one or more amino acid modifications located in either the clostridial toxin $H_N$ translocation domain or the clostridial toxin light chain.

Examples of clostridial toxin light chain reference sequences include:
Botulinum type A neurotoxin: amino acid residues 1-448
Botulinum type B neurotoxin: amino acid residues 1-440
Botulinum type C$_1$ neurotoxin: amino acid residues 1-441
Botulinum type D neurotoxin: amino acid residues 1-445
Botulinum type E neurotoxin: amino acid residues 1-422
Botulinum type F neurotoxin: amino acid residues 1-439
Botulinum type G neurotoxin: amino acid residues 1-441
Tetanus neurotoxin: amino acid residues 1-457

Examples of clostridial toxin H$_N$ domain reference sequences include:
Botulinum type A neurotoxin: amino acid residues 449-871
Botulinum type B neurotoxin: amino acid residues 443-862
Botulinum type C$_1$ neurotoxin: amino acid residues 450-866
Botulinum type D neurotoxin: amino acid residues 449-871
Botulinum type E neurotoxin: amino acid residues 455-845
Botulinum type F neurotoxin: amino acid residues 450-864
Botulinum type G neurotoxin: amino acid residues 449-871
Tetanus neurotoxin: amino acid residues 456-879

Examples of clostridial toxin H$_C$ domain reference sequences include:
Botulinum type A neurotoxin: amino acid residues 872-1278
Botulinum type B neurotoxin: amino acid residues 863-1291
Botulinum type C$_1$ neurotoxin: amino acid residues 867-1291
Botulinum type D neurotoxin: amino acid residues 872-1276
Botulinum type E neurotoxin: amino acid residues 846-1252
Botulinum type F neurotoxin: amino acid residues 865-1278
Botulinum type G neurotoxin: amino acid residues 872-1297
Tetanus neurotoxin: amino acid residues 880-1315

The above-identified reference sequences should be considered a guide, as slight variations may occur according to sub-serotypes. By way of example, US 2007/0166332 (hereby incorporated by reference in its entirety) cites slightly different clostridial sequences:
Light chain:
Botulinum type A neurotoxin: amino acid residues M1-K448
Botulinum type B neurotoxin: amino acid residues M1-K441
Botulinum type C$_1$ neurotoxin: amino acid residues M1-K449
Botulinum type D neurotoxin: amino acid residues M1-R445
Botulinum type E neurotoxin: amino acid residues M1-R422
Botulinum type F neurotoxin: amino acid residues M1-K439
Botulinum type G neurotoxin: amino acid residues M1-K446 Tetanus neurotoxin: amino acid residues M1-A457
H$_N$ domain:
Botulinum type A neurotoxin: amino acid residues A449-K871
Botulinum type B neurotoxin: amino acid residues A442-S858
Botulinum type C$_1$ neurotoxin: amino acid residues T450-N866
Botulinum type D neurotoxin: amino acid residues D446-N862
Botulinum type E neurotoxin: amino acid residues K423-K845
Botulinum type F neurotoxin: amino acid residues A440-K864
Botulinum type G neurotoxin: amino acid residues S447-S863
Tetanus neurotoxin: amino acid residues S458-V879
H$_C$ domain:
Botulinum type A neurotoxin: amino acid residues N872-L1296
Botulinum type B neurotoxin: amino acid residues E859-E1291
Botulinum type C$_1$ neurotoxin: amino acid residues N867-E1291
Botulinum type D neurotoxin: amino acid residues S863-E1276
Botulinum type E neurotoxin: amino acid residues R846-K1252
Botulinum type F neurotoxin: amino acid residues K865-E1274
Botulinum type G neurotoxin: amino acid residues N864-E1297
Tetanus neurotoxin: amino acid residues I880-D1315

In one embodiment, wherein said at least one amino acid modification is located in the clostridial toxin translocation domain (H$_N$ domain), said at least one amino acid modification is not located in the clostridial toxin belt region. The clostridial toxin belt region (as determined by visual inspection of structures and models) is defined as follows:
Botulinum type A neurotoxin: amino acid residues 492-545
Botulinum type B neurotoxin: amino acid residues 472-532
Botulinum type C$_1$ neurotoxin: amino acid residues 494-543
Botulinum type D neurotoxin: amino acid residues 489-539
Botulinum type E neurotoxin: amino acid residues 466-515
Botulinum type F neurotoxin: amino acid residues 485-536
Botulinum type G neurotoxin: amino acid residues 489-538
Tetanus neurotoxin: amino acid residues 506-556

In one embodiment, the at least one amino acid modification (as described above) is a modification of a surface exposed amino acid residue. Surface exposed amino acid residues are those present on the exterior of a folded protein and so accessible to the surrounding solvent, in contrast to those amino acid residues that are located in the interior of a folded protein. The degree of surface exposure of an amino acid residue and thus its exposure to the surrounding solvent depends on its position within the folded protein, and also on the conformation adopted by the protein. Modification of an amino acid residue with a high degree of surface exposure may therefore have a greater effect on the protein's isoelectric point than modification of an amino acid residue with a low degree of surface exposure. Methods for determining the degree of surface exposure of an amino acid residue are known in the art. By way of example, the computer program AreaIMol (part of the CCP4 suite of computer programs) can be used to calculate the degree of surface exposure of amino acid residues in a given protein. Surface exposed amino acid residues may also be identified by visual inspection of a protein crystal structure (such as provided by X-ray crystallography). In one embodiment, a surface exposed amino acid residue has a sum AreaIMol value of at least 40.

In one embodiment, the at least one amino acid modification comprises modification of an amino acid residue selected from: an aspartic acid residue, a glutamic acid residue, a histidine residue, an asparagine residue, a glutamine residue, a serine residue, a threonine residue, an alanine residue, a glycine residue, a valine residue, a leucine residue, and an isoleucine residue. The present inventors have identified that amino acid residues from this group represent particularly suitable targets for modification according to the present invention.

In one embodiment, wherein the amino acid modification comprises modification of an amino acid residue selected from an aspartic acid residue, a glutamic acid residue, a histidine residue, an asparagine residue, a glutamine residue, a serine residue, a threonine residue, an alanine residue, a glycine residue, a valine residue, a leucine residue, and an isoleucine residue (as described above), the amino acid residue is substituted with a lysine residue or an arginine residue. In one embodiment, the amino acid residue is substituted with an arginine residue. Thus, in one embodiment, a negatively charged residue, a polar residue, or an uncharged residue is substituted with a positively charged residue, thus increasing the ratio of positive to negative charges and increasing the pI of the clostridial toxin.

In one embodiment, the at least one amino acid modification (as described above) comprises modification of an asparagine amino acid residue or a glutamine amino acid residue (both uncharged, polar residues). In one embodiment, the asparagine or glutamine amino acid residue is substituted with a lysine residue or an arginine residue (both positively charged residues). In one embodiment, the asparagine or glutamine amino acid residue is substituted with a lysine residue. In one embodiment, the asparagine or glutamine amino acid residue is substituted with an arginine residue.

In one embodiment, the engineered clostridial toxin is a BoNT/A. A reference BoNT/A sequence has the UniProtKB Accession Number P10845. In one embodiment wherein the engineered clostridial toxin is a BoNT/A, the engineered clostridial toxin is a BoNT/A1

The present inventors have identified certain amino acids that represent preferred targets for amino acid modification in a BoNT/A clostridial toxin $H_N$ domain.

In one embodiment, wherein the engineered clostridial toxin is a BoNT/A, said engineered BoNT/A comprises a modification of at least one (for example, at least 1, 2, 3, 4, 5, 10, 15, 20, 25, 30, 35, 40, 45, 50 or all 55) amino acid selected from: D474, N476, D484, N486, I487, E488, A489, A490, E491, D546, E558, E560, H561, I566, L568, N570, S571, L577, N578, A597, E599, A601, E620, V621, T623, D625, T631, N645, L647, D650, D651, I668, E670, A672, V675, S683, I685, A686, N687, N752, Q753, T755, E756, E757, E758, N760, N761, I762, N763, D825, I831, G832, T847, D848, and D858; and said amino acid modification(s) increase(s) the isoelectric point (pI) of the engineered BoNT/A to a value that is at least 0.2 (for example, at least 0.2, 0.3, 0.4, 0.5, 0.6, 0.7, 0.8, 0.9 or 1) pI units higher than the pI of an otherwise identical BoNT/A lacking said amino acid modification(s). In one embodiment said modification comprises substitution of the amino acid with a lysine residue or an arginine residue. In one embodiment, said modification comprises substitution of the amino acid with a lysine residue. In one embodiment, said modification comprises substitution of the amino acid with an arginine residue.

In one embodiment, wherein the engineered clostridial toxin is a BoNT/A, said engineered BoNT/A comprises a modification of at least one (for example, at least 1, 2, 3, 4, 5, 10, 15 or all 17) amino acid selected from: N476, S564, N578, E599, L647, D650, D651, V675, I685, N687, T755, E757, N761, N763, I831, T847, and I849; and said amino acid modification(s) increase(s) the isoelectric point (pI) of the engineered BoNT/A to a value that is at least 0.2 (for example, at least 0.2, 0.3, 0.4, 0.5, 0.6, 0.7, 0.8, 0.9 or 1) pI units higher than the pI of an otherwise identical BoNT/A lacking said amino acid modification(s). In one embodiment said modification comprises substitution of the amino acid with a lysine residue or an arginine residue. In one embodiment, said modification comprises substitution of the amino acid with a lysine residue. In one embodiment, said modification comprises substitution of the amino acid with an arginine residue.

In one embodiment, wherein the engineered clostridial toxin is a BoNT/A, said engineered BoNT/A comprises a modification of at least one (for example, at least 1, 2, 3, 4, 5 or all 6) amino acid selected from: S564, L647, D650, D651, T847, and I849; and said amino acid modification(s) increase(s) the isoelectric point (pI) of the engineered BoNT/A to a value that is at least 0.2 (for example, at least 0.2, 0.3, 0.4, 0.5, 0.6, 0.7, 0.8, 0.9 or 1) pI units higher than the pI of an otherwise identical BoNT/A lacking said amino acid modification(s). In one embodiment said modification comprises substitution of the amino acid with a lysine residue or an arginine residue. In one embodiment, said modification comprises substitution of the amino acid with a lysine residue. In one embodiment, said modification comprises substitution of the amino acid with an arginine residue.

In one embodiment, wherein the engineered clostridial toxin is a BoNT/A, said engineered BoNT/A comprises a modification of at least one (for example, at least 1, 2, 3, 4, 5 or all 6) amino acid selected from: N476, N763, N687, E599, I831, and N761; and said amino acid modification(s) increase(s) the isoelectric point (pI) of the engineered BoNT/A to a value that is at least 0.2 (for example, at least 0.2, 0.3, 0.4, 0.5, 0.6, 0.7, 0.8, 0.9 or 1) pI units higher than the pI of an otherwise identical BoNT/A lacking said amino acid modification(s). In one embodiment said modification comprises substitution of the amino acid with a lysine residue or an arginine residue. In one embodiment, said modification comprises substitution of the amino acid with a lysine residue. In one embodiment, said modification comprises substitution of the amino acid with an arginine residue.

In one embodiment, wherein the engineered clostridial toxin is a BoNT/A, said engineered BoNT/A comprises a modification of at least one (for example, at least 1, 2, 3, 4, or all 5) amino acid selected from: N578, V675, I685, T755, and E757; and said amino acid modification(s) increase(s) the isoelectric point (pI) of the engineered BoNT/A to a value that is at least 0.2 (for example, at least 0.2, 0.3, 0.4, 0.5, 0.6, 0.7, 0.8, 0.9 or 1) pI units higher than the pI of an otherwise identical BoNT/A lacking said amino acid modification(s). In one embodiment said modification comprises substitution of the amino acid with a lysine residue or an arginine residue. In one embodiment, said modification comprises substitution of the amino acid with a lysine residue. In one embodiment, said modification comprises substitution of the amino acid with an arginine residue.

In one embodiment, the engineered clostridial toxin is a BoNT/B. A reference BoNT/B sequence has the UniProtKB Accession Number P10844.

The present inventors have identified certain amino acids that represent preferred targets for amino acid modification in a BoNT/B clostridial toxin $H_N$ domain.

In one embodiment, wherein the engineered clostridial toxin is a BoNT/B, said engineered BoNT/B comprises a modification of at least one (for example, at least 1, 2, 3, 4, 5, 10, 15, 20, 25, 30, 35, or all 40) amino acid selected from: V443, G444, D453, S468, D533, E534, N535, T545, L548, D549, I550, D552, S557, L564, S566, N582, V584, N609, L619, N632, E633, G637, A646, I655, E657, V662, E669, S670, I672, D673, N739, I740, N748, N750, I818, G819, T834, I842, N845, and S858; and said amino acid modification(s) increase(s) the isoelectric point (pI) of the engineered BoNT/B to a value that is at least 0.2 (for example, at least 0.2, 0.3, 0.4, 0.5, 0.6, 0.7, 0.8, 0.9 or 1) pI units higher than the pI of an otherwise identical BoNT/B lacking said amino acid modification(s). In one embodiment said modification comprises substitution of the amino acid with a lysine residue or an arginine residue. In one embodiment, said modification comprises substitution of the amino acid with a lysine residue. In one embodiment, said modification comprises substitution of the amino acid with an arginine residue.

In one embodiment, the engineered clostridial toxin is a BoNT/C$_1$. A reference BoNT/C$_1$ sequence has the UniProtKB Accession Number P18640.

The present inventors have identified certain amino acids that represent preferred targets for amino acid modification in a BoNT/C$_1$ clostridial toxin H$_N$ domain.

In one embodiment, wherein the engineered clostridial toxin is a BoNT/C$_1$, said engineered BoNT/C$_1$ comprises a modification of at least one (for example, at least 1, 2, 3, 4, 5, 10, 15, 20, 25, 30, 35, 40, 45 or all 50) amino acid selected from: L451, D452, C453, E455, V472, T474, D475, L478, N483, E484, E485, E487, I489, L555, S556, D557, N558, E560, D561, E569, N574, S575, T584, G592, Q594, G596, D617, N640, S641, V642, G645, N646, E661, E665, T667, A670, S678, V680, Q681, E682, S750, G751, S759, Q760, V826, G827, N842, T843, N847, and N853; and said amino acid modification(s) increase(s) the isoelectric point (pI) of the engineered BoNT/C$_1$ to a value that is at least 0.2 (for example, at least 0.2, 0.3, 0.4, 0.5, 0.6, 0.7, 0.8, 0.9 or 1) pI units higher than the pI of an otherwise identical BoNT/C$_1$ lacking said amino acid modification(s). In one embodiment said modification comprises substitution of the amino acid with a lysine residue or an arginine residue. In one embodiment, said modification comprises substitution of the amino acid with a lysine residue. In one embodiment, said modification comprises substitution of the amino acid with an arginine residue.

In one embodiment, the engineered clostridial toxin is a BoNT/D. A reference BoNT/D sequence has the UniProtKB Accession Number P19321.

The present inventors have identified certain amino acids that represent preferred targets for amino acid modification in a BoNT/D clostridial toxin H$_N$ domain.

In one embodiment, wherein the engineered clostridial toxin is a BoNT/D, said engineered BoNT/D comprises a modification of at least one (for example, at least 1, 2, 3, 4, 5, 10, 15, 20, 25, 30, 35, 40, 45, 50, 55, 60, or all 62) amino acid selected from: Q469, E470, E473, N474, D479, E480, N482, V483, Q484, N485, S487, D488, S552, N553, N554, V555, E556, N557, I558, L560, T562, S563, V564, G569, S571, N572, G588, Q590, T614, D616, S619, S622, N636, S637, L639, G641, N642, E657, E661, T663, A666, V669, S674, I676, Q677, E678, S746, G747, D749, E751, N752, I753, Q756, N818, V822, G823, E837, N838, T839, N843, N849, and N850; and said amino acid modification(s) increase(s) the isoelectric point (pI) of the engineered BoNT/D to a value that is at least 0.2 (for example, at least 0.2, 0.3, 0.4, 0.5, 0.6, 0.7, 0.8, 0.9 or 1) pI units higher than the pI of an otherwise identical BoNT/B lacking said amino acid modification(s). In one embodiment said modification comprises substitution of the amino acid with a lysine residue or an arginine residue. In one embodiment, said modification comprises substitution of the amino acid with a lysine residue. In one embodiment, said modification comprises substitution of the amino acid with an arginine residue.

In one embodiment, the engineered clostridial toxin is a BoNT/E. A reference BoNT/E sequence has the UniProtKB Accession Number Q00496. In one embodiment wherein the engineered clostridial toxin is a BoNT/E, the engineered clostridial toxin is a BoNT/E3.

The present inventors have identified certain amino acids that represent preferred targets for amino acid modification in a BoNT/E clostridial toxin H$_N$ domain.

In one embodiment, wherein the engineered clostridial toxin is a BoNT/E, said engineered BoNT/E comprises a modification of at least one (for example, at least 1, 2, 3, 4, 5, 10, 15, 20, 25, 30, 35, 40, 45, 50, or all 52) amino acid selected from: D474, N476, E479, E480, D484, N486, I487, E488, A489, A490, E491, E492, L496, D497, Q500, Q501, L504, N507, D509, N510, N514, S516, E518, Q527, L530, N533, I534, E535, N539, Y548, I566, L568, D589, A597, E599, A601, L604, Y612, E620, N645, L647, Y648, D651, E737, E741, Y803, Y824, D825, G828, I831, G832, and D835; and said amino acid modification(s) increase(s) the isoelectric point (pI) of the engineered BoNT/E to a value that is at least 0.2 (for example, at least 0.2, 0.3, 0.4, 0.5, 0.6, 0.7, 0.8, 0.9 or 1) pI units higher than the pI of an otherwise identical BoNT/E lacking said amino acid modification(s). In one embodiment said modification comprises substitution of the amino acid with a lysine residue or an arginine residue. In one embodiment, said modification comprises substitution of the amino acid with a lysine residue. In one embodiment, said modification comprises substitution of the amino acid with an arginine residue.

In one embodiment, the engineered clostridial toxin is a BoNT/F. A reference BoNT/F sequence has the UniProtKB Accession Number YP_001390123.

The present inventors have identified certain amino acids that represent preferred targets for amino acid modification in a BoNT/F clostridial toxin H$_N$ domain.

In one embodiment, wherein the engineered clostridial toxin is a BoNT/F, said engineered BoNT/F comprises a modification of at least one (for example, at least 1, 2, 3, 4, 5, 10, 15, 20, 25, 30, 35, 40, 45, 50, 55, 60, 65, 70, 75, 80, 85, or all 86) amino acid selected from: N463, E464, N468, T469, D474, D475, T476, T477, N478, N482, N485, N495, I499, Q501, I502, Q505, T506, N508, T509, V511, D513, D521, S522, S526, E527, I528, E529, V534, D535, L536, E549, G550, T552, N553, S558, E566, E567, S568, V586, H587, Q608, D613, A616, D617, S619, N630, N633, N639, E654, V656, E658, L660, T663, L665, V666, S671, I673, G674, S675, S676, E677, N678, T746, N751, L753, E754, E756, N758, I759, N760, N761, S799, S821, I822, N840, S841, E845, L846, S847, S848, T850, N851, D852, I854, L855, and I856; and said amino acid modification(s) increase(s) the isoelectric point (pI) of the engineered BoNT/F to a value that is at least 0.2 (for example, at least 0.2, 0.3, 0.4, 0.5, 0.6, 0.7, 0.8, 0.9 or 1) pI units higher than the pI of an otherwise identical BoNT/F lacking said amino acid modification(s). In one embodiment said modification comprises substitution of the amino acid with a lysine residue or an arginine residue. In one embodiment, said modification comprises substitution of the amino acid with a lysine residue. In one embodiment, said modification comprises substitution of the amino acid with an arginine residue.

In one embodiment, the engineered clostridial toxin is a BoNT/G. A reference BoNT/G sequence has the UniProtKB Accession Number Q60393.

The present inventors have identified certain amino acids that represent preferred targets for amino acid modification in a BoNT/G clostridial toxin H$_N$ domain.

In one embodiment, wherein the engineered clostridial toxin is a BoNT/G, said engineered BoNT/G comprises a modification of at least one (for example, at least 1, 2, 3, 4, 5, 10, 15, 20, 25, 30, 35, or all 36) amino acid selected from: N480, Q482, N483, N484, T485, E487, D540, N562, N570, N571, N572, T588, V589, T615, D621, N637, E638, E642, N643, I660, E662, I667, E674, S675, V677, G678, N679, S747, N755, D757, L823, D839, I841, D844, S846, and L847; and said amino acid modification(s) increase(s) the isoelectric point (pI) of the engineered BoNT/G to a value that is at least 0.2 (for example, at least 0.2, 0.3, 0.4, 0.5, 0.6, 0.7, 0.8, 0.9 or 1) pI units higher than the pI of an otherwise identical BoNT/G lacking said amino acid modification(s). In one embodiment said modification comprises substitution of the amino acid with a lysine residue or an arginine residue. In one embodiment, said modification comprises substitution of the amino acid with a lysine residue. In one embodiment, said modification comprises substitution of the amino acid with an arginine residue.

In one embodiment, the engineered clostridial toxin is a TeNT. A reference TeNT sequence has the UniProtKB Accession Number P04958.

The present inventors have identified certain amino acids that represent preferred targets for amino acid modification in a TeNT clostridial toxin $H_N$ domain.

In one embodiment, wherein the engineered clostridial toxin is a TeNT, said engineered TeNT comprises a modification of at least one (for example, at least 1, 2, 3, 4, 5, 10, 15, 20, 25, 30, 35, 40, 45, or all 49) amino acid selected from: A457, S458, L459, D461, L462, E486, E487, Q490, D491, N497, N504, D557, T571, T572, L573, Q574, N580, S581, N588, S589, T590, S598, Q605, G606, Q608, T631, I633, S640, Q655, E658, G659, N660, E675, I677, E679, T681, V684, A691, E692, S694, T695, Q696, A772, D773, E774, S862, N866, L867 and D868; and said amino acid modification(s) increase(s) the isoelectric point (pI) of the engineered TeNT to a value that is at least 0.2 (for example, at least 0.2, 0.3, 0.4, 0.5, 0.6, 0.7, 0.8, 0.9 or 1) pI units higher than the pI of an otherwise identical TeNT lacking said amino acid modification(s). In one embodiment said modification comprises substitution of the amino acid with a lysine residue or an arginine residue. In one embodiment, said modification comprises substitution of the amino acid with a lysine residue. In one embodiment, said modification comprises substitution of the amino acid with an arginine residue.

The present inventors have identified certain amino acids that represent preferred targets for amino acid modification in a BoNT/A clostridial toxin light chain.

In one embodiment, wherein the engineered clostridial toxin is a BoNT/A, said engineered BoNT/A comprises a modification of at least one (for example, at least 1, 2, 3, 4, 5, 10, 15, 20, 25 or all 28) amino acid selected from: N5, Q7, N9, D12, N15, Q31, D58, N60, D74, N82, T122, D124, E126, Q139, D141, E281, L284, S295, Q311, D326, D334, N377, TYR387, N394, N396, N410, M411, and N418; and said amino acid modification(s) increase(s) the isoelectric point (pI) of the engineered BoNT/A to a value that is at least 0.2 (for example, at least 0.2, 0.3, 0.4, 0.5, 0.6, 0.7, 0.8, 0.9 or 1) pI units higher than the pI of an otherwise identical BoNT/A lacking said amino acid modification(s). In one embodiment said modification comprises substitution of the amino acid with a lysine residue or an arginine residue. In one embodiment, said modification comprises substitution of the amino acid with a lysine residue. In one embodiment, said modification comprises substitution of the amino acid with an arginine residue.

The present inventors have identified certain amino acids that represent preferred targets for amino acid modification in a BoNT/B clostridial toxin light chain.

In one embodiment, wherein the engineered clostridial toxin is a BoNT/B, said engineered BoNT/B comprises a modification of at least one (for example, at least 1, 2, 3, 4, 5, 10, 15, 20, 25, 30, 35, 40 or all 41 amino acid selected from: N6, N7, N9, N11, D12, N16, N17, N18, D41, E48, E57, N60, D75, D77, N80, E127, N130, N144, E147, E149, E185, N216, D245, E253, N316, D333, E335, D341, N385, D388, N389, E390, E395, E396, D402, D404, E406, E408, Q419, E423, and E427; and said amino acid modification(s) increase(s) the isoelectric point (pI) of the engineered BoNT/B to a value that is at least 0.2 (for example, at least 0.2, 0.3, 0.4, 0.5, 0.6, 0.7, 0.8, 0.9 or 1) pI units higher than the pI of an otherwise identical BoNT/B lacking said amino acid modification(s). In one embodiment said modification comprises substitution of the amino acid with a lysine residue or an arginine residue. In one embodiment, said modification comprises substitution of the amino acid with a lysine residue. In one embodiment, said modification comprises substitution of the amino acid with an arginine residue.

The present inventors have identified certain amino acids that represent preferred targets for amino acid modification in a BoNT/$C_1$ clostridial toxin light chain.

in one embodiment, wherein the engineered clostridial toxin is a BoNT/$C_1$, said engineered BoNT/$C_1$ comprises a modification of at least one (for example, at least 1, 2, 3, 4, 5, 10, 15, 20, 30, 40, or all 41) amino acid selected from: N6, N7, N9, D12, D15, N18, N31, E32, N55, N59, N75, N120, N121, N125, D128, Q142, N145, N177, N178, Q183, E184, D208, E211, Q247, N255, N311, E335, E339, N343, N368, N386, D389, D390, N391, Q396, N405, N407, N425, E427, D442, and N448; and said amino acid modification(s) increase(s) the isoelectric point (pI) of the engineered BoNT/$C_1$ to a value that is at least 0.2 (for example, at least 0.2, 0.3, 0.4, 0.5, 0.6, 0.7, 0.8, 0.9 or 1) pI units higher than the pI of an otherwise identical BoNT/$C_1$ lacking said amino acid modification(s). In one embodiment said modification comprises substitution of the amino acid with a lysine residue or an arginine residue. In one embodiment, said modification comprises substitution of the amino acid with a lysine residue. In one embodiment, said modification comprises substitution of the amino acid with an arginine residue.

The present inventors have identified certain amino acids that represent preferred targets for amino acid modification in a BoNT/D clostridial toxin light chain.

In one embodiment, wherein the engineered clostridial toxin is a BoNT/D, said engineered BoNT/D comprises a modification of at least one (for example, at least 1, 2, 3, 4, 5, 10, 15, 20, 30, or all 34) amino acid selected from: D7, N9, D12, N15, D16, N17, D53, D73, N119, E124, E139, E142, N143, Q177, Q178, N180, E184, E255, N308, D335, N336, N339, N343, N368, N386, D389, D390, N391, D397, N403, N407, E409, E416, and N443; and said amino acid modification(s) increase(s) the isoelectric point (pI) of the engineered BoNT/D to a value that is at least 0.2 (for example, at least 0.2, 0.3, 0.4, 0.5, 0.6, 0.7, 0.8, 0.9 or 1) pI units higher than the pI of an otherwise identical BoNT/D lacking said amino acid modification(s). In one embodiment said modification comprises substitution of the amino acid with a lysine residue or an arginine residue. In one embodiment, said modification comprises substitution of the amino acid with a lysine residue. In one embodiment, said modification comprises substitution of the amino acid with an arginine residue.

The present inventors have identified certain amino acids that represent preferred targets for amino acid modification in a BoNT/E clostridial toxin light chain.

In one embodiment, wherein the engineered clostridial toxin is a BoNT/E, said engineered BoNT/E comprises a modification of at least one (for example, at least 1, 2, 3, 4, 5, 10, 15, 20, 30, 35, or all 37) amino acid selected from: N5, N8, N10, D11, N14, D15, Q27, E28, Q53, N72, Q75, D117, N118, D121, N122, Q123, N138, N169, N170, N195, Q237, ILE244, Q290, N293, N297, D312, Q344, N362, N365, D366, N370, E373, N378, N379, N383, N390, and T397; and said amino acid modification(s) increase(s) the isoelectric point (pI) of the engineered BoNT/E to a value that is at least 0.2 (for example, at least 0.2, 0.3, 0.4, 0.5, 0.6, 0.7, 0.8, 0.9 or 1) pI units higher than the pI of an otherwise identical BoNT/E lacking said amino acid modification(s). In one embodiment said modification comprises substitution of the amino acid with a lysine residue or an arginine residue. In one embodiment, said modification comprises substitution of the amino acid with a lysine residue. In one embodiment, said modification comprises substitution of the amino acid with an arginine residue.

In one embodiment, wherein the engineered clostridial toxin is a BoNT/E, said engineered BoNT/E comprises a modification of a least one (for example, at least 1, 2, 3, 4, 5, 10, 15 or 20) amino acid selected from: N5, N8, N10, D11, N14, D15, Q27, E28, N72, Q75, N118, D121, N122, Q123, N138, Q237, Q290, N297, N362, N365, D366, N378, and N379; and said amino acid modification(s) increase(s) the isoelectric point (pI) of the engineered BoNT/E to a value that is at least 0.2 (for example, at least 0.2, 0.3, 0.4, 0.5, 0.6, 0.7, 0.8, 0.9 or 1) pI units higher than the pI of an otherwise identical BoNT/E lacking said amino acid modification(s). In one embodiment said modification comprises substitution of the amino acid with a lysine residue or an arginine residue. In one embodiment, said modification comprises substitution of the amino acid with a lysine residue. In one embodiment, said modification comprises substitution of the amino acid with an arginine residue.

In one embodiment, wherein the engineered clostridial toxin is a BoNT/E, said engineered BoNT/E comprises a modification of a least one (for example, at least 1, 2, 3, 4, 5, 10, 15 or all 19) amino acid selected from: N5, N8, N10, D11, N14, D15, N72, Q75, N118, N122, Q123, N138, Q237, Q290, Q297, N362, D366, N378, and N379; and said amino acid modification(s) increase(s) the isoelectric point (pI) of the engineered BoNT/E to a value that is at least 0.2 (for example, at least 0.2, 0.3, 0.4, 0.5, 0.6, 0.7, 0.8, 0.9 or 1) pI units higher than the pI of an otherwise identical BoNT/E lacking said amino acid modification(s). In one embodiment said modification comprises substitution of the amino acid with a lysine residue or an arginine residue. In one embodiment, said modification comprises substitution of the amino acid with a lysine residue. In one embodiment, said modification comprises substitution of the amino acid with an arginine residue.

In one embodiment, wherein the engineered clostridial toxin is a BoNT/E, said engineered BoNT/E comprises a modification of a least one (for example, at least 1, 2, 3, 4, 5, or all 6) amino acid selected from: N8, N10, Q75, Q123, N138, and Q237; and said amino acid modification(s) increase(s) the isoelectric point (pI) of the engineered BoNT/E to a value that is at least 0.2 (for example, at least 0.2, 0.3, 0.4, 0.5, 0.6, 0.7, 0.8, 0.9 or 1) pI units higher than the pI of an otherwise identical BoNT/E lacking said amino acid modification(s). In one embodiment said modification comprises substitution of the amino acid with a lysine residue or an arginine residue. In one embodiment, said modification comprises substitution of the amino acid with a lysine residue. In one embodiment, said modification comprises substitution of the amino acid with an arginine residue.

In one embodiment, wherein the engineered clostridial toxin is a BoNT/E, said engineered BoNT/E comprises a modification of a least one (for example, at least 1, 2, or all 3) amino acid selected from: Q123, N138, and Q237; and said amino acid modification(s) increase(s) the isoelectric point (pI) of the engineered BoNT/E to a value that is at least 0.2 (for example, at least 0.2, 0.3, 0.4, 0.5, 0.6, 0.7, 0.8, 0.9 or 1) pI units higher than the pI of an otherwise identical BoNT/E lacking said amino acid modification(s). In one embodiment said modification comprises substitution of the amino acid with a lysine residue or an arginine residue. In one embodiment, said modification comprises substitution of the amino acid with a lysine residue. In one embodiment, said modification comprises substitution of the amino acid with an arginine residue.

The present inventors have identified certain amino acids that represent preferred targets for amino acid modification in a BoNT/F clostridial toxin light chain.

In one embodiment, wherein the engineered clostridial toxin is a BoNT/F, said engineered BoNT/F comprises a modification of at least one (for example, at least 1, 2, 3, 4, 5, 10, 15, 20, 30, or all 35) amino acid selected from: N6, N9, N11, D12, N15, D16, D17, E28, D55, D60, D74, N76, E105, E121, N126, E127, N144, D185, N211, Q252, N305, E310, D312, N314, N329, D331, N379, D382, D383, D384, E390, N396, N400, D414, and D418; and said amino acid modification(s) increase(s) the isoelectric point (pI) of the engineered BoNT/F to a value that is at least 0.2 (for example, at least 0.2, 0.3, 0.4, 0.5, 0.6, 0.7, 0.8, 0.9 or 1) pI units higher than the pI of an otherwise identical BoNT/F lacking said amino acid modification(s). In one embodiment said modification comprises substitution of the amino acid with a lysine residue or an arginine residue. In one embodiment, said modification comprises substitution of the amino acid with a lysine residue. In one embodiment, said modification comprises substitution of the amino acid with an arginine residue.

The present inventors have identified certain amino acids that represent preferred targets for amino acid modification in a BoNT/G clostridial toxin light chain.

In one embodiment, wherein the engineered clostridial toxin is a BoNT/G, said engineered BoNT/G comprises a modification of at least one (for example, at least 1, 2, 3, 4, 5, 10, 15, 20, 30, 35, or all 38) amino acid selected from: N4, N7, N9, N11, D12, N15, D17, E48, Q55, D57, N60, D75, D127, Q144, E148, D149, Q150, N178, E185, E208, D211, E255, D315, D332, N334, D340, E383, D387, N388, Q393, N394, E395, N403, E407, E418, E422, E426, and N443; and said amino acid modification(s) increase(s) the isoelectric point (pI) of the engineered BoNT/G to a value that is at least 0.2 (for example, at least 0.2, 0.3, 0.4, 0.5, 0.6, 0.7, 0.8, 0.9 or 1) pI units higher than the pI of an otherwise identical BoNT/G lacking said amino acid modification(s). In one embodiment said modification comprises substitution of the amino acid with a lysine residue or an arginine residue. In one embodiment, said modification comprises substitution of the amino acid with a lysine residue. In one embodiment, said modification comprises substitution of the amino acid with an arginine residue.

The present inventors have identified certain amino acids that represent preferred targets for amino acid modification in a TeNT light chain.

In one embodiment, wherein the engineered clostridial toxin is a TeNT, said engineered TeNT comprises a modification of at least one (for example, at least 1, 2, 3, 4, 5, 10, 15, 20, 30, 35, or all 36) amino acid selected from: N6, N7, N15, N16, D17, D31, E51, E57, N60, N76, N101, D126, D143, N167, D179, N180, E251, Q257, N313, N316, D318, D335, N337, Q339, N368, N387, D390, D391, N395, D396, E403, D406, E410, N421, D427, and E450; and said amino acid modification(s) increase(s) the isoelectric point (pI) of the engineered TeNT to a value that is at least 0.2 (for example, at least 0.2, 0.3, 0.4, 0.5, 0.6, 0.7, 0.8, 0.9 or 1) pI units higher than the pI of an otherwise identical TeNT lacking said amino acid modification(s). In one embodiment said modification comprises substitution of the amino acid with a lysine residue or an arginine residue. In one embodiment, said modification comprises substitution of the amino acid with a lysine residue. In one embodiment, said modification comprises substitution of the amino acid with an arginine residue.

The present invention is suitable for application to many different varieties of clostridial toxin. Thus, in the context of the present invention, the term "clostridial toxin" embraces toxins produced by *C. botulinum* (botulinum neurotoxin serotypes A, B, C$_1$, D, E, F and G), *C. tetani* (tetanus neurotoxin), *C. butyricum* (botulinum neurotoxin serotype E), and *C. baratii* (botulinum neurotoxin serotype F), as well as modified clostridial toxins or derivatives derived from any of the foregoing. The term "clostridial toxin" also embraces botulinum neurotoxin serotype H.

Botulinum neurotoxin (BoNT) is produced by *C. botulinum* in the form of a large protein complex, consisting of BoNT itself complexed to a number of accessory proteins. There are at present eight different classes of botulinum neurotoxin, namely: botulinum neurotoxin serotypes A, B, C$_1$, D, E, F, G, and H, all of which share similar structures and modes of action. Different BoNT serotypes can be distinguished based on inactivation by specific neutralising anti-sera, with such classification by serotype correlating with percentage sequence identity at the amino acid level. BoNT proteins of a given serotype are further divided into different subtypes on the basis of amino acid percentage sequence identity.

BoNTs are absorbed in the gastrointestinal tract, and, after entering the general circulation, bind to the presynaptic membrane of cholinergic nerve terminals and prevent the release of their neurotransmitter acetylcholine. BoNT/B, BoNT/D, BoNT/F and BoNT/G cleave synaptobrevin/vesicle-associated membrane protein (VAMP); BoNT/C$_1$, BoNT/A and BoNT/E cleave the synaptosomal-associated protein of 25 kDa (SNAP-25); and BoNT/C$_1$ cleaves syntaxin.

Tetanus toxin is produced in a single serotype by *C. tetani*. *C. butyricum* produces BoNT/E, while *C. baratii* produces BoNT/F.

The term "clostridial toxin" is also intended to embrace modified clostridial toxins and derivatives thereof, including but not limited to those described below. A modified clostridial toxin or derivative may contain one or more amino acids that has been modified as compared to the native (unmodified) form of the clostridial toxin, or may contain one or more inserted amino acids that are not present in the native (unmodified) form of the clostridial toxin. By way of example, a modified clostridial toxin may have modified amino acid sequences in one or more domains relative to the native (unmodified) clostridial toxin sequence. Such modifications may modify functional aspects of the toxin, for example biological activity or persistence. Thus, in one embodiment, the engineered clostridial toxin of the invention is an engineered modified clostridial toxin, or an engineered modified clostridial toxin derivative, or an engineered clostridial toxin derivative.

A modified clostridial toxin may have one or more modifications in the amino acid sequence of the heavy chain (such as a modified H$_C$ domain), wherein said modified heavy chain binds to target nerve cells with a higher or lower affinity than the native (unmodified) clostridial toxin. Such modifications in the H$_C$ domain can include modifying residues in the ganglioside binding site of the H$_C$ domain or in the protein (SV2 or synaptotagmin) binding site that alter binding to the ganglioside receptor and/or the protein receptor of the target nerve cell. Examples of such modified clostridial toxins are described in WO 2006/027207 and WO 2006/114308, both of which are hereby incorporated by reference in their entirety.

A modified clostridial toxin may have one or more modifications in the amino acid sequence of the light chain, for example modifications in the substrate binding or catalytic domain which may alter or modify the SNARE protein specificity of the modified LC. Examples of such modified clostridial toxins are described in WO 2010/120766 and US 2011/0318385, both of which are hereby incorporated by reference in their entirety.

A modified clostridial toxin may comprise one or more modifications that increases or decreases the biological activity and/or the biological persistence of the modified clostridial toxin. For example, a modified clostridial toxin may comprise a leucine- or tyrosine-based motif, wherein said motif increases or decreases the biological activity and/or the biological persistence of the modified clostridial toxin. Suitable leucine-based motifs include xDxxxLL, xExxxLL, xExxxLL, and xExxxLM (wherein x is any amino acid). Suitable tyrosine-based motifs include Y-x-x-Hy (wherein Hy is a hydrophobic amino acid). Examples of modified clostridial toxins comprising leucine- and tyrosine-based motifs are described in WO 2002/08268, which is hereby incorporated by reference in its entirety.

The term "clostridial toxin" is intended to embrace hybrid and chimeric clostridial toxins. A hybrid clostridial toxin comprises at least a portion of a light chain from one clostridial toxin or subtype thereof, and at least a portion of a heavy chain from another clostridial toxin or clostridial toxin subtype. In one embodiment the hybrid clostridial toxin may contain the entire light chain from one clostridial toxin subtype and the heavy chain from another clostridial toxin subtype. In another embodiment, a chimeric clostridial toxin may contain a portion (e.g. the binding domain) of the heavy chain of one clostridial toxin subtype, with another portion of the heavy chain being from another clostridial toxin subtype. Similarly or alternatively, the therapeutic element may comprise light chain portions from different clostridial toxins. Such hybrid or chimeric clostridial toxins are useful, for example, as a means of delivering the therapeutic benefits of such clostridial toxins to patients who are immunologically resistant to a given clostridial toxin subtype, to patients who may have a lower than average concentration of receptors to a given clostridial toxin heavy chain binding domain, or to patients who may have a protease-resistant variant of the membrane or vesicle toxin substrate (e.g., SNAP-25, VAMP and syntaxin). Hybrid and chimeric clostridial toxins are described in U.S. Pat. No. 8,071,110, which publication is hereby incorporated by reference in its entirety. Thus, in one embodiment, the engineered clostridial toxin of the invention is an engineered hybrid clostridial toxin, or an engineered chimeric clostridial toxin.

The term "clostridial toxin" is intended to embrace re-targeted clostridial toxins. In a re-targeted clostridial toxin, the clostridial toxin is modified to include an exogenous ligand known as a Targeting Moiety (TM). The TM is selected to provide binding specificity for a desired target cell, and as part of the re-targeting process the native binding portion of the clostridial toxin (e.g. the $H_C$ domain, or the $H_{CC}$ domain) may be removed. Re-targeting technology is described, for example, in: EP-B-0689459; WO 1994/021300; EP-B-0939818; U.S. Pat. Nos. 6,461,617; 7,192,596; WO 1998/007864; EP-B-0826051; U.S. Pat. Nos. 5,989,545; 6,395,513; 6,962,703; WO 1996/033273; EP-B-0996468; U.S. Pat. No. 7,052,702; WO 1999/017806; EP-B-1107794; U.S. Pat. No. 6,632,440; WO 2000/010598; WO 2001/21213; WO 2006/059093; WO 2000/62814; WO 2000/04926; WO 1993/15766; WO 2000/61192; and WO 1999/58571; all of which are hereby incorporated by reference in their entirety. Thus, in one embodiment, the engineered clostridial toxin of the invention is an engineered re-targeted clostridial toxin.

The present invention also embraces clostridial toxins that have a non-native protease cleavage site. In such clostridial toxins, the native protease cleavage site (also known as the activation site, as described above) is modified or replaced with a protease cleavage site that is not native to that clostridial toxin (i.e. an exogenous cleavage site). Such a site will require an exogenous protease for cleavage, which allows for improved control over the timing and location of cleavage events. Non-native protease cleavage sites that may be employed in clostridial toxins include:

| Enterokinase | (DDDDK↓) |
|---|---|
| Factor Xa | (IEGR↓/IDGR↓) |
| TEV (Tobacco Etch virus) | (ENLYFQ↓G) |
| Thrombin | (LVPR↓GS) |
| PreScission | (LEVLFQ↓GP). |

Additional protease cleavage sites include recognition sequences that are cleaved by a non-cytotoxic protease, for example by the light chain of a clostridial neurotoxin. These include the SNARE (e.g. SNAP-25, syntaxin, VAMP) protein recognition sequences that are cleaved by non-cytotoxic proteases such as the light chain of a clostridial neurotoxin. Clostridial toxins comprising non-native protease cleavage sites are described in U.S. Pat. No. 7,132,259, EP 1206554-B2 and US 2007/0166332, all of which are hereby incorporated by reference in their entirety. Also embraced by the term protease cleavage site is an intein, which is a self-cleaving sequence. The self-splicing reaction is controllable, for example by varying the concentration of reducing agent present.

The present invention also embraces clostridial toxins comprising a "destructive cleavage site". In said clostridial toxins, a non-native protease cleavage site is incorporated into the clostridial toxin, at a location chosen such that cleavage at said site will decrease the activity of, or inactivate, the clostridial toxin. The destructive protease cleavage site can be susceptible to cleavage by a local protease, in the event that the clostridial toxin, following administration, migrates to a non-target location. Suitable non-native protease cleavage sites include those described above. Clostridial toxins comprising a destructive cleavage site are described in WO 2010/094905 and WO 2002/044199, both of which are hereby incorporated by reference in their entirety.

The engineered clostridial toxins of the present invention, especially the light chain component thereof, may be PEGylated—this may help to increase stability, for example duration of action of the light chain component. PEGylation is particularly preferred when the light chain comprises a BoNT/A, B or $C_1$ protease. PEGylation preferably includes the addition of PEG to the N-terminus of the light chain component. By way of example, the N-terminus of a light chain may be extended with one or more amino acid (e.g. cysteine) residues, which may be the same or different. One or more of said amino acid residues may have its own PEG molecule attached (e.g. covalently attached) thereto. An example of this technology is described in WO2007/104567, which is hereby incorporated by reference in its entirety.

The engineered clostridial toxins of the present invention may be free from the complexing proteins that are present in a naturally occurring clostridial toxin complex.

An engineered clostridial toxin of the present invention may also comprise a limited number of non-standard amino acids. Thus, in addition to the 20 standard amino acids, non-standard amino acids (such as 4-hydroxyproline, 6-N-methyl lysine, 2-aminoisobutyric acid, isovaline and α-methyl serine) may be substituted for amino acid residues of the engineered clostridial toxins of the present invention. A limited number of non-conservative amino acids, amino acids that are not encoded by the genetic code, and unnatural amino acids may be substituted for clostridial polypeptide amino acid residues. The engineered clostridial toxins of the present invention can also comprise non-naturally occurring amino acid residues.

Non-naturally occurring amino acids include, without limitation, trans-3-methylproline, 2,4-methano-proline, cis-4-hydroxyproline, trans-4-hydroxy-proline, N-methylglycine, allo-threonine, methyl-threonine, hydroxy-ethylcysteine, hydroxyethylhomo-cysteine, nitro-glutamine, homoglutamine, pipecolic acid, tert-leucine, norvaline, 2-azaphenylalanine, 3-azaphenyl-alanine, 4-azaphenyl-alanine, and 4-fluorophenylalanine. Several methods are known in the art for incorporating non-naturally occurring amino acid residues into proteins. For example, an in vitro system can be employed wherein nonsense mutations are suppressed using chemically aminoacylated suppressor tRNAs. Methods for synthesizing amino acids and aminoacylating tRNA are known in the art. Transcription and translation of plasmids containing nonsense mutations is carried out in a cell free system comprising an *E. coli* S30 extract and commercially available enzymes and other reagents. Proteins are purified by chromatography. See, for example, Robertson et al., *J. Am. Chem. Soc.* 113:2722, 1991; Ellman et al., *Methods Enzymol.* 202:301, 1991; Chung et al., *Science* 259:806-9, 1993; and Chung et al., *Proc. Natl. Acad. Sci. USA* 90:10145-9, 1993). In a second method, translation is carried out in *Xenopus* oocytes by microinjection of mutated mRNA and chemically aminoacylated suppressor tRNAs (Turcatti et al., *J. Biol. Chem.* 271:19991-8, 1996). Within a third method, *E. coli* cells are cultured in the absence of a natural amino acid that is to be replaced (e.g., phenylalanine) and in the presence of the desired non-naturally occurring amino acid(s) (e.g., 2-azaphenylalanine, 3-azaphenylalanine, 4-azaphenylalanine, or 4-fluorophenylalanine). The non-naturally occurring amino acid is incorporated into the polypeptide in place of its natural counterpart. See, Koide et al., Biochem. 33:7470-6, 1994.

The engineered clostridial toxins of the present invention can be produced using recombinant nucleic acid technologies. Thus, in one embodiment, an engineered clostridial toxin (as described above) is a recombinant engineered clostridial toxin.

In another aspect, the present invention provides a nucleic acid (for example, a DNA) comprising a nucleic acid sequence encoding an engineered clostridial toxin as described above. In one embodiment, the nucleic acid sequence is prepared as part of a DNA vector comprising a promoter and a terminator.

In a preferred embodiment, the vector has a promoter selected from:

| Promoter | Induction Agent | Typical Induction Condition |
| --- | --- | --- |
| Tac (hybrid) | IPTG | 0.2 mM (0.05-2.0 mM) |
| AraBAD | L-arabinose | 0.2% (0.002-0.4%) |
| T7-lac operator | IPTG | 0.2 mM (0.05-2.0 mM) |

In another preferred embodiment, the vector has a promoter selected from:

| Promoter | Induction Agent | Typical Induction Condition |
| --- | --- | --- |
| Tac (hybrid) | IPTG | 0.2 mM (0.05-2.0 mM) |
| AraBAD | L-arabinose | 0.2% (0.002-0.4%) |
| T7-lac operator | IPTG | 0.2 mM (0.05-2.0 mM) |
| T5-lac operator | IPTG | 0.2 mM (0.05-2.0 mM) |

The nucleic acid molecules of the invention may be made using any suitable process known in the art. Thus, the nucleic acid molecules may be made using chemical synthesis techniques. Alternatively, the nucleic acid molecules of the invention may be made using molecular biology techniques.

The DNA construct of the present invention is preferably designed in silico, and then synthesised by conventional DNA synthesis techniques.

The above-mentioned nucleic acid sequence information is optionally modified for codon-biasing according to the ultimate host cell (e.g. E. coli) expression system that is to be employed.

In one embodiment, the nucleic acid sequence encoding an engineered clostridial toxin as described above is a nucleic acid sequence having at least 70% (for example, at least 75, 80, 85, 90, 95, 97, 98 or 99%) sequence identity to a nucleic acid sequence selected from SEQ ID NOs: 2, 4, and 6. In one embodiment, the nucleic acid sequence has at least 90% sequence identity to a nucleic acid sequence selected from SEQ ID NOs: 2, 4, and 6.

The present invention also provides polypeptides encoded by nucleic acid sequences as described above. Thus, in one aspect, the present invention provides a polypeptide comprising an amino acid sequence having at least 70% (for example, at least 75, 80, 85, 90, 95, 97, 98 or 99%) sequence identity to an amino acid sequence selected from SEQ ID NOs: 1, 3 and 5. In one embodiment, the amino acid sequence has at least 90% sequence identity to an amino acid sequence selected from SEQ ID NOs: 1, 3 and 5.

In one embodiment, the engineered clostridial toxin of the invention is an engineered BoNT/A as described above, and said engineered BoNT/A comprises (or consists of) an amino acid sequence having at least 70% (for example, at least 75, 80, 85, 90, 95, 97, 98, 99, 99.5 or 99.9%) sequence identity to an amino acid sequence selected from SEQ ID NOs: 1, 3 and 5.

In one embodiment, the engineered clostridial toxin of the invention is an engineered BoNT/A as described above, and said engineered BoNT/A comprises (or consists of) the amino acid sequence of SEQ ID NO: 1, 3 or 5.

In one aspect, the invention provides a polypeptide comprising (or consisting of) the amino acid sequence of SEQ ID NO: 1, 3 or 5.

In one aspect, the invention provides a nucleic acid encoding an engineered clostridial toxin as described above, wherein said nucleic acid comprises a nucleic acid sequence having at least 70% (for example, at least 75, 80, 85, 90, 95, 97, 98, 99, 99.5 or 99.9%) sequence identity to a nucleic acid sequence selected from SEQ ID NOs: 2, 4 and 6. In one embodiment, the nucleic acid comprises (or consists of) the nucleic acid sequence of SEQ ID NO: 2, 4 or 6.

In one aspect, the invention provides a nucleic acid comprising (or consisting of) the nucleic acid sequence of SEQ ID NO: 2, 4 or 6.

In one embodiment, the engineered clostridial toxin of the invention is an engineered BoNT/E as described above, and said engineered BoNT/E comprises an amino acid sequence having at least 70% (for example, at least 75, 80, 85, 90, 95, 97, 98, 99, 99.5 or 99.9%) sequence identity to SEQ ID NO: 7.

In one aspect, the invention provides a nucleic acid encoding an engineered clostridial toxin as described above, wherein said nucleic acid comprises a nucleic acid sequence having at least 70% (for example, at least 75, 80, 85, 90, 95, 97, 98, 99, 99.5 or 99.9%) sequence identity to SEQ ID NO: 8.

The "percent sequence identity" between two or more nucleic acid or amino acid sequences is a function of the number of identical positions shared by the sequences. Thus, % identity may be calculated as the number of identical nucleotides/amino acids divided by the total number of nucleotides/amino acids, multiplied by 100. Calculations of % sequence identity may also take into account the number of gaps, and the length of each gap that needs to be introduced to optimize alignment of two or more sequences. Sequence comparisons and the determination of percent identity between two or more sequences can be carried out using specific mathematical algorithms, such as BLAST, which will be familiar to a skilled person.

In one aspect, the present invention provides a method of producing a single-chain engineered clostridial toxin protein having a light chain and a heavy chain, the method comprising expressing a nucleic acid (said nucleic acid being as described above) in a suitable host cell, lysing the host cell to provide a host cell homogenate containing the single-chain engineered clostridial toxin protein, and isolating the single-chain engineered clostridial toxin protein.

In another aspect, the present invention provides a method of activating an engineered clostridial toxin, the method comprising providing a single-chain engineered clostridial toxin protein obtainable by the method of producing a single-chain engineered clostridial toxin protein as described above, contacting the polypeptide with a protease that cleaves the polypeptide at a recognition site (cleavage site) located between the light chain and heavy chain, thereby converting the polypeptide into a di-chain polypeptide wherein the light chain and heavy chain are joined together by a disulphide bond.

The engineered clostridial toxins of the invention may be used to prevent or treat certain medical or cosmetic diseases and conditions. Thus, in a further aspect, the present invention provides an engineered clostridial toxin as described above, for use in medicine.

In a related aspect, the present invention provides an engineered clostridial toxin as described above, for use in the prevention or treatment of a disease or condition selected from: strabismus, blepharospasm, squint, dystonia (e.g. spasmodic dystonia, oromandibular dystonia, focal dystonia, tardive dystonia, laryngeal dystonia, limb dystonia, cervical dystonia), torticollis (e.g. spasmodic torticollis), beauty therapy (cosmetic) applications benefiting from cell/muscle incapacitation (via SNARE down-regulation or inactivation), neuromuscular disorder or condition of ocular motility (e.g. concomitant strabismus, vertical strabismus, lateral rectus palsy, nystagmus, dysthyroid myopathy), writer's cramp, blepharospasm, bruxism, Wilson's disease, tremor, tics, segmental myoclonus, spasms, spasticity due to chronic multiple sclerosis, spasticity resulting in abnormal bladder control, animus, back spasm, charley horse, tension headaches, levator pelvic syndrome, spina bifida, tardive dyskinesia, Parkinson's disease, stuttering, hemifacial spasm, eyelid disorder, cerebral palsy, focal spasticity, spasmodic colitis, neurogenic bladder, anismus, limb spasticity, tics, tremors, bruxism, anal fissure, achalasia, dysphagia, lacrimation, hyperhydrosis, excessive salivation, excessive gastrointestinal secretions, muscle pain (e.g. pain from muscle spasms), headache pain (e.g. tension headache), brow furrows, skin wrinkles, cancer, uterine disorders, urogenital disorders, urogenital-neurological disorders, chronic neurogenic inflammation, and a smooth muscle disorder.

In use, the present invention employs a pharmaceutical composition, comprising an engineered clostridial toxin, together with at least one component selected from a pharmaceutically acceptable carrier, excipient, adjuvant, propellant and/or salt.

The engineered clostridial toxins of the present invention may be formulated for oral, parenteral, continuous infusion, inhalation or topical application. Compositions suitable for injection may be in the form of solutions, suspensions or emulsions, or dry powders which are dissolved or suspended in a suitable vehicle prior to use.

In the case of an engineered clostridial toxin that is to be delivered locally, the engineered clostridial toxin may be formulated as a cream (e.g. for topical application), or for sub-dermal injection.

Local delivery means may include an aerosol, or other spray (e.g. a nebuliser). In this regard, an aerosol formulation of an engineered clostridial toxin enables delivery to the lungs and/or other nasal and/or bronchial or airway passages.

Engineered clostridial toxins of the invention may be administered to a patient by intrathecal or epidural injection in the spinal column at the level of the spinal segment involved in the innervation of an affected organ.

A preferred route of administration is via laparoscopic and/or localised, particularly intramuscular, injection.

The dosage ranges for administration of the engineered clostridial toxins of the present invention are those to produce the desired therapeutic effect. It will be appreciated that the dosage range required depends on the precise nature of the engineered clostridial toxin or composition, the route of administration, the nature of the formulation, the age of the patient, the nature, extent or severity of the patient's condition, contraindications, if any, and the judgement of the attending physician. Variations in these dosage levels can be adjusted using standard empirical routines for optimisation.

Suitable daily dosages (per kg weight of patient) are in the range 0.0001-1 ng/kg, preferably 0.0001-0.5 ng/kg, more preferably 0.002-0.5 ng/kg, and particularly preferably 0.004-0.5 ng/kg. The unit dosage can vary from less than 1 picogram to 30 ng, but typically will be in the region of 0.01 to 1 ng per dose, which may be administered daily or preferably less frequently, such as weekly or six monthly.

A particularly preferred dosing regimen is based on 0.05 ng of engineered clostridial toxin as the 1× dose. In this regard, preferred dosages are in the range 1×-100× (i.e. 0.05-5 ng).

Fluid dosage forms are typically prepared utilising the engineered clostridial toxin and a pyrogen-free sterile vehicle. The engineered clostridial toxin, depending on the vehicle and concentration used, can be either dissolved or suspended in the vehicle. In preparing solutions the engineered clostridial toxin can be dissolved in the vehicle, the solution being made isotonic if necessary by addition of sodium chloride and sterilised by filtration through a sterile filter using aseptic techniques before filling into suitable sterile vials or ampoules and sealing. Alternatively, if solution stability is adequate, the solution in its sealed containers may be sterilised by autoclaving. Advantageously additives such as buffering, solubilising, stabilising, preservative or bactericidal, suspending or emulsifying agents and or local anaesthetic agents may be dissolved in the vehicle.

Dry powders, which are dissolved or suspended in a suitable vehicle prior to use, may be prepared by filling pre-sterilised ingredients into a sterile container using aseptic technique in a sterile area. Alternatively the ingredients may be dissolved into suitable containers using aseptic technique in a sterile area. The product is then freeze dried and the containers are sealed aseptically.

Parenteral suspensions, suitable for intramuscular, subcutaneous or intradermal injection, are prepared in substantially the same manner, except that the sterile components are suspended in the sterile vehicle, instead of being dissolved and sterilisation cannot be accomplished by filtration. The components may be isolated in a sterile state or alternatively it may be sterilised after isolation, e.g. by gamma irradiation.

Advantageously, a suspending agent for example polyvinylpyrrolidone is included in the composition(s) to facilitate uniform distribution of the components.

Administration in accordance with the present invention may take advantage of a variety of delivery technologies including microparticle encapsulation, viral delivery systems or high-pressure aerosol impingement.

FIGURE LEGENDS

FIG. 1.

SDS-PAGE purification of $CatH_N$_v1 (FIG. 1A), $CatH_N$_v2 (FIG. 1B), and $CatH_N$_v3 (FIG. 1C) purification.

FIG. 2.

Percentage SNAP-25 cleavage in rat embryonic spinal cord neurons (eSCN) for $CatH_N$_v1. Rat embryonic spinal cord neurons were cultured for three weeks and treated with $CatH_N$_v1 for 24 h, before Western blotting with SNAP-25 specific antibody. Data is mean±SEM from three independent experiments in triplicate.

FIG. 3.

The potency ($t_{50}$) of BoNT/A and $CatH_N$_v1 in the mouse phrenic nerve hemi-diaphragm assay (mPNHD). Data points are individual hemi-diaphragm preparations and means±SEM. CatH$_N$_v1 was statistically significantly slower than reference protein BoNT/A (List Biological Laboratories). 1-way ANOVA and Dunnett's multiple comparisons test. p<0.01, *p<0.001, ****p<0.0001 (1-way ANOVA and Dunnett's multiple comparisons test).

FIG. 4.

Percentage SNAP-25 cleavage in rat embryonic spinal cord neurons (eSCN) for CatH$_N$_v2. Rat embryonic spinal cord neurons were cultured for three weeks and treated with CatH$_N$_v2 for 24 h, before Western blotting with SNAP-25 specific antibody. Data is mean±SEM from three independent experiments in triplicate.

FIG. 5.

The potency ($t_{50}$) of BoNT/A and CatH$_N$_v2 in the mouse phrenic nerve hemi-diaphragm assay (mPNHD). Data points are individual hemi-diaphragm preparations and means±SEM. CatH$_N$_v2 is statistically equivalent to the reference protein BoNT/A (List Biological Laboratories). 1-way ANOVA and Dunnett's multiple comparisons test. p<0.01, *p<0.001, ****p<0.0001 (1-way ANOVA and Dunnett's multiple comparisons test).

FIG. 6.

Percentage SNAP-25 cleavage in rat embryonic spinal cord neurons (eSCN) for CatH$_N$_v3. Rat embryonic spinal cord neurons were cultured for three weeks and treated with CatH$_N$_v3 for 24 h, before Western blotting with SNAP-25 specific antibody. Data is mean±SEM from three independent experiments in triplicate.

FIG. 7.

The potency ($t_{50}$) of BoNT/A and CatH$_N$_v3 in the mouse phrenic nerve hemi-diaphragm assay (mPNHD). Data points are individual hemi-diaphragm preparations and means±SEM. CatH$_N$_v3 was statistically significantly slower than the reference protein BoNT/A (List Biological Laboratories). 1-way ANOVA and Dunnett's multiple comparisons test. p<0.01, *p<0.001, ****p<0.0001 (1-way ANOVA and Dunnett's multiple comparisons test).

FIG. 8.

Isoelectric focusing analysis. All three CatH$_N$ constructs possess an increased observed p/compared to unmodified BoNT/A.

FIG. 9.

SDS-PAGE purification of CatLC construct.

FIG. 10.

Catalytic activity of CatLC compared to BoNT/E LC reference, with pEC$_{50}$ values obtained in the BoTest A/E BoNT Detection Kit (BioSentinal Cat # A1004), following manufacturer's instructions. Data shows mean±standard deviation from one independent experiment in triplicate.

SEQUENCES

SEQ ID NO: 1. Engineered BoNT/A, "CatH$_N$_v1", amino acid sequence.
SEQ ID NO: 2. Engineered BoNT/A, "CatH$_N$_v1", nucleic acid sequence.
SEQ ID NO: 3. Engineered BoNT/A, "CatH$_N$_v2", amino acid sequence.
SEQ ID NO: 4. Engineered BoNT/A, "CatH$_N$_v2", nucleic acid sequence.
SEQ ID NO: 5. Engineered BoNT/A, "CatH$_N$_v3", amino acid sequence.
SEQ ID NO: 6. Engineered BoNT/A, "CatH$_N$_v3", nucleic acid sequence.
SEQ ID NO: 7. Engineered BoNT/E light chain, "CatLC", amino acid sequence.
SEQ ID NO: 8. Engineered BoNT/E light chain, "CatLC", nucleic acid sequence.

```
SEQ ID NO: 1. Engineered BoNT/A, "CatH_N_v1",
amino acid sequence.
MPFVNKQFNYKDPVNGVDIAYIKIPNAGQMQPVKAFKIHNKIWVIPERDT
FTNPEEGDLNPPPEAKQVPVSYYDSTYLSTDNEKDNYLKGVTKLFERIYS
TDLGRMLLTSIVRGIPFWGGSTIDTELKVIDTNCINVIQPDGSYRSEELN
LVIIGPSADIIQFECKSFGHEVLNLTRNGYGSTQYIRFSPDFTFGFEESL
EVDTNPLLGAGKFATDPAVTLAHELIHAGHRLYGIAINPNRVFKVNTNAY
YEMSGLEVSFEELRTFGGHDAKFIDSLQENEFRLYYYNKFKDIASTLNKA
KSIVGTTASLQYMKNVFKEKYLLSEDTSGKFSVDKLKFDKLYKMLTEIYT
EDNFVKFFKVLNRKTYLNFDKAVFKINIVPKVNYTIYDGFNLRNTNLAAN
FNGQNTEINNMNFTKLKNFTGLFEFYKLLCVRGIITSKTKSLDKGYNKAL
NDLCIKVNNWDLFFSPSEDNFTNDLNKGEEITSDTNIEAAEENISLDLIQ
QYYLTFNFDNEPENISIENLSSDIIGQLELMPNIERFPNGKKYELDKYTM
FHYLRAQEFEHGKRRIALTNSVNEALLNPSRVYTFFSSDYVKKVNKATEA
AMFLGWVEQLVYDFTDETSEVSTTDKIADITIIIPYIGPALNIGNMRYKR
RFVGALIFSGAVILLEFIPEIAIPVLGTFALVSYIANKVLTVQTIDNALS
KRNEKWDEVYKYIVTNWLAKVNTQIDLIRKKMKEALENQAEATKAIINYQ
YNQYTEEEKNNINFNIDDLSSKLNESINKAMININKFLNQCSVSYLMNSM
IPYGVKRLEDFDASLKDALLKYIYDNRGTLIGQVDRLKDKVNNTLSRDRP
FQLSKYVDNQRLLSTFTEYIKNIINTSILNLRYESNHLIDLSRYASKINI
GSKVNFDPIDKNQIQLFNLESSKIEVILKNAIVYNSMYENFSTSFWIRIP
KYFNSISLNNEYTIINCMENNSGWKVSLNYGEIIWTLQDTQEIKQRVVFK
YSQMINISDYINRWIFVTITNNRLNNSKIYINGRLIDQKPISNLGNIHAS
NNIMFKLDGCRDTHRYIWIKYFNLFDKELNEKEIKDLYDNQSNSGILKDF
WGDYLQYDKPYYMLNLYDPNKYVDVNNVGIRGYMYLKGPRGSVMTTNIYL
NSSLYRGTKFIIKKYASGNKDNIVRNNDRVYINVVVKNKEYRLATNASQA
GVEKILSALEIPDVGNLSQVVVMKSKNDQGITNKCKMNLQDNNGNDIGFI
GFHQFNNIAKLVASNWYNRQIERSSRTLGCSWEFIPVDDGWGERPL SEQ ID NO: 2. Engineered BoNT/A, "CatH_N_v1",
nucleic acid sequence.
ATGCCATTCGTCAACAAGCAATTCAACTACAAAGACCCAGTCAACGGCGT
CGACATCGCATACATCAAGATTCCGAACGCCGGTCAAATGCAGCCGGTTA
AGGCTTTTAAGATCCACAACAAGATTTGGGTTATCCCGGAGCGTGACACC
TTCACGAACCCGGAAGAAGGCGATCTGAACCCGCCACCGGAAGCGAAGCA
AGTCCCTGTCAGCTACTACGATTCGACGTACCTGAGCACGGATAACGAAA
AAGATAACTACCTGAAAGGTGTGACCAAGCTGTTCGAACGTATCTACAGC
ACGGATCTGGGTCGCATGCTGCTGACTAGCATTGTTCGCGGTATCCCGTT
CTGGGGTGGTAGCACGATTGACACCGAACTGAAGGTTATCGACACTAACT
GCATTAACGTTATCCAACCGGATGGTAGCTATCGTAGCGAAGAGCTGAAT
CTGGTCATCATTGGCCCGAGCGCAGACATTATCCAATTCGAGTGCAAGAG
CTTTGGTCACGAGGTTCTGAATCTGACCCGCAATGGCTATGGTAGCACCC
```

-continued

```
AGTACATTCGTTTTTCGCCGGATTTTACCTTCGGCTTTGAAGAGAGCCTG
GAGGTTGATACCAATCCGTTGCTGGGTGCGGGCAAATTCGCTACCGATCC
GGCTGTCACGCTGGCCCATGAACTGATCCACGCAGGCCACCGCCTGTACG
GCATTGCCATCAACCCAAACCGTGTGTTCAAGGTTAATACGAATGCATAC
TACGAGATGAGCGGCCTGGAAGTCAGCTTCGAAGAACTGCGCACCTTCGG
TGGCCATGACGCTAAATTCATTGACAGCTTGCAAGAGAATGAGTTCCGTC
TGTACTACTATAACAAATTCAAAGACATTGCAAGCACGTTGAACAAGGCC
AAAAGCATCGTTGGTACTACCGCTCGTTGCAGTATATGAAGAATGTGTT
TAAAGAGAAGTACCTGCTGTCCGAGGATACCTCCGGCAAGTTTAGCGTTG
ATAAGCTGAAGTTTGACAAACTGTACAAGATGCTGACCGAGATTTACACC
GAGGACAACTTTGTGAAATTCTTCAAAGTGTTGAATCGTAAAACCTATCT
GAATTTTGACAAAGCGGTTTTCAAGATTAACATCGTGCCGAAGGTGAACT
ACACCATCTATGACGGTTTTAACCTGCGTAACACCAACCTGGCGGCGAAC
TTTAACGGTCAGAATACGGAAATCAACAACATGAATTTCACGAAGTTGAA
GAACTTCACGGGTCTGTTCGAGTTCTATAAGCTGCTGTGCGTGCGCGGTA
TCATCACCAGCAAAACCAAAGCCTGGACAAAGGCTACAACAAGGCGCTG
AATGACCTGTGCATTAAGGTAAACAATTGGGATCTGTTCTTTTCGCCATC
CGAAGATAATTTTACCAACGACCTGAACAAGGGTGAAGAAATCACCAGCG
ATACGAATATTGAAGCAGCGGAAGAGAATATCAGCCTGGATCTGATCCAG
CAGTACTATCTGACCTTTAACTTCGACAATGAACCGGAGAACATTAGCAT
TGAGAATCTGAGCAGCGACATTATCGGTCAGCTGGAACTGATGCCAATA
TCGAACGTTTCCCGAACGGCAAAAAGTACGAGCTGGACAAGTACACTATG
TTCCATTACCTGCGTGCACAGGAGTTTGAACACGGTAAAcgtCGTATCGC
GCTGACCAACAGCGTTAACGAGGCCCTGCTGAACCCGAGCCGTGTCTATA
CCTTCTTCAGCAGCGACTATGTTAAGAAAGTGAACAAAGCCACTGAGGCC
GCGATGTTCCTGGGCTGGGTGGAACAGCTGGTATATGACTTCACGGACGA
GACGAGCGAAGTGAGCACTACCGACAAAATTGCTGATATTACCATCATTA
TCCCGTATATTGGTCCGGCACTGAACATTGGCAACATGCgtTACAAAcgt
cgTTTTGTGGGTGCCCTGATCTTCTCCGGTGCCGTGATTCTGCTGGAGTT
CATTCCGGAGATTGCGATCCCGGTGTTGGGTACCTTCGCGCTGGTGTCCT
ACATCGCGAATAAGGTTCTGACGGTTCAGACCATCGATAACGCGCTGTCG
AAACGTAATGAAAAATGGGACGAGGTTTACAAATACATTGTTACGAATTG
GCTGGCGAAAGTCAATACCCAGATCGACCTGATCCGTAAGAAAATGAAAG
AGGCGCTGGAGAATCAGGCGGAGGCCACCAAAGCAATTATCAACTACCAA
TACAACCAGTACACGGAAGAAGAGAAGAATAACATTAACTTCAATATCGA
TGATTTGAGCAGCAAGCTGAATGAATCTATCAACAAAGCGATGATCAATA
TCAACAAGTTTTTGAATCAGTGTAGCGTTTCGTACCTGATGAATAGCATG
ATTCCGTATGGCGTCAAACGTCTGGAGGACTTCGACGCCAGCCTGAAAGA
TGCGTTGCTGAAATACATTTACGACAATCGTGGTACGCTGATTGGCCAAG
TTGACCGCTTGAAAGACAAAGTTAACAATACCCTGAGCcgtgACcgtCCA
```

```
TTTCAACTGAGCAAGTATGTTGATAATCAACGTCTGTTGAGCACTTTCAC
CGAGTATATCAAAAACATCATCAATACTAGCATTCTGAACCTGCGTTACG
AGAGCAATCATCTGATTGATCTGAGCCGTTATGCAAGCAAGATCAACATC
GGTAGCAAGGTCAATTTTGACCCGATCGATAAGAACCAGATCCAGCTGTT
TAATCTGGAATCGAGCAAAATTGAGGTTATCCTGAAAAACGCCATTGTCT
ACAACTCCATGTACGAGAATTTCTCCACCAGCTTCTGGATTCGCATCCCG
AAATACTTCAACAGCATTAGCCTGAACAACGAGTATACTATCATCAACTG
TATGGAGAACAACAGCGGTTGGAAGGTGTCTCTGAACTATGGTGAGATCA
TTTGGACCTTGCAGGACACCCAAGAGATCAAGCAGCGCGTCGTGTTCAAG
TACTCTCAAATGATCAACATTTCCGATTACATTAATCGTTGGATCTTCGT
GACCATTACGAATAACCGTCTGAATAACAGCAAGATTTACATCAATGGTC
GCTTGATCGATCAGAAACCGATTAGCAACCTGGGTAATATCCACGCAAGC
AACAACATTATGTTCAAATTGGACGGTTGCCGCGATACCCATCGTTATAT
CTGGATCAAGTATTTCAACCTGTTTGATAAAGAACTGAATGAGAAGGAAT
CAAAGATTTGTATGACAACCAATCTAACAGCGGCATTTTGAAGGACTTCT
GGGGCGATTATCTGCAATACGATAAGCCGTACTATATGCTGAACCTGTAT
GATCCGAACAAATATGTGGATGTCAATAATGTGGGTATTCGTGGTTACAT
GTATTTGAAGGGTCCGCGTGGCAGCGTTATGACGACCAACATTTACCTGA
ACTCTAGCCTGTACCGTGGTACGAAATTCATCATTAAGAAATATGCCAGC
GGCAACAAAGATAACATTGTGCGTAATAACGATCGTGTCTACATCAACGT
GGTCGTGAAGAATAAAGAGTACCGTCTGGCGACCAACGCTTCGCAGGCGG
GTGTTGAGAAAATTCTGAGCGCGTTGGAGATCCCTGATGTCGGTAATCTG
AGCCAAGTCGTGGTTATGAAGAGCAAGAACGACCAGGGTATCACTAACAA
GTGCAAGATGAACCTGCAAGACAACAATGGTAACGACATCGGCTTTATTG
GTTTCCACCAGTTCAACAATATTGCTAAACTGGTAGCGAGCAATTGGTAC
AATCGTCAGATTGAGCGCAGCAGCCGTACTTTGGGCTGTAGCTGGGAGTT
TATCCCGGTCGATGATGGTTGGGGCGACGTCCGCTG
```

SEQ ID NO: 3. Engineered BoNT/A, "CatH$_N$_v2", amino acid sequence.
MPFVNKQFNYKDPVNGVDIAYIKIPNAGQMQPVKAFKIHNKIWVIPERDT
FTNPEEGDLNPPPEAKQVPVSYYDSTYLSTDNEKDNYLKGVTKLFERIYS
TDLGRMLLTSIVRGIPFWGGSTIDTELKVIDTNCINVIQPDGSYRSEELN
LVIIGPSADIIQFECKSFGHEVLNLTRNGYGSTQYIRFSPDFTFGFEESL
EVDTNPLLGAGKFATDPAVTLAHELIHAGHRLYGIAINPNRVFKVNTNAY
YEMSGLEVSFEELRTFGGHDAKFIDSLQENEFRLYYYNKFKDIASTLNKA
KSIVGTTASLQYMKNVFKEKYLLSEDTSGKFSVDKLKFDKLYKMLTEIYT
EDNFVKFFKVLNRKTYLNFDKAVFKINIVPKVNYTIYDGFNLRNTNLAAN
FNGQNTEINNMNFTKLKNFTGLFEFYKLLCVRGIITSKTKSLDKGYNKAL
NDLCIKVNNWDLFFSPSEDNFTNDLKKGEEITSDTNIEAAEENISLDLIQ
QYYLTFNFDNEPENISIENLSSDIIGQLELMPNIERFPNGKKYELDKYTM
FHYLRAQEFEHGKSRIALTNSVNEALLNPSRVYTFFSSDYVKKVNKATKA
AMFLGWVEQLVYDFTDETSEVSTTDKIADITIIIPYIGPALNIGNMLYKD -continued DFVGALIFSGAVILLEFIPEIAIPVLGTFALVSYIAKKVLTVQTIDNALS
KRNEKWDEVYKYIVTNWLAKVNTQIDLIRKKMKEALENQAEATKAIINYQ
YNQYTEEEKNKIKFNIDDLSSKLNESINKAMININKFLNQCSVSYLMNSM
IPYGVKRLEDFDASLKDALLKYIYDNRGTLKGQVDRLKDKVNNTLSTDIP
FQLSKYVDNQRLLSTFTEYIKNIINTSILNLRYESNHLIDLSRYASKINI
GSKVNFDPIDKNQIQLFNLESSKIEVILKNAIVYNSMYENFSTSFWIRIP
KYFNSISLNNEYTIINCMENNSGWKVSLNYGEIIWTLQDTQEIKQRVVFK
YSQMINISDYINRWIFVTITNNRLNNSKIYINGRLIDQKPISNLGNIHAS
NNIMFKLDGCRDTHRYIWIKYFNLFDKELNEKEIKDLYDNQSNSGILKDF
WGDYLQYDKPYYMLNLYDPNKYVDVNNVGIRGYMYLKGPRGSVMTTNIYL
NSSLYRGTKFIIKKYASGNKDNIVRNNDRVYINVVVKNKEYRLATNASQA
GVEKILSALEIPDVGNLSQVVVMKSKNDQGITNKCKMNLQDNNGNDIGFI
GFHQFNNIAKLVASNWYNRQIERSSRTLGCSWEFIPVDDGWGERPL SEQ ID NO: 4. Engineered BoNT/A, "CatH$_N$_v2",
nucleic acid sequence.
ATGCCATTCGTCAACAAGCAATTCAACTACAAAGACCCAGTCAACGGCGT
CGACATCGCATACATCAAGATTCCGAACGCCGGTCAAATGCAGCCGGTTA
AGGCTTTTAAGATCCACAACAAGATTTGGGTTATCCCGGAGCGTGACACC
TTCACGAACCCGGAAGAAGGCGATCTGAACCCGCCACCGGAAGCGAAGCA
AGTCCCTGTCAGCTACTACGATTCGACGTACCTGAGCACGGATAACGAAA
AAGATAACTACCTGAAAGGTGTGACCAAGCTGTTCGAACGTATCTACAGC
ACGGATCTGGGTCGCATGCTGCTGACTAGCATTGTTCGCGGTATCCCGTT
CTGGGGTGGTAGCACGATTGACACCGAACTGAAGGTTATCGACACTAACT
GCATTAACGTTATTCAACCGGATGGTAGCTATCGTAGCGAAGAGCTGAAT
CTGGTCATCATTGGCCCGAGCGCAGACATTATCCAATTCGAGTGCAAGAG
CTTTGGTCACGAGGTTCTGAATCTGACCCGCAATGGCTATGGTAGCACCC
AGTACATTCGTTTTTCGCCGGATTTTACCTTCGGCTTTGAAGAGAGCCTG
GAGGTTGATACCAATCCGTTGCTGGGTGCGGGCAAATTCGCTACCGATCC
GGCTGTCACGCTGGCCCATGAACTGATCCACGCAGGCCACCGCCTGTACG
GCATTGCCATCAACCCAAACCGTGTGTTCAAGGTTAATACGAATGCATAC
TACGAGATGAGCGGCCTGGAAGTCAGCTTCGAAGAACTGCGCACCTTCGG
TGGCCATGACGCTAAATTCATTGACAGCTTGCAAGAGAATGAGTTCCGTC
TGTACTACTATAACAAATTCAAAGACATTGCAAGCACGTTGAACAAGGCC
AAAAGCATCGTTGGTACTACCGCGTCGTTGCAGTATATGAAGAATGTGTT
TAAAGAGAAGTACCTGCTGTCCGAGGATACCTCCGGCAAGTTTAGCGTTG
ATAAGCTGAAGTTTGACAAACTGTACAAGATGCTGACCGAGATTTACACC
GAGGACAACTTTGTGAAATTCTTCAAAGTGTTGAATCGTAAAACCTATCT
GAATTTTGACAAAGCGGTTTTCAAGATTAACATCGTGCCGAAGGTGAACT
ACACCATCTATGACGGTTTTAACCTGCGTAACACCAACCTGGCGGCGAAC
TTTAACGGTCAGAATACGGAAATCAACAACATGAATTTCACGAAGTTGAA
GAACTTCACGGGTCTGTTCGAGTTCTATAAGCTGCTGTGCGTGCGCGGTA TCATCACCAGCAAAACCAAAAGCCTGGACAAAGGCTACAACAAGGCGCTG
AATGACCTGTGCATTAGGTAAACAATTGGGATCTGTTCTTTTCGCCATCC
GAAGATAATTTTACCAACGACCTGAAgAAGGGTGAAGAAATCACCAGCGA
TACGAATATTGAAGCAGCGGAAGAGAATATCAGCCTGGATCTGATCCAGC
AGTACTATCTGACCTTTAACTTCGACAATGAACCGGAGAACATTAGCATT
GAGAATCTGAGCAGCGACATTATCGGTCAGCTGGAACTGATGCCGAATAT
CGAACGTTTCCCGAACGGCAAAAAGTACGAGCTGGACAAGTACACTATGT
TCCATTACCTGCGTGCACAGGAGTTTGAACACGGTAAAAGCCGTATCGCG
CTGACCAACAGCGTTAACGAGGCCCTGCTGAACCCGAGCCGTGTCTATAC
CTTCTTCAGCAGCGACTATGTTAAGAAAGTGAACAAAGCCACTaAGGCCG
CGATGTTCCTGGGCTGGGTGGAACAGCTGGTATATGACTTCACGGACGAG
ACGAGCGAAGTGAGCACTACCGACAAAATTGCTGATATTACCATCATTAT
CCCGTATATTGGTCCGGCACTGAACATTGGCAACATGCTGTACAAAGACG
ATTTTGTGGGTGCCCTGATCTTCTCCGGTGCCGTGATTCTGCTGGAGTTC
ATTCCGGAGATTGCGATCCCGGTGTTGGGTACCTTCGCGCTGGTGTCCTA
CATCGCGAAgAAGGTTCTGACGGTTCAGACCATCGATAACGCGCTGTCGA
AACGTAATGAAAAATGGGACGAGGTTTACAAATACATTGTTACGAATTGG
CTGGCGAAAGTCAATACCCAGATCGACCTGATCCGTAAGAAAATGAAAGA
GGCGCTGGAGAATCAGGCGGAGGCCACCAAAGCAATTATCACTACCAATA
CAACCAGTACACGGAAGAAGAGAAGAATAAgATTAAgTTCAATATCGATG
ATTTGAGCAGCAAGCTGAATGAATCTATCAACAAAGCGATGATCAATATC
AACAAGTTTTTGAATCAGTGTAGCGTTTCGTACCTGATGAATAGCATGAT
TCCGTATGCGTCAAACGTCTGGAGGACTTCGACGCCAGCCTGAAAGATG
CGTTGCTGAAATACATTTACGACAATCGTGGTACGCTGAAgGGCCAAGTT
GACCGCTTGAAAGACAAAGTTAACAATACCCTGAGCACCGACATCCCATT
TCAACTGAGCAAGTATGTTGATAATCAACGTCTGTTGAGCACTTTCACCG
AGTATATCAAAAACATCATCAATACTAGCATTCTGAACCTGCGTTACGAG
AGCAATCATCTGATTGATCTGAGCCGTTATGCAAGCAAGATCAACATCGG
TAGCAAGGTCAATTTTGACCCGATCGATAAGAACCAGATCCAGCTGTTTA
ATCTGGAATCGAGCAAAATTGAGGTTATCCTGAAAAACGCCATTGTCTAC
AACTCCATGTACGAGAATTTCTCCACCAGCTTCTGGATTCGCATCCCGAA
ATACTTCAACAGCATTAGCCTGAACAACGAGTATACTATCATCAACTGTA
TGGAGAACAACAGCGGTTGGAAGGTGTCTCTGAACTATGGTGAGATCATT
TGGACCTTGCAGGACACCCAAGAGATCAAGCAGCGCGTCGTGTTCAAGTA
CTCTCAAATGATCAACATTTCCGATTACATTAATCGTTGGATCTTCGTGA
CCATTACGAATAACCGTCTGAATAACAGCAAGATTTACATCAATGGTCGC
TTGATCGATCAGAAACCGATTAGCAACCTGGGTAATATCCACGCAAGCAA
CAACATTATGTTCAAATTGGACGGTTGCCGCGATACCCATCGTTATATCT
GGATCAAGTATTTCAACCTGTTTGATAAGAACTGAATGAGAAGGAGATC
AAAGATTTGTATGACAACCAATCTAACAGCGGCATTTTGAAGGACTTCTG
GGGCGATTATCTGCAATACGATAAGCCGTACTATATGCTGAACCTGTATG -continued ATCCGAACAAATATGTGGATGTCAATAATGTGGGTATTCGTGGTTACATG
TATTTGAAGGGTCCGCGTGGCAGCGTTATGACGACCAACATTTACCTGAC
TCTAGCCTGTACCGTGGTACGAAATTCATCATTAAGAAATATGCCAGCGG
CAACAAAGATAACATTGTGCGTAATAACGATCGTGTCTACATCAACGTGG
TCGTGAAGAATAAAGAGTACCGTCTGGCGACCAACGCTTCGCAGGCGGGT
GTTGAGAAAATTCTGAGCGCGTTGGAGATCCCTGATGTCGGTAATCTGAG
CCAAGTCGTGGTTATGAAGAGCAAGAACGACCAGGGTATCACTAACAAGT
GCAAGATGAACCTGCAAGAACAACAATGGTAACGACATCGGCTTTATTGG
TTCCACCAGTTCAACAATATTGCTAAACTGGTAGCGAGCAATTGGTACAA
TCGTCAGATTGAGCGCAGCAGCCGTACTTTGGGCTGTAGCTGGGAGTTTA
TCCCGGTCGATGATGGTTGGGGCGAACGTCCGCTG SEQ ID NO: 5. Engineered BoNT/A, "CatH$_N$_v3", amino acid sequence.
MPFVNKQFNYKDPVNGVDIAYIKIPNAGQMQPVKAFKIHNKIWVIPERDT
FTNPEEGDLNPPPEAKQVPVSYYDSTYLSTDNEKDNYLKGVTKLFERIYS
TDLGRMLLTSIVRGIPFWGGSTIDTELKVIDTNCINVIQPDGSYRSEELN
LVIIGPSADIIQFECKSFGHEVLNLTRNGYGSTQYIRFSPDFTFGFEESL
EVDTNPLLGAGKFATDPAVTLAHELIHAGHRLYGIAINPNRVFKVNTNAY
YEMSGLEVSFEELRTFGGHDAKFIDSLQENEFRLYYYNKFKDIASTLNKA
KSIVGTTASLQYMKNVFKEKYLLSEDTSGKFSVDKLKFDKLYKMLTEIYT
EDNFVKFFKVLNRKTYLNFDKAVFKINIVPKVNYTIYDGFNLRNTNLAAN
FNGQNTEINNMNFTKLKNFTGLFEFYKLLCVRGIITSKTKSLDKGYNKAL
NDLCIKVNNWDLFFSPSEDNFTNDLNKGEEITSDTNIEAAEENISLDLIQ
QYYLTFNFDNEPENISIENLSSDIIGQLELMPNIERFPNGKKYELDKYTM
FHYLRAQEFEHGKSRIALTNSVNEALLKPSRVYTFFSSDYVKKVNKATEA
AMFLGWVEQLVYDFTDETSEVSTTDKIADITIIIPYIGPALNIGNMLYKD
DFVGALIFSGAVILLEFIPEIAIPKLGTFALVSYKANKVLTVQTIDNALS
KRNEKWDEVYKYIVTNWLAKVNTQIDLIRKKMKEALENQAEATKAIINYQ
YNQYKEKEKNNINFNIDDLSSKLNESINKAMININKFLNQCSVSYLMNSM
IPYGVKRLEDFDASLKDALLKYIYDNRGTLIGQVDRLKDKVNNTLSTDIP
FQLSKYVDNQRLLSTFTEYIKNIINTSILNLRYESNHLIDLSRYASKINI
GSKVNFDPIDKNQIQLFNLESSKIEVILKNAIVYNSMYENFSTSFWIRIP
KYFNSISLNNEYTIINCMENNSGWKVSLNYGEIIWTLQDTQEIKQRVVFK
YSQMINISDYINRWIFVTITNNRLNNSKIYINGRLIDQKPISNLGNIHAS
NNIMFKLDGCRDTHRYIWIKYFNLFDKELNEKEIKDLYDNQSNSGILKDF
WGDYLQYDKPYYMLNLYDPNKYVDVNNVGIRGYMYLKGPRGSVMTTNIYL
NSSLYRGTKFIIKKYASGNKDNIVRNNDRVYINVVVKNKEYRLATNASQA
GVEKILSALEIPDVGNLSQVVVMKSKNDQGITNKCKMNLQDNNGNDIGFI
GFHQFNNIAKLVASNWYNRQIERSSRTLGCSWEFIPVDDGWGERPL SEQ ID NO: 6. Engineered BoNT/A, "CatH$_N$_v3", nucleic acid sequence.
ATGCCATTCGTCAACAAGCAATTCAACTACAAAGACCCAGTCAACGGCGT
CGACATCGCATACATCAAGATTCCGAACGCCGGTCAAATGCAGCCGGTTA
AGGCTTTTAAGATCCACAACAAGATTTGGGTTATCCCGGAGCGTGACACC
TTCACGAACCCGGAAGAAGGCGATCTGAACCCGCCACCGGAAGCGAAGCA
AGTCCCTGTCAGCTACTACGATTCGACGTACCTGAGCACGGATAACGAAA
AAGATAACTACCTGAAAGGTGTGACCAAGCTGTTCGAACGTATCTACAGC
ACGGATCTGGGTCGCATGCTGCTGACTAGCATTGTTCGCGGTATCCCGTT
CTGGGGTGGTAGCACGATTGACACCGAACTGAAGGTTATCGACACTAACT
GCATTAACGTTATCCAACCGGATGGTAGCTATCGTAGCGAAGAGCTGAAT
CTGGTCATCATTGGCCCGAGCGCAGACATTATCCAATTCGAGTGCAAGAG
CTTTGGTCACGAGGTTCTGAATCTGACCCGCAATGGCTATGGTAGCACCC
AGTACATTCGTTTTTCGCCGGATTTTACCTTCGGCTTTGAAGAGAGCCTG
GAGGTTGATACCAATCCGTTGCTGGGTGCGGGCAAATTCGCTACCGATCC
GGCTGTCACGCTGGCCCATGAACTGATCCACGCAGGCCACCGCCTGTACG
GCATTGCCATCAACCCAAACCGTGTGTTCAAGGTTAATACGAATGCATAC
TACGAGATGAGCGGCCTGGAAGTCAGCTTCGAAGAACTGCGCACCTTCGG
TGGCCATGACGCTAAATTCATTGACAGCTTGCAAGAGAATGAGTTCCGTC
TGTACTACTATAACAAATTCAAAGACATTGCAAGCACGTTGAACAAGGCC
AAAAGCATCGTTGGTACTACCGCGTCGTTGCAGTATATGAAGAATGTGTT
TAAAGAGAAGTACCTGCTGTCCGAGGATACCTCCGGCAAGTTTAGCGTTG
ATAAGCTGAAGTTTGACAAACTGTACAAGATGCTGACCGAGATTTACACC
GAGGACAACTTTGTGAAATTCTTCAAAGTGTTGAATCGTAAAACCTATCT
GAATTTTGACAAAGCGGTTTTCAAGATTAACATCGTGCCGAAGGTGAACT
ACACCATCTATGACGGTTTTAACCTGCGTAACACCAACCTGGCGGCGAAC
TTTAACGGTCAGAATACGGAAATCAACAACATGAATTTCACGAAGTTGAA
GAACTTCACGGGTCTGTTCGAGTTCTATAAGCTGCTGTGCGTGCGCGGTA
TCATCACCAGCAAAACCAAAAGCCTGGACAAAGGCTACAACAAGGCGCTG
AATGACCTGTGCATTAAGGTAAACAATTGGGATCTGTTCTTTTCGCCATC
CGAAGATAATTTTACCAACGACCTGAACAAGGGTGAAGAAATCACCAGCg
AtACGAATATTGAAGCAGCGGAAGAGAATATCAGCCTGGATCTGATCCAG
CAGTACTATCTGACCTTTAACTTCGACAATGAACCGGAAACATTAGCATT
GAGAATCTGAGCAGCGACATTATCGGTCAGCTGGAACTGATGCCGAATAT
CGAACGTTTCCCGAACGGCAAAAAGTACGAGCTGGACAAGTACACTATGT
TCCATTACCTGCGTGCACAGGAGTTTGAACACGGTAAAAGCCGTATCGCG
CTGACCAACAGCGTTAACGAGGCCCTGCTGAAaCCGAGCCGTGTCTATAC
CTTCTTCAGCAGCGACTATGTTAAGAAAGTGAACAAAGCCACTGAGGCCG
CGATGTTCCTGGGCTGGGTGGAACAGCTGGTATATGACTTCACGGACGAG
ACGAGCGAAGTGAGCACTACCGACAAAATTGCTGATATTACCATCATTAT
CCCGTATATTGGTCCGGCACTGAACATTGGCAACATGCTGTACAAAGACG
ATTTTGTGGGTGCCCTGATCTTCTCCGGTGCCGTGATTCTGCTGGAGTTC

```
ATTCCGGAGATTGCGATCCCGaaGTTGGGTACCTTCGCGCTGGTGTCCTA
CAagGCGAATAAGGTTCTGACGGTTCAGACCATCGATAACGCGCTGTCGA
AACGTAATGAAAAATGGGACGAGGTTTACAAATACATTGTTACGAATTGG
CTGGCGAAAGTCAATACCCAGATCGACCTGATCCGTAAGAAAATGAAAGA
GGCGCTGGAGAATCAGGCGGAGGCCACCAAAGCAATTATCAACTACCAAT
ACAACCAGTACAaGGAAaAAGAGAAGAATAACATTAACTTCAATATCGAT
GATTTGAGCAGCAAGCTGAATGAATCTATCAACAAAGCGATGATCAATAT
CAACAAGTTTTTGAATCAGTGTAGCGTTTCGTACCTGATGAATAGCATGA
TTCCGTATGGCGTCAAACGTCTGGAGGACTTCGACGCCAGCCTGAAAGAT
GCGTTGCTGAAATACATTTACGACAATCGTGGTACGCTGATTGGCCAAGT
TGACCGCTTGAAAGACAAAGTTAACAATACCCTGAGCACCGACATCCCAT
TTCAACTGAGCAAGTATGTTGATAATCAACGTCTGTTGAGCACTTTCACC
GAGTATATCAAAAACATCATCAATACTAGCATTCTGAACCTGCGTTACGA
GAGCAATCATCTGATTGATCTGAGCCGTTATGCAAGCAAGATCAACATCG
GTAGCAAGGTCAATTTTGACCCGATCGATAAGAACCAGATCCAGCTGTTT
AATCTGGAATCGAGCAAAATTGAGGTTATCCTGAAAAACGCCATTGTCTA
CAACTCCATGTACGAGAATTTCTCCACCAGCTTCTGGATTCGCATCCCGA
AATACTTCAACAGCATTAGCCTGAACAACGAGTATACTATCATCAACTGT
ATGGAGAACAACAGCGGTTGGAAGGTGTCTCTGAACTATGGTGAGATCAT
TTGGACCTTGCAGGACACCCAAGAGATCAAGCAGCGCGTCGTGTTCAAGT
ACTCTCAAATGATCAACATTTCCGATTACATTAATCGTTGGATCTTCGTG
ACCATTACGAATAACCGTCTGAATAACAGCAAGATTTACATCAATGGTCG
CTTGATCGATCAGAAACCGATTAGCAACCTGGGTAATATCCACGCAAGCA
ACAACATTATGTTCAAATTGGACGGTTGCCGCGATACCCATCGTTATATC
TGGATCAAGTATTTCAACCTGTTTGATAAAGAACTGAATGAGAAGGAGAT
CAAAGATTTGTATGACAACCAATCTAACAGCGGCATTTTGAAGGACTTCT
GGGGCGATTATCTGCAATACGATAAGCCGTACTATATGCTGAACCTGTAT
GATCCGAACAAATATGTGGATGTCAATAATGTGGGTATTCGTGGTTACAT
GTATTTGAAGGGTCCGCGTGGCAGCGTTATGACGACCAACATTTACCTGA
ACTCTAGCCTGTACCGTGGTACGAAATTCATCATTAAGAAATATGCCAGC
GGCAACAAAGATAACATTGTGCGTAATAACGATCGTGTCTACATCAACGT
GGTCGTGAAGAATAAAGAGTACCGTCTGGCGACCAACGCTTCGCAGGCGG
GTGTTGAGAAAATTdTGAGCGCGTTGGAGATCCCTGATGTCGGTAATCTG
AGCCAAGTCGTGGTTATGAAGAGCAAGAACGACCAGGGTATCACTAACAA
GTGCAAGATGAACCTGCAAGACAACAATGGTAACGACATCGGCTTTATTG
GTTTCCACCAGTTCAACAATATTGCTAAACTGGTAGCGAGCAATTGGTAC
AATCGTCAGATTGAGCGCAGCAGCCGTACTTTGGGCTGTAGCTGGGAGTT
TATCCCGGTCGATGATGGTTGGGGCGACGTCCGCTG
```

SEQ ID NO: 7. Engineered BoNT/E light chain,
"CatLC", amino acid sequence.
MKIEEGKLVIWINGDKGYNGLAEVGKKFEKDTGIKVTVEHPDKLEEKFPQ

VAATGDGPDIIFWAHDRFGGYAQSGLLAEITPDKAFQDKLYPFTWDAVRY

NGKLIAYPIAVEALSLIYNKDLLPNPPKTWEEIPALDKELKAKGKSALMF

NLQEPYFTWPLIAADGGYAFKYENGKYDIKDVGVDNAGAKAGLTFLVDLI

KNKHMNADTDYSIAEAAFNKGETAMTINGPWAWSNIDTSKVNYGVTVLPT

FKGQPSKPFVGVLSAGINAASPNKELAKEFLENYLLTDEGLEAVNKDKPL

GAVALKSYEEELAKDPRIAATMENAQKGEIMPNIPQMSAFWYAVRTAVIN

AASGRQTVDEALKDAQTNSSSNNNNNNNNNLGIEGRISEFGSMPKINSF

NYNDPVNDRTILYIKPGGCQEFYKSFNIMKNIWIIPERNVIGTTPQDFHP

PTSLKNGDSSYYDPNYLQSDEEKDRFLKIVTKIFNRINNNLSGGILLEEL

SKANPYLGNDNTPDNKFHIGDASAVEIKFSKGSQHILLPNVIIMGAEPDL

FETNSSNISLRNNYMPSNHGFGSIAIVTFSPEYSFRFNDNSINEFIQDPA

LTLMHELIHSLHGLYGAKGITTTCIITQQKNPLITNRKGINIEEFLTFGG

NDLNIITVAQYNDIYTNLLNDYRKIASKLSKVQVSNPQLNPYKDIFQEKY

GLDKDASGIYSVNINKFDDILKKLYSFTEFDLATKFQVKCRETYIGQYKY

FKLSNLLNDSIYNISEGYNINNLKVNFRGQNANLNPRIIKPITGRGLVKK

IIRFAVDKLAAALEHHHHHH

SEQ ID NO: 8. Engineered BoNT/E light chain,
"CatLC", amino acid sequence.
ATGAAAATCGAAGAAGGTAAACTGGTAATCTGGATTAACGGCGATAAAGG

CTATAACGGTCTCGCTGAAGTCGGTAAGAAATTCGAGAAAGATACCGGAA

TTAAAGTCACCGTTGAGCATCCGGATAAACTGGAAGAGAAATTCCCACAG

GTTGCGGCAACTGGCGATGGCCCTGACATTATCTTCTGGGCACACGACCG

CTTTGGTGGCTACGCTCAATCTGGCCTGTTGGCTGAAATCACCCCGGACA

AAGCGTTCCAGGACAAGCTGTATCCGTTTACCTGGGATGCCGTACGTTAC

AACGGCAAGCTGATTGCTTACCCGATCGCTGTTGAAGCGTTATCGCTGAT

TTATAACAAAGATCTGCTGCCGAACCCGCCAAAAACCTGGGAAGAGATCC

CGGCGCTGGATAAAGAACTGAAAGCGAAAGGTAAGAGCGCGCTGATGTTC

AACCTGCAAGAACCGTACTTCACCTGGCCGCTGATTGCTGCTGACGGGGG

TTATGCGTTCAAGTATGAAAACGGCAAGTACGACATTAAAGACGTGGGCG

TGGATAACGCTGGCGCGAAAGCGGGTCTGACCTTCCTGGTTGACCTGATT

AAAAACAAACACATGAATGCAGACACCGATTACTCCATCGCAGAAGCTGC

CTTTAATAAAGGCGAAACAGCGATGACCATCAAGGCCCGTGGGCATGGTC

CAACATCGACACCAGCAAAGTGAATTATGGTGTAACGGTACTGCCGACCT

TCAAGGGTCAACCATCCAAACCGTTCGTTGGCGTGCTGAGCGCAGGTATT

AACGCCGCCAGTCCGAACAAAGAGCTGGCAAAAGAGTTCCTCGAAAACTA

TCTGCTGACTGATGAAGGTCTGGAAGCGGTTAATAAAGACAAACCGCTGG

GTGCCGTAGCGCTGAAGTCTTACGAGGAAGAGTTGGCGAAAGATCCACGT

ATTGCCGCCACTATGGAAAACGCCCAGAAAGGTGAAATCATGCCGAACAT

CCCGCAGATGTCCGCTTTCTGGTATGCCGTGCGTACTGCGGTGATCAACG

CCGCCAGCGGTCGTCAGACTGTCGATGAAGCCCTGAAAGACGCGCAGACT

-continued

```
AATTCGAGCTCGAACAACAACAACAATAACAATAACAACAACCTCGGGAT

CGAGGGAAGGATTTCAGAATTCGGATCCATGCCAAAAATCAACAGCTTTA

ATTACAATGACCCTGTAAACGATCGTACCATCCTATACATAAAGCCGGGT

GGGTGTCAAGAGTTCTACAAATCTTTCAATATTATGAAGAATATATGGAT

TATACCTGAGCGTAACGTTATTGGTACGACACCGCAAGATTTTCATCCAC

CTACTTCGTTGAAGAACGGTGACTCTTCCTATTACGACCCCAATTATCTC

CAGTCGGATGAAGAGAAGGACAGATTCCTTAAAATAGTAACCAAAATCTT

TAACAGGATTAATAACAATCTATCCGGAGGTATTTTGCTTGAAGAGCTTA

GTAAAGCTAATCCTTACCTAGGTAACGATAATACACCAGACAACAAGTTT

CATATAGGCGATGCATCCGCCGTGGAAATCAAATTTAGCAAGGGATCACA

GCATATTCTCTTGCCCAACGTTATTATAATGGGGCGGAACCAGATTTAT

TTGAAACAAATTCGAGTAATATTAGCCTGAGAAATAACTATATGCCGTCA

AACCATGGGTTCGGTAGCATAGCGATCGTTACTTTTTCTCCCGAATACAG

TTTTCGCTTCAATGATAATAGTATAAATGAGTTTATCCAAGACCCCGCAC

TCACGCTTATGCACGAACTCATACACTCTTTACACGGCCTGTATGGCGCT

AAGGGGATAACCACTACGTGTATCATTACTCAGCAAAAGAACCCATTGAT

AACGAACAGGAAGGGCATTAACATCGAGGAATTTCTTACATTTGGAGGCA

ACGATCTGAACATTATAACTGTCGCACAGTACAATGACATCTATACCAAC

TTACTAAATGATTATAGAAAAATCGCTTCTAAGTTATCCAAGGTTCAAGT

CTCAAACCCTCAACTGAATCCGTATAAGGACATATTCCAAGAGAAATATG

GATTAGACAAAGACGCGTCAGGAATCTATTCGGTAAACATTAACAAATTC

GACGATATTTTGAAGAAACTTTACAGCTTCACGGAGTTCGACTTGGCCAC

CAAATTCCAGGTCAAATGCCGAGAGACATACATCGGACAGTATAAGTATT

TCAAGCTGTCGAATCTCCTGAATGATTCCATATACAACATTAGTGAGGGT

TACAATATAAATAACCTAAAGGTGAATTTCCGAGGCCAAAACGCCAACCT

AAATCCGCGCATCATTAAACCCATCACAGGACGGGGGTTAGTGAAGAAAA

TAATCCGGTTTGCGGTCGACAAGCTTGCGGCCGCACTCGAGCACCACCAC

CACCACCAC
```

EXAMPLES

The following Examples serve to illustrate particular embodiments of the invention, and do not limit the scope of the invention defined in the claims in any way.

Example 1

Identification of Preferred Clostridial Toxin Amino Acids for Modification.

The amino acids identified as suitable candidates for modification (mutation sites) were selected using a number of different criteria.
1. Location of residue within BoNT molecule (within $H_N$, excluding belt region)
2. Location with regard to secondary/tertiary structure;
3. Type of residue;
4. Degree of surface exposure.

Acidic, neutral, polar and hydrophobic residues were considered for selection.

Exposed residues were determined using AreaIMol from the CCP4 suite. Each structure was analysed by AreaIMol, and exposed residues were identified as having a sum value greater than 55.

Secondary structures within the $H_N$ of each Subtype and TeNT were identified using a secondary structure assignment program (Stride Web Interface). Regions assigned as forming α-helix, β-strand or $3_{10}$-helix were excluded from the selection.

Sequences Used

Accession numbers:
BoNT/A: P10845
BoNT/B: P10844
BoNT/C: P18640
BoNT/D: P19321
BoNT/E: Q00496
BoNT/F: YP_001390123
BoNT/G: Q60393

Structural Data Source

Crystal structures of BoNT/A (3BTA.pdb), BoNT/B (1EPW), and BoNT/E (3FFZ.pdb) obtained from RCSB.

Homology modelling of $BoNT/C_1$, BoNT/D, BoNT/F, and BoNT/G performed using LOOPP and the following sequences, respectively: P18640, P19321, YP_001390123, and Q60393.

Preferred clostridial toxin amino acid residues for modification in the clostridial toxin $H_N$ domain:

BoNT/A:
D474, N476, D484, N486, I487, E488, A489, A490, E491, D546, E558, E560, H561, I566, L568, N570, S571, L577, N578, A597, E599, A601, E620, V621, T623, D625, T631, N645, L647, D650, D651, I668, E670, A672, V675, S683, I685, A686, N687, N752, Q753, T755, E756, E757, E758, N760, N761, I762, N763, D825, I831, G832, T847, D848, and D858

BoNT/B:
V443, G444, D453, S468, D533, E534, N535, T545, L548, D549, I550, D552, S557, L564, S566, N582, V584, N609, L619, N632, E633, G637, A646, I655, E657, V662, E669, S670, I672, D673, N739, I740, N748, N750, I818, G819, T834, I842, N845, and S858

$BoNT/C_1$:
L451, D452, C453, E455, V472, T474, D475, L478, N483, E484, E485, E487, I489, L555, S556, D557, N558, E560, D561, E569, N574, S575, T584, G592, Q594, G596, D617, N640, S641, V642, G645, N646, E661, E665, T667, A670, S678, V680, Q681, E682, S750, G751, S759, Q760, V826, G827, N842, T843, N847, and N853

BoNT/D:
Q469, E470, E473, N474, D479, E480, N482, V483, Q484, N485, S487, D488, S552, N553, N554, V555, E556, N557, I558, L560, T562, S563, V564, G569, S571, N572, G588, Q590, T614, D616, S619, S622, N636, S637, L639, G641, N642, E657, E661, T663, A666, V669, S674, I676, Q677, E678, S746, G747, D749, E751, N752, I753, Q756, N818, V822, G823, E837, N838, T839, N843, N849, and N850

BoNT/E:
D474, N476, E479, E480, D484, N486, I487, E488, A489, A490, E491, E492, L496, D497, Q500, Q501, L504, N507, D509, N510, N514, S516, E518, Q527, L530, N533, I534, E535, N539, Y548, I566, L568, D589, A597, E599, A601, L604, Y612, E620, N645, L647, Y648, D651, E737, E741, Y803, Y824, D825, G828, I831, G832, and D835

BoNT/F:
N463, E464, N468, T469, D474, D475, T476, T477, N478, N482, N485, N495, I499, Q501, I502, Q505, T506, N508, T509, V511, D513, D521, S522, S526, E527, I528, E529,

V534, D535, L536, E549, G550, T552, N553, S558, E566, E567, S568, V586, H587, Q608, D613, A616, D617, S619, N630, N633, N639, E654, V656, E658, L660, T663, L665, V666, S671, I673, G674, S675, S676, E677, N678, T746, N751, L753, E754, E756, N758, I759, N760, N761, S799, S821, I822, N840, S841, E845, L846, S847, S848, T850, N851, D852, I854, L855, and I856

BoNT/G:
N480, Q482, N483, N484, T485, E487, D540, N562, N570, N571, N572, T588, V589, T615, D621, N637, E638, E642, N643, I660, E662, I667, E674, S675, V677, G678, N679, S747, N755, D757, L823, D839, I841, D844, S846, and L847

TeNT:
A457, S458, L459, D461, L462, E486, E487, Q490, D491, N497, N504, D557, T571, T572, L573, Q574, N580, S581, N588, S589, T590, S598, Q605, G606, Q608, T631, I633, S640, Q655, E658, G659, N660, E675, I677, E679, T681, V684, A691, E692, S694, T695, Q696, A772, D773, E774, S862, N866, L867 and D868

Preferred clostridial toxin amino acid residues for modification in the BoNT/E light chain:
N5, N8, N10, D11, N14, D15, Q27, E28, N72, Q75, N118, D121, N122, Q123, N138, Q237, Q290, N297, N362, N365, D366, N378, and N379.

Example 2

Design of Engineered BoNT/a Molecules

Three different examples of an engineered BoNT/A molecule according to the present invention were produced.

Using the method described in Example 1, a total of 55 residues were identified as candidates for mutation in the BoNT/A H$_N$ domain. The suitability of the residues was further assessed by visual inspection of the BoNT/A crystal structure to give a list of 11 preferred candidates (N476, N763, N687, E599, I831, N761, N578, V675, I685, T755, E757). A further six residues were chosen based on functional data that showed that these residues were amenable to mutation without adversely affecting protein function. Four of these residues were within the candidate list (L647, D650, D651, T847) and two were not (S564, I849). With the 11 residues from the candidate list plus the six from functional data, a total of 17 residues were selected for mutation.

From the 17 residues selected, 3 constructs were made: CatH$_N$_v1, CatH$_N$_v2 and CatH$_N$_v3. The mutations for the CatH$_N$ constructs are shown in Table 3 below:

TABLE 3

CatH$_N$ constructs with mutations listed and calculated pI.

| | Mutations | Number of Mutations | Calculated pI | Calculated ΔpI relative to BoNT/A (pI 6.4) |
|---|---|---|---|---|
| CatHN_v1 | S564R, L647R, D650R, D651R, T847R, I849R | 6 | 7.4 | 1.0 |
| CatHN_v2 | N476K, N763K, N687K, E599K, I831K, N761K | 6 | 7.3 | 0.9 |

TABLE 3-continued

CatH$_N$ constructs with mutations listed and calculated pI.

| | Mutations | Number of Mutations | Calculated pI | Calculated ΔpI relative to BoNT/A (pI 6.4) |
|---|---|---|---|---|
| CatHN_v3 | N578K, V675K, I685K, T755K, E757K | 5 | 7.1 | 0.7 |

[ΔpI = change in isoelectric point]

Figure 1B:
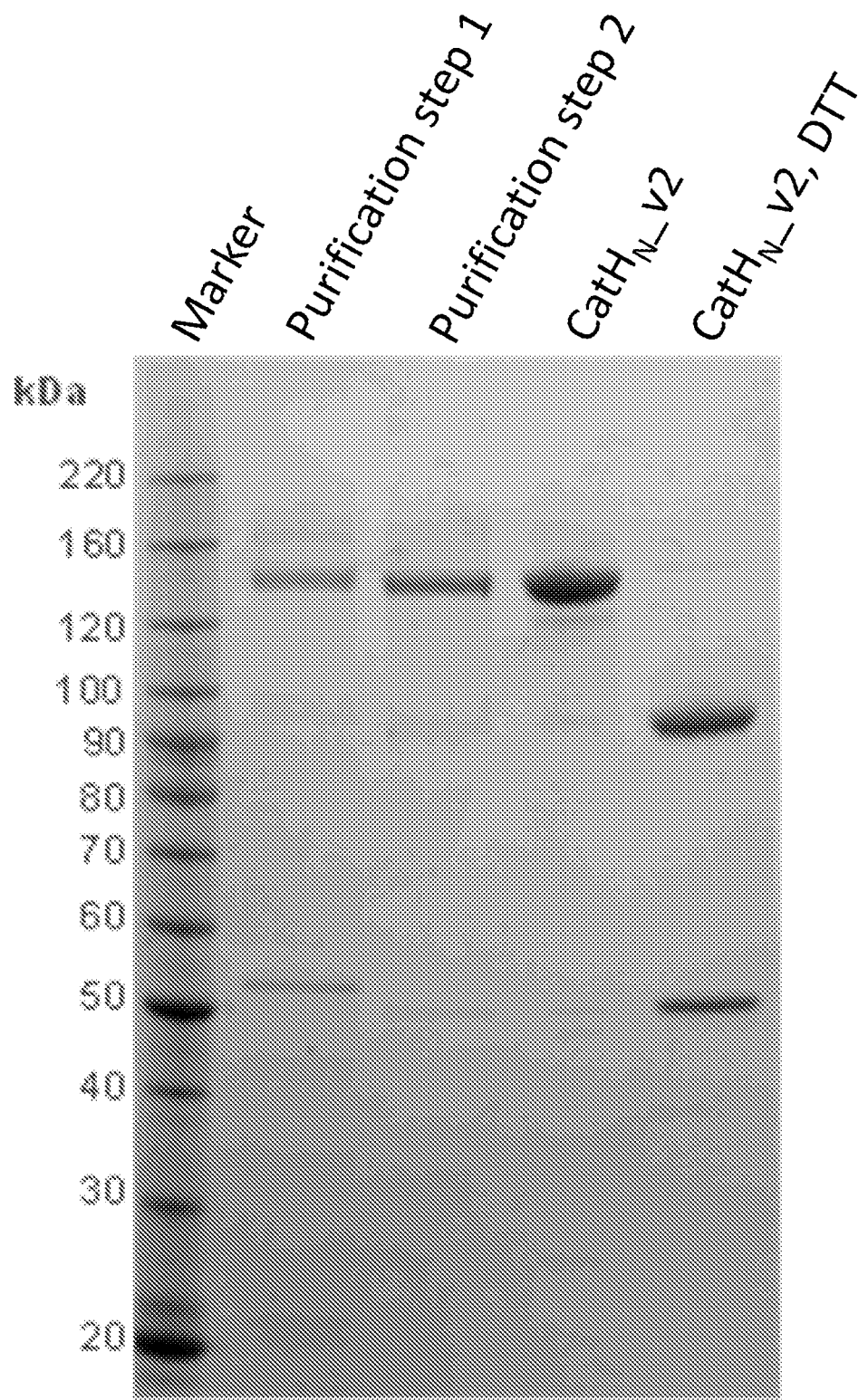
Figure 1C:
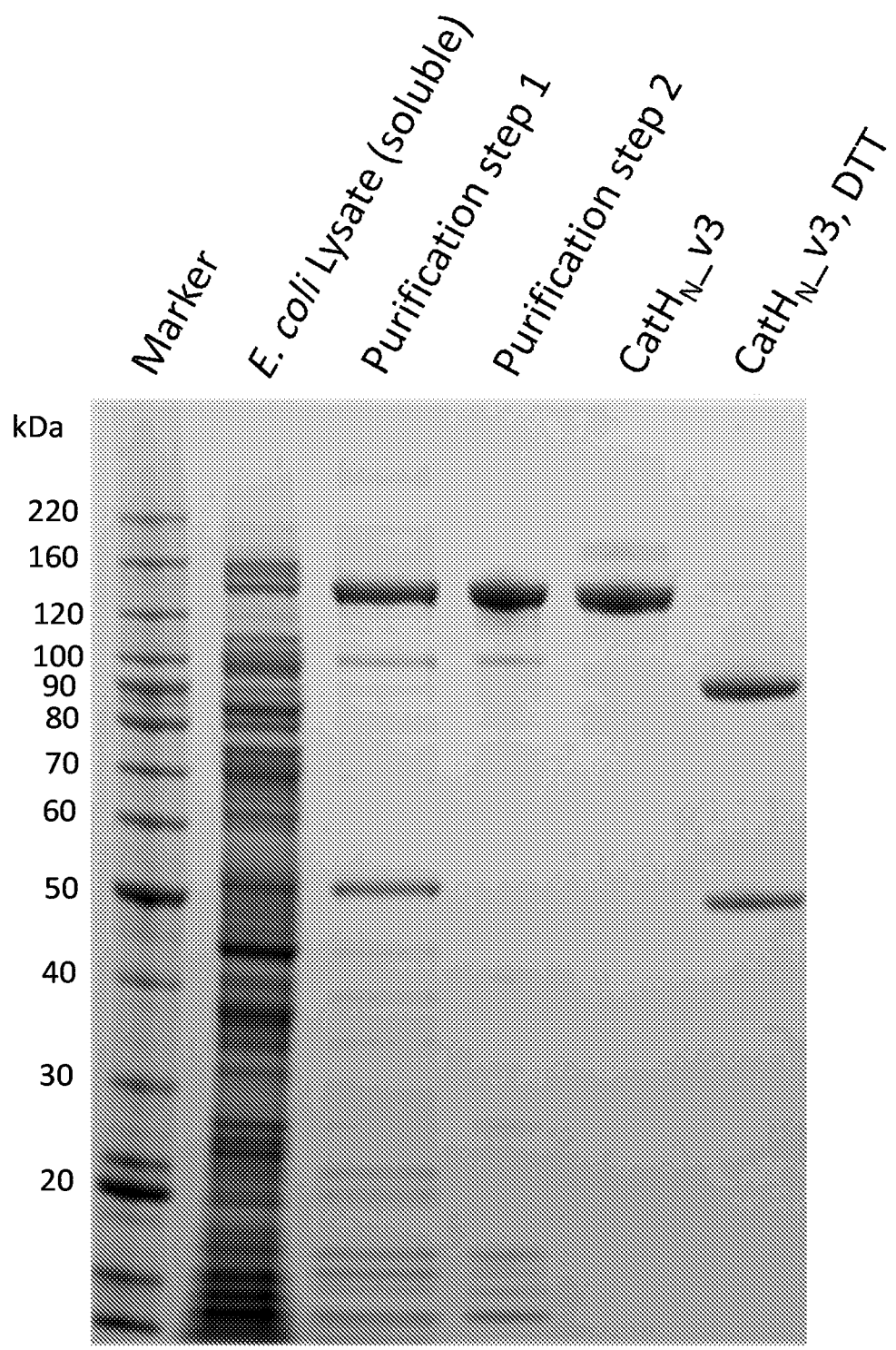

Purification of CatH$_N$_v1, CatH$_N$_v2 and CatH$_N$_v3 is shown in FIGS. 1A, 1B and 1C, respectively.

Example 3

Cloning, Expression and Purification

DNA constructs encoding the engineered BoNT/A molecules described in Example 2 were synthesised, cloned into the pJ401 expression vector and then transformed into BL21 (DE3) *E. coli*. This allowed for soluble over-expression of the recombinant engineered BoNT/A molecules in *E. coli*.

The recombinant engineered BoNTs were purified using classical chromatography techniques from the *E. coli* lysates. An initial purification step using a cation-exchange resin was employed, followed by an intermediate purification step using a hydrophobic interaction resin. The recombinant engineered BoNT single-chain was then cleaved by proteolysis, resulting in the activated di-chain engineered BoNT. A final purification step was then employed to remove remaining contaminants.

Example 4

Characterization of purified engineered BoNTs

The engineered BoNTs described in Example 2 above were characterised experimentally.

The ability of the engineered BoNTs to enter neurons and cleave SNAP-25 (the target of BoNT/A) was assessed using rat embryonic spinal cord neurons (eSCN). Potency of the engineered BoNTs was further assessed using the mouse phrenic nerve hemi-diaphragm assay (mPNHD).

CatH$_N$_v1:

The first set of mutations added were substitutions to Arginine:
S564R, L647R, D650R, D651R, T847R, I849R The CatH$_N$_v1 molecule was tested in the rat embryonic spinal cord neuron (eSCN) SNAP-25 cleavage assay, and found to be equipotent potent to BoNT/A (BoNT/A) (FIG. 2).

Figure 3:
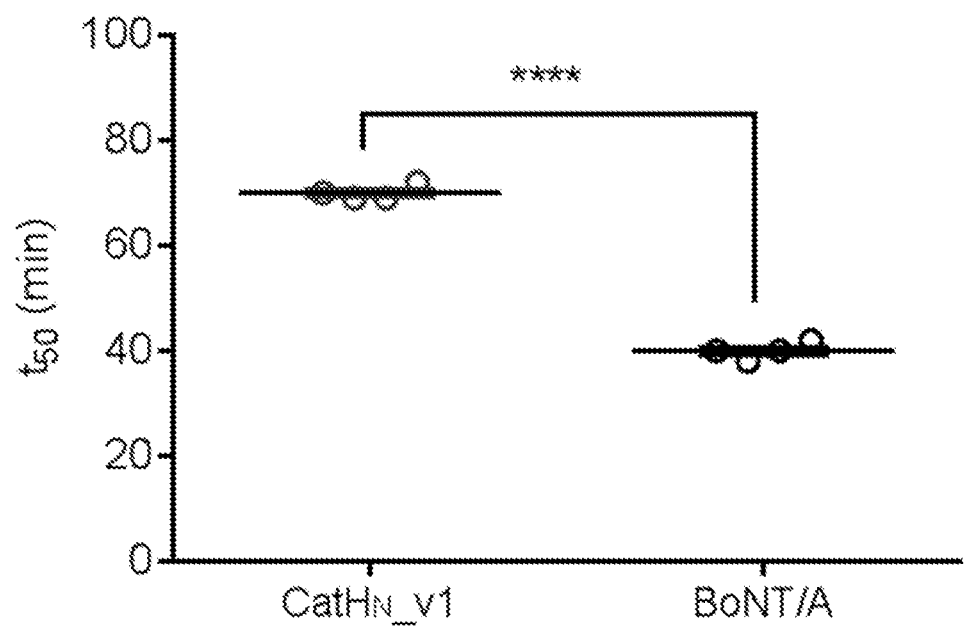

A positive result was also demonstrated in the mouse phrenic nerve hemi-diaphragm (mPNHD) assay (FIG. 3).

CatH$_N$_v2:

The second set of mutations were substitutions to Lysine:
N476K, N763K, N687K, E599K, I831K, N761K The CatH$_N$_v2 protein was tested in the eSCN SNAP-25 cleavage assay, and found to retain the ability to enter the cells and cleave SNAP-25. In the mPNHD assay CatH$_N$_v2 was equipotent to BoNT/A (FIGS. 4 and 5).

CatH$_N$_v3:

The third set of mutations were substitutions to Lysine:
N578K, V675K, I685K, T755K, E757K The CatH$_N$_v3 molecule was tested in the eSCN SNAP-25 cleavage assay, and found to retain the ability to enter the cells and cleave SNAP-25. Similarly, a positive result was also demonstrated in the mPNHD assay (FIGS. 6 and 7).

Isoelectric Focusing

All three CatH$_N$ constructs possess an increased p/compared to unmodified BoNT/A (FIG. 8).

Example 5

Modifications in the Light Chain of BoNT/E

Due to the modularity of the botulinum toxin, a BoNT/E light chain construct with an N-terminal maltose binding protein (MBP) tag and a C-terminal 6 histidine tag (6HT) was used as a surrogate to assay BoNT/E activity when mutated and characterised.

A BoNT/E light chain construct ("CatLC") was prepared having the mutations shown in table below.

TABLE 4

Construct with mutations listed, calculated pI and calculated ΔpI.

| | Mutations | Number of Mutations | Calculated pI | Calculated ΔpI relative to MBP-LC/E (pI 6.3) |
|---|---|---|---|---|
| CatLC | Q123K<br>N138K<br>Q237K | 3 | 6.6 | 0.3 |

Figure 9:
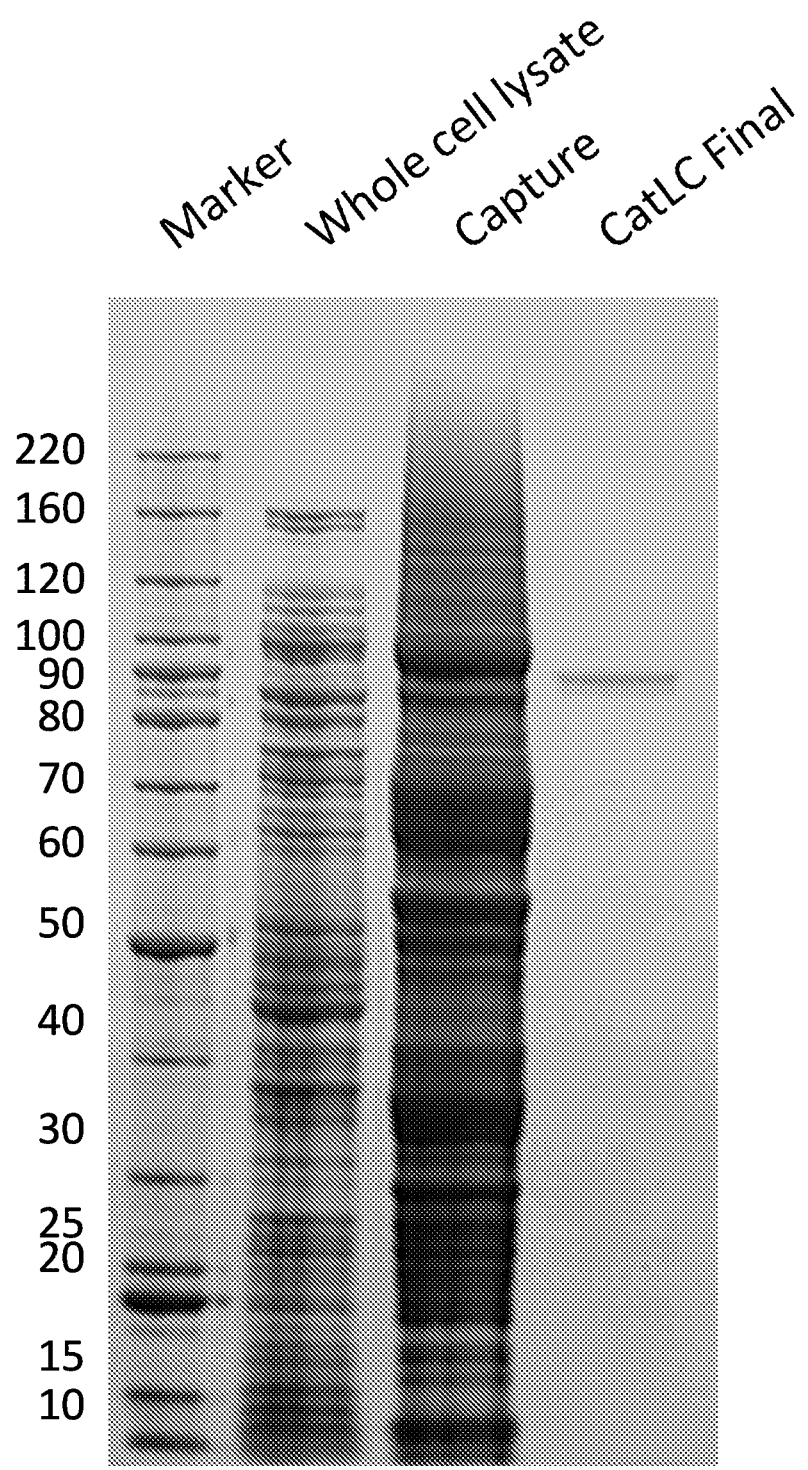

The construct was expressed in BL21 DE3 cells and purified using affinity chromatography. Purification is shown in FIG. 9.

Figure 10:
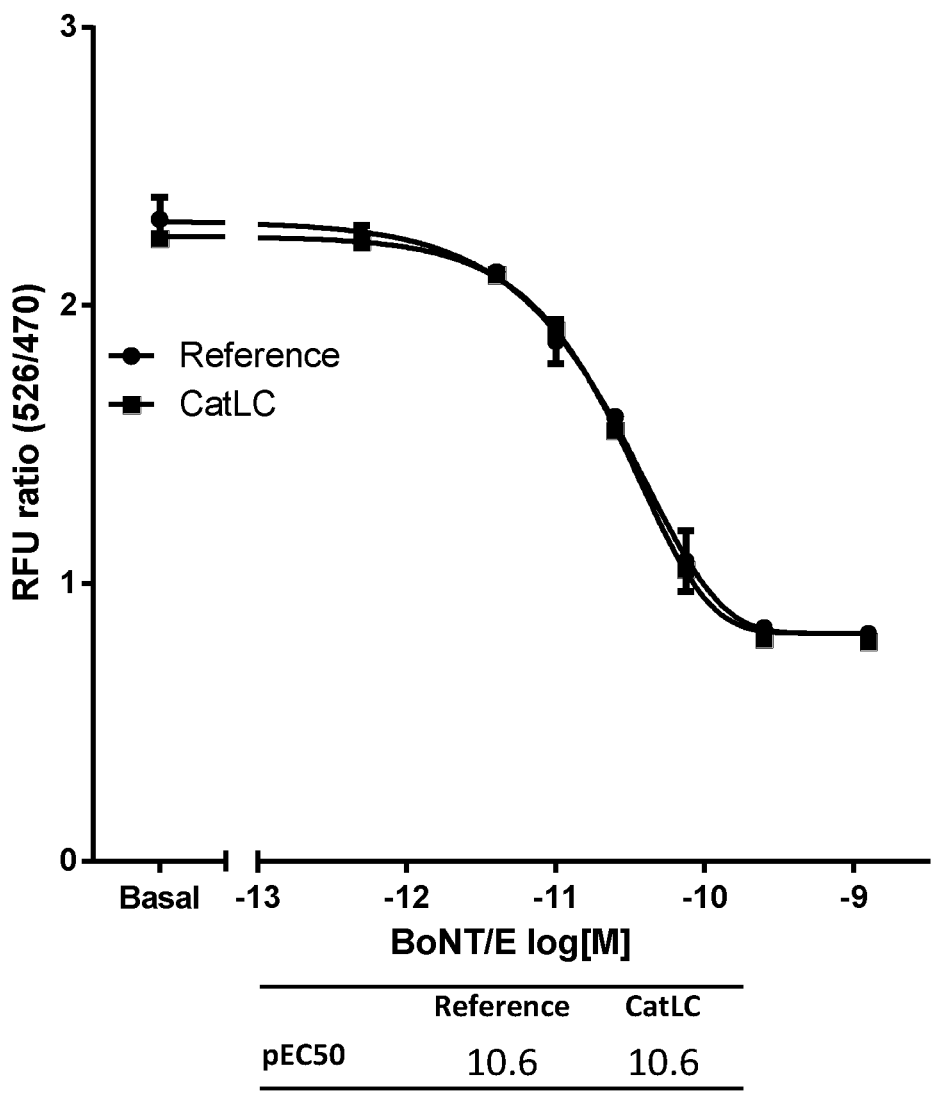

Assessment of the construct for catalytic activity showed that the modified light chain retained the catalytic activity of unmodified, light chain (FIG. 10).

The invention claimed is:

1. An engineered clostridial toxin comprising an amino acid modification that increases the isoelectric point of the toxin to a value that is at least 0.2 pI units higher than the isoelectric point of an otherwise identical toxin lacking the modification, wherein the modification is not located in the clostridial toxin binding domain and the clostridial light chain does not contain an E3 ligase recognition motif.

2. An engineered clostridial toxin comprising an amino acid modification located in the clostridial toxin translocation domain that increases the isoelectric point of the toxin to a value that is at least 0.2 pI units higher than the isoelectric point of an otherwise identical toxin lacking the modification.

3. The toxin of claim 1, wherein the modification increases the isoelectric point of the toxin to a value that is at least 0.5 pI units higher than the isoelectric point of an otherwise identical clostridial toxin lacking the modification.

4. The toxin of claim 1, wherein the modification increases the isoelectric point of the toxin to a value that is between 2 and 5 pI units higher than the isoelectric point of an otherwise identical clostridial toxin lacking the modification.

5. The toxin of claim 1, having an isoelectric point of at least 6.5.

6. The toxin of claim 1 having an isoelectric point of between 6.5 and 7.5.

7. The toxin of claim 1, wherein the modification is an amino acid substitution, an amino acid insertion, or an amino acid deletion.

8. The toxin of claim 7, wherein the modification is a substitution of an acidic amino acid residue with a basic amino acid residue, a substitution of an acidic amino acid residue with an uncharged amino acid residue, or a substitution of an uncharged amino acid residue with a basic amino acid residue.

9. The toxin of claim 1, comprising from 1 to 90 amino acid modifications.

10. The toxin of claim 1, comprising at least three amino acid modifications.

11. The toxin of claim 1, comprising from 4 to 40 amino acid modifications.

12. The toxin of claim 1, wherein the modification is to a surface exposed amino acid residue.

13. The toxin of claim 1, wherein the modification is to an amino acid residue selected from: aspartic acid, glutamic acid, histidine, asparagine, glutamine, serine, threonine, alanine, glycine, valine, leucine, and isoleucine.

14. The toxin of claim 13, wherein the amino acid residue is substituted with lysine or arginine.

15. The toxin of claim 1, wherein the toxin is BoNT/E and the amino acid modification does not involve a substitution with lysine at Q53, N72, N378, N379, R394, or T400.

16. A nucleic acid comprising a nucleic acid sequence encoding the toxin of claim 1.

17. A method of producing a single-chain engineered clostridial toxin protein having a light chain and a heavy chain, the method comprising expressing the nucleic acid of claim 16 in a suitable host cell, lysing the host cell to provide a host cell homogenate containing the single-chain engineered clostridial toxin protein, and isolating the single-chain engineered clostridial toxin protein.

18. A method of activating an engineered clostridial toxin, the method comprising providing a single-chain engineered clostridial toxin protein obtainable by the method of claim 17, contacting the protein with a protease that cleaves the protein at a recognition site located between the light chain and heavy chain, and converting the protein into a di-chain polypeptide wherein the light chain and heavy chain are joined together by a disulphide bond.

* * * * *

UNITED STATES PATENT AND TRADEMARK OFFICE
CERTIFICATE OF CORRECTION

PATENT NO. : 10,647,750 B2
APPLICATION NO. : 15/540637
DATED : May 12, 2020
INVENTOR(S) : Dina Brady Anderson, Gavin Stephen Hackett and Sai Man Liu It is certified that error appears in the above-identified patent and that said Letters Patent is hereby corrected as shown below:

In the Specification

Column 4, Line 25:
"MDM2 XXFXXWXXLXX (SEQ ID NO: 10)"

Should read:
-- MDM2 XXFXXXWXXLXX (SEQ ID NO: 10) --

Signed and Sealed this
Twenty-first Day of July, 2020

Andrei Iancu
*Director of the United States Patent and Trademark Office*